(12) United States Patent
Connor

(10) Patent No.: US 12,397,181 B2
(45) Date of Patent: Aug. 26, 2025

(54) PATHOGEN-FILTERING TRANSPARENT FACE MASK WITH AN AIR IMPELLOR ON THE BACK OF THE HEAD OR NECK

(71) Applicant: Robert A. Connor, St. Paul, MN (US)

(72) Inventor: Robert A. Connor, St. Paul, MN (US)

(73) Assignee: Medibotics LLC, Ham Lake, MN (US)

( * ) Notice: Subject to any disclaimer, the term of this patent is extended or adjusted under 35 U.S.C. 154(b) by 738 days.

(21) Appl. No.: 17/744,636

(22) Filed: May 14, 2022

(65) Prior Publication Data

US 2022/0266068 A1   Aug. 25, 2022

Related U.S. Application Data

(63) Continuation-in-part of application No. 17/547,207, filed on Dec. 9, 2021, now Pat. No. 11,383,107, which is a continuation-in-part of application No. 17/408,409, filed on Aug. 21, 2021, now Pat. No. 11,465,001, application No. 17/744,636 is a continuation-in-part of application No. 17/408,409, filed on Aug. 21, 2021, now Pat. No. 11,465,001, said application No. 17/547,207 is a continuation-in-part of application No. 17/175,675, filed on Feb. 14, 2021, now Pat. No. 11,471,711, said application No. 17/408,409 is a continuation-in-part of application No. 17/175,675, filed on Feb. 14, 2021, now Pat. No. 11,471,711, which is a continuation-in-part of application No. 16/910,625, filed on Jun. 24, 2020, now abandoned.

(60) Provisional application No. 63/088,664, filed on Oct. 7, 2020, provisional application No. 63/035,744, filed on Jun. 6, 2020, provisional application No.
(Continued)

(51) Int. Cl.
| A62B 18/02 | (2006.01) |
| A41D 13/11 | (2006.01) |
| A61M 16/00 | (2006.01) |
| A62B 7/10 | (2006.01) |
| A62B 18/00 | (2006.01) |

(52) U.S. Cl.
CPC .......... *A62B 18/02* (2013.01); *A41D 13/1161* (2013.01); *A61M 16/0069* (2014.02); *A62B 7/10* (2013.01); *A62B 18/006* (2013.01)

(58) Field of Classification Search
CPC .... A61M 16/0069; A62B 7/10; A62B 18/006; A62B 18/08
See application file for complete search history.

(56) References Cited

U.S. PATENT DOCUMENTS

| 4,323,063 A | 4/1982 | Fisichella |
| 4,848,366 A | 7/1989 | Aita |

(Continued)

OTHER PUBLICATIONS

Civility, 2020, "French Startup Launches First High-Tech Transparent Protective Anti-COVID Mask," AccessWire.com, Jun. 17, 2020.

(Continued)

Primary Examiner — Valerie L Woodward

(57) ABSTRACT

This invention is a protective face mask with a transparent portion which covers a wearer's nose and mouth, air intake and air exhaust ports on the front of the mask, one or more air impellors on the back of the wearer's head or neck, and one or more air tubes which conduct air between the air impellor and the transparent portion of the mask.

3 Claims, 25 Drawing Sheets

Related U.S. Application Data

63/023,331, filed on May 12, 2020, provisional application No. 63/017,718, filed on Apr. 30, 2020.

(56) References Cited

U.S. PATENT DOCUMENTS

| | | | |
|---|---|---|---|
| 4,951,662 A * | 8/1990 | Townsend, Jr. | A41D 13/1146 128/201.15 |
| 6,257,235 B1 * | 7/2001 | Bowen | A62B 23/025 128/206.12 |
| 7,802,572 B2 | 9/2010 | Hahne | |
| 10,758,751 B2 | 9/2020 | Feasey | |
| 10,945,469 B1 | 3/2021 | Rosenberg et al. | |
| 11,123,581 B1 | 9/2021 | Salvino et al. | |
| 2006/0230485 A1 | 10/2006 | Lee | |
| 2010/0239625 A1 | 9/2010 | Puckett | |
| 2011/0108035 A1 | 5/2011 | Samaniego | |
| 2012/0174922 A1 | 7/2012 | Virr et al. | |
| 2013/0104733 A1 | 5/2013 | Bangera et al. | |
| 2014/0373846 A1 | 12/2014 | Kao et al. | |
| 2016/0059049 A1 | 3/2016 | Langford | |
| 2017/0007861 A1 | 1/2017 | Parham et al. | |
| 2018/0028846 A1 | 2/2018 | Hur et al. | |
| 2018/0078798 A1 | 3/2018 | Fabian et al. | |
| 2018/0296864 A1 | 10/2018 | Feasey et al. | |
| 2018/0297676 A1 | 10/2018 | Zheng | |
| 2018/0304108 A1 | 10/2018 | Curtis | |
| 2019/0009114 A1 | 1/2019 | Han | |
| 2019/0069615 A1 | 3/2019 | Lam | |
| 2020/0206545 A1 | 7/2020 | Kim et al. | |
| 2020/0282242 A1 | 9/2020 | Virr et al. | |
| 2020/0353294 A1 | 11/2020 | Feasey | |
| 2020/0353296 A1 | 11/2020 | Crenshaw | |
| 2020/0376213 A1 | 12/2020 | He | |
| 2020/0376305 A1 | 12/2020 | Lang | |
| 2020/0397087 A1 | 12/2020 | Crenshaw | |
| 2020/0406069 A1 * | 12/2020 | Fu | A63B 23/18 |
| 2021/0001157 A1 | 1/2021 | Rashaud | |
| 2021/0077762 A1 | 3/2021 | Mauger | |
| 2021/0086005 A1 | 3/2021 | O'Brien | |
| 2021/0196992 A1 | 7/2021 | Yu | |
| 2021/0219636 A1 | 7/2021 | Stroiazzo-Mougin | |
| 2021/0228920 A1 | 7/2021 | Arigue | |

OTHER PUBLICATIONS

Honeywell, 2021, "Will.i.am Debuts Innovative Face Technology Concept," Honeywell.com, Apr. 6, 2021.

Razer, 2021, "Razer Unveils Smart Mask and Gaming Chair Concept Designs at CES 2021," Razer.com, Jan. 21, 2021.

Redcliffe Medical, 2020, "LEAF: Self-Sterilizing, Transparent N99+ Mask," PR Newswire, May 14, 2020.

Scharper, 2018, "Clearly A Better Mask: Alums Allysa Dittmar and Aaron Hsu are Reinventing the Surgical Mask to Make Quality Health Care Accessible," Johns Hopkins Magazine, Winter, 2018.

Stegman, 2021, "Ford Designs Clear N95 Masks to Help Deaf or Hard of Hearing," Arc Publishing, Feb. 3, 2021.

* cited by examiner

PATHOGEN-FILTERING TRANSPARENT FACE MASK WITH AN AIR IMPELLOR ON THE BACK OF THE HEAD OR NECK

CROSS-REFERENCE TO RELATED APPLICATIONS

This application is a continuation in part of U.S. patent application Ser. No. 17/547,207 filed on 2021 Dec. 9. This application is a continuation in part of U.S. patent application Ser. No. 17/408,409 filed on 2021 Aug. 21. U.S. patent application Ser. No. 17/547,207 was a continuation in part of U.S. patent application Ser. No. 17/408,409 filed on 2021 Aug. 21. U.S. patent application Ser. No. 17/547,207 was a continuation in part of U.S. patent application Ser. No. 17/175,675 filed on 2021 Feb. 14. U.S. patent application Ser. No. 17/408,409 was a continuation in part of U.S. patent application Ser. No. 17/175,675 filed on 2021 Feb. 14. U.S. patent application Ser. No. 17/408,409 claimed the priority benefit of U.S. provisional patent application 63/088,664 filed on 2020 Oct. 7. U.S. patent application Ser. No. 17/175,675 claimed the priority benefit of U.S. provisional patent application 63/088,664 filed on 2020 Oct. 7. U.S. patent application Ser. No. 17/175,675 was a continuation in part of U.S. patent application Ser. No. 16/910,625 filed on 2020 Jun. 24. U.S. patent application Ser. No. 17/175,675 claimed the priority benefit of U.S. provisional patent application 63/035,744 filed on 2020 Jun. 6. U.S. patent application Ser. No. 17/175,675 claimed the priority benefit of U.S. provisional patent application 63/023,331 filed on 2020 May 12. U.S. patent application Ser. No. 17/175,675 claimed the priority benefit of U.S. provisional patent application 63/017,718 filed on 2020 Apr. 30. U.S. patent application Ser. No. 16/910,625 claimed the priority benefit of U.S. provisional patent application 63/035,744 filed on 2020 Jun. 6. U.S. patent application Ser. No. 16/910,625 claimed the priority benefit of U.S. provisional patent application 63/023,331 filed on 2020 May 12. U.S. patent application Ser. No. 16/910,625 claimed the priority benefit of U.S. provisional patent application 63/017,718 filed on 2020 Apr. 30. The entire contents of these applications are incorporated herein by reference.

FEDERALLY SPONSORED RESEARCH

Not Applicable

SEQUENCE LISTING OR PROGRAM

Not Applicable

BACKGROUND

Field of Invention

This invention relates to respiratory face masks.

INTRODUCTION

With the increase in airborne infectious disease and environmental air pollution, air-filtering face masks are increasingly important. The most common air-filtration face masks are passive filtration masks which do not have active ventilation mechanisms such as motorized air impellers. They rely on a person's inhalation and exhalation to draw air through air filters. Passive filtration masks have some advantages. They tend to be relatively light-weight, inexpensive, and do not generate noise.

However, passive filtration masks also have disadvantages. They tend to have either relatively poor air filtration (e.g. leaking air around their perimeter) or have increased levels of carbon dioxide, humidity, and heat in air within the mask. Also, they are almost universally opaque because transparent materials tend to be impermeable to airflow and thus aggravate the accumulation of carbon dioxide, humidity, and heat within the mask. Lack of transparency interferes with human communication which relies on viewing mouth expressions. This is especially true for interpersonal communication involving people who are hearing impaired. There is a need for a transparent smart mask which has a transparent portion which allows a person's mouth and facial expressions to be seen.

Although there are clear advantages of a face mask with a transparent portion through which the wearer's mouth and facial expressions can be seen, there are design challenges as well. One of these design challenges is how to achieve good air quality and circulation within a mask without having visually-obstructive and/or noisy components on the wearer's person's face and/or near the wearer's ears. Transparent material tends to be air impermeable, so some form of active ventilation and filtration is needed. However, air impellors on the front of a person's head tend to be visually-obstructive. They also tend to be noisy due to their proximity to the person's ears.

One way to address these visual and noise problems is to have an air impellor (e.g. an air impellor, fan, turbine, propeller, pump, and/or blower) and an air intake port on the back of a person's head or neck. Air can be conducted through from there to the front of the mask via an air tube or channel. However, this causes a new problem. The wearer cannot see what is happening near an air intake port on the back of their head or neck. For example, a wearer standing in a subway car cannot see if a person behind them is coughing toward their air intake port. As another example, a wearer will not see if an air intake port on the back of their head or neck becomes clogged with hair and/or dust.

Disclosed herein is a protective pathogen-filtering face mask which solves this problem. This novel protective face mask comprises: a transparent portion which covers a wearer's nose and mouth; air intake and air exhaust ports on the front of the mask; one or more air impellors (e.g. air impellors, fans, turbines, propellers, pumps, and/or blowers) on the back of the wearer's head or neck; and one or more air tubes which conduct air between the air impellor and the transparent portion of the mask. This novel design: enables other people to see the wearer's mouth and facial expressions; filters air inflow and air outflow; achieves good air quality and circulation even with a transparent portion; does not clutter the front of the mask with visually obtrusive and noisy components; and enables the wearer to see what is happening around their air intake port.

REVIEW OF THE RELEVANT ART

In the patent literature, U.S. Pat. No. 4,323,063 (Fisichella, Apr. 6, 1982, "Medical Face Mask") discloses a medical mask with a transparent central portion. U.S. Pat. No. 4,848,366 (Aita, Jul. 18, 1989, "Exhaust Mask System and Device") discloses a mask system including a front portion defining a surface which is generally C-shaped with curved surfaces in both the horizontal and vertical cross sections. U.S. Pat. No. 6,257,235 (Bowen, Jul. 10, 2001, "Face Mask with Fan Attachment") discloses a face mask with a fan attachment to enhance breathability and comfort. U.S. Patent Application 20060230485 (Lee, Oct. 19, 2006, "See-Through Mask") discloses a see-through mask for preventing infection of disease-causing bacteria and dust.

U.S. Patent Application 20100239625 (Puckett, Sep. 23, 2010, "Transparent Antimicrobial Face Mask") discloses a generally transparent mask which is perforated with elongate slits. U.S. Pat. No. 7,802,572 (Hahne, Sep. 28, 2010, "Face Mask") discloses a medical mask with a transparent central portion. U.S. Patent Application 20110108035 (Samaniego, May 12, 2011, "Nex-Gen Respirator/Surgical Mask") discloses a face mask with a transparent shell. U.S. Patent Application 20120174922 (Virr et al., Jul. 12, 2012, "Respirator") discloses a mask with a neck component which surrounds the back of a user's neck.

U.S. Patent Application 20130104733 (Bangera et al., May 2, 2013, "Air-Treatment Mask Systems, and Related Methods and Air-Treatment Masks") discloses air-treatment mask systems having at least one controllable air-treatment device that is controlled responsive to one or more signals from at least one pollutant sensor. U.S. Patent Application 20140373846 (Kao et al., Dec. 25, 2014, "Breathing Apparatus") discloses a powered air purifying respirator with a filter and impellor behind a user's head. U.S. Patent Application 20160059049 (Langford, Mar. 3, 2016, "Respirator Filter Interface") discloses a respiratory inlet having a mask end and a fitting end.

U.S. Patent Application 20170007861 (Parham et al., Jan. 12, 2017, "Heat Deformable Material for Face Seal") discloses thermally deformable face seals and respirators including such face seals. U.S. Patent Application 20180028846 (Hur et al., Feb. 1, 2018, "Breath Responsive Powered Air Purifying Respirator") discloses an air purifying respirator with a dual stage fan that sucks outside air in through the filter canisters and then pushes the filtered air on to the user's mask or hood, where excess air escapes. U.S. Patent Application 20180078798 (Fabian et al., Mar. 22, 2018, "Respiratory Masks, Systems and Methods") discloses a respirator or breathing air filter system including physiological data sensing, environmental data sensing, user input, user output, and communication network connectivity.

U.S. Patent Application 20180297676 (Zheng, Oct. 18, 2018, "Respiratory Face Mask") discloses a transparent mask with an outer edge that is double-layered and forms an exhaust passage. U.S. Patent Application 20180296864 (Feasey et al., Oct. 18, 2018, "Respirator") discloses a mask or shield comprising a flow of positive pressure air directed through substantially opposing jets that creates a stream of laminar flow filtered air. U.S. Patent Application 20180304108 (Curtis, Oct. 25, 2018, "Nasal Filtration System") discloses a nasal filtration system that can be inserted into the nasal passages. U.S. Patent Application 20190009114 (Han, Jan. 10, 2019, "Harmful-Substance-Blocking Health Mask Using Air Curtain") discloses a mask which creates an air curtain to block entry of external substances.

U.S. Patent Application 20190069615 (Lam, Mar. 7, 2019, "Face Mask Having Transparent Plastic Piece") discloses a face mask with a transparent plastic piece, a first conformable member affixed to a first portion of the back side of the piece, and a second conformable member affixed to a second portion of the back side of the piece. U.S. Patent Application 20200206545 (Kim et al., Jul. 2, 2020, "Mask Apparatus") discloses a mask device with at least one inlet and at least one outlet located below the inlet, a first air cleaner and a second air cleaner for filtering outside air sucked in from an outside environment and supplying the filtered air through the mask body to the inlet, the first air cleaner coupled to one side of the mask body and the second air cleaner coupled to an opposite side of the mask body.

U.S. Patent Application 20200282242 (Virr et al., Sep. 10, 2020, "Portable Personal Respirator and Use Thereof") discloses a respirator system with an air filter, a flow generator with a sensorless DC motor, a mask, a processor, a sensor, an electric power source, and a wireless transceiver. U.S. Patent Application 20200353294 (Feasey, Nov. 12, 2020, "Respirator") and U.S. patent Ser. No. 10/758,751 (Feasey, Sep. 1, 2020, "Respirator") disclose a mask or shield with opposing jets that create a stream of laminar flow filtered air. U.S. Patent Application 20200353296 (Crenshaw, Nov. 12, 2020, "Designed Medical Mask") discloses a designer medical mask that allows a user to quickly and easily change the outer appearance or design of the medical mask.

U.S. Patent Application 20200376213 (He, Dec. 3, 2020, "Miniature Air Filtration Assembly for a Medical Field") discloses a miniature vacuum unit including a suction tube. U.S. Patent Application 20200376305 (Lang, Dec. 3, 2020, "Personal Protective Equipment System for Safe Air, Train or Bus Travel Protecting Against Infectious Agents Including Novel Coronavirus—Covid-19") discloses personal respiratory protection systems for use during travel on an aircraft, train, or bus. U.S. Patent Application 20200397087 (Crenshaw, Dec. 24, 2020, "Electronic Airflow Mask") discloses a mask with a sensor and a multi-speed fan.

U.S. Patent Application 20200406069 (Fu, Dec. 31, 2020, "Versatile and Multi-Purpose Breathing Mask") discloses a modular respirator comprising an elongate filter unit having a filter inlet, a filter outlet, and a replaceable fluid filter for filtering pollutants within the fluid. U.S. Patent Application 20210001157 (Rashaud, Jan. 7, 2021, "Personal Protective Face Shield for Preventing Biohazardous, Infectious or Pathological Aerosol Exposure (COVID-19)") discloses a face shield/window with an electrostatic double layer. U.S. patent Ser. No. 10/945,469 (Rosenberg et al., Mar. 16, 2021, "Respirator") discloses a respirator mask with a transparent front panel and a filter that extends around at least a portion of the perimeter of the mask.

U.S. Patent Application 20210077762 (Mauger, Mar. 18, 2021, "Respirator Devices with Source Control Mechanisms and Associated Systems and Methods") discloses a mask which filters air outflow to reduce the spread of contagious disease. U.S. Patent Application 20210086005 (O'Brien, Mar. 25, 2021, "Facemask Having Integrated Modules") discloses a facemask with integrated modules having sensors and other mechanisms. U.S. Patent Application 20210196992 (Yu, Jul. 1, 2021, "Combination Air Filter and Protective Mask") discloses a combination air filter and protective mask with an air pump, a first line having a first end connected to the air pump, an air filter connected to a second end of the first line, a second line having a first end connected to the air filter, a connecter connected to a second end of the second line, a third line having a first end connected to the connector, and a full face mask connected to a second end of the third line.

U.S. Patent Application 20210219636 (Stroiazzo-Mougin, Jul. 22, 2021, "Ultraviolet Face Mask") discloses a transparent cover for covering the nose and mouth of a wearer and one or more UV-C LEDs to irradiate filter media. U.S. Patent Application 20210228920 (Arigue, Jul. 29, 2021, "Filtering Mask Assembly") discloses a filtering mask assembly with a housing comprising a fan and an outlet valve. U.S. patent Ser. No. 11/123,581 (Salvino et al., Sep. 21, 2021, "Anti-Contagion Mask") discloses anti-contagion transparent facemasks that do not obstruct visibility of a person's mouth when worn.

In the non-patent literature, Scharper, 2018, "Clearly A Better Mask: Alums Allysa Dittmar and Aaron Hsu Are Reinventing the Surgical Mask to Make Quality Health Care Accessible," Johns Hopkins Magazine, Winter, 2018, discloses a passive filtration mask with a transparent portion over a person's mouth, between upper and lower face-conforming foam portions.

Redcliffe Medical, 2020, "LEAF: Self-Sterilizing, Transparent N99+ Mask," PR Newswire, May 14, 2020, shows the concept of a transparent mask with an active filtration mechanism below a person's chin. Civility, 2020, "French Startup Launches First High-Tech Transparent Protective Anti-COVID Mask," AccessWire.com, Jun. 17, 2020, shows the concept of a generally-transparent face mask with circular (passive) air filters.

Razer, 2021, "Razer Unveils Smart Mask and Gaming Chair Concept Designs at CES 2021," Razer.com, Jan. 21, 2021, shows the concept of a mask with a transparent portion, active ventilation, lights, a microphone, and an ultraviolet-light charging case. Stegman, 2021, "Ford Designs Clear N95 Masks to Help Deaf or Hard of Hearing," Arc Publishing, Feb. 3, 2021, shows a prototype passive filtration mask with a transparent portion over a person's mouth. Honeywell, 2021, "Will.i.am Debuts Innovative Face Technology Concept," Honeywell.com, Apr. 6, 2021, shows the "Xupermask"—a non-transparent active filtration mask with multi-speed fans and advanced audio functions.

SUMMARY OF THE INVENTION

This invention is a novel protective face mask with: a transparent portion which covers a wearer's nose and mouth; air intake and air exhaust ports on the front of the mask; one or more air impellors (e.g. air impellors, fans, turbines, propellers, pumps, and/or blowers) on the back of the wearer's head or neck; and one or more air tubes which conduct air between the air impellor and the transparent portion of the mask. This design enables other people to see the wearer's mouth and facial expressions, filters air inflow and air outflow, achieves good air quality and circulation, does not clutter the front of the mask with visually obtrusive and noisy components, and enables the wearer to see what is happening around the air intake port.

INTRODUCTION TO THE FIGURES

DETAILED DESCRIPTION OF THE FIGURES

Figure 1:
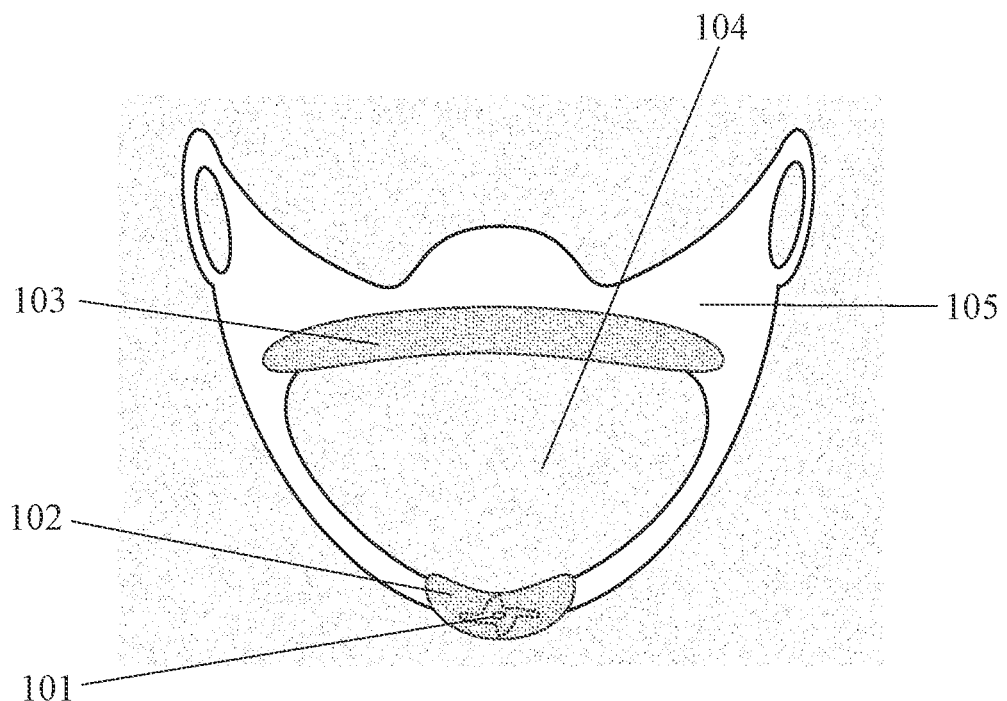
FIG. 1 shows a face mask with a transparent portion, a non-transparent portion, a longitudinal air filter above a mouth, and an air filter and impellor below the mouth.

Before discussing the specific examples of transparent protective face masks which are shown in FIGS. 1 through 49, it is useful to discuss some generic design concepts and variations which can generally be applied to these examples. In an example, a protective face mask can comprise: a concave transparent portion which covers a person's mouth; an air intake port within 4" of the concave transparent portion; an air exhaust port within 4" of the concave transparent portion; an air impellor (e.g. air impellor, fan, turbine, propeller, pump, and/or blower) located on the back of the person's head or neck; a first air tube or channel which conducts air from the air intake port to the air impellor; a second air tube or channel) which conducts air from the air impellor to a concave interior of the transparent portion; an air intake filter that filters airflow between the air intake port and the air impellor; and an air exhaust filter which filters airflow between the transparent portion and the air exhaust port.

In an example, a protective face mask can comprise: a concave transparent portion which covers a person's mouth; an air intake port within 4" of the concave transparent portion; an air exhaust port within 4" of the concave transparent portion; an air impellor (e.g. air impellor, fan, turbine, propeller, pump, and/or blower) located on the back of the person's head or neck; a first air tube or channel which loops above an ear and conducts air from the air intake port to the air impellor; and a second air tube or channel which loops above an ear and conducts air from the air impellor to a concave interior of the transparent portion. In an example, this face mask can further comprise: an air intake filter between the environment and the air impellor and an air exhaust filter between the concave interior of the transparent portion and the environment.

In an example, a protective face mask can comprise: a concave transparent portion which covers a person's mouth; an air intake port to one side (e.g. to the right) of the concave transparent portion; an air exhaust port to the opposite side (e.g. to the left) of the concave transparent portion; an air impellor (e.g. air impellor, fan, turbine, propeller, pump, and/or blower) located on the back of the person's head or neck; a first air tube or channel which conducts air from the air intake port to the air impellor; and a second air tube or channel which conducts air from the air impellor to a concave interior of the transparent portion. In an example, this face mask can further comprise: an air intake filter between the air intake port of the air impellor; and an air exhaust filter between the concave interior of the transparent portion and the air exhaust port.

In an example, a protective face mask can comprise: a face mask worn by a person, wherein the face mask further comprises a transparent front portion which covers the person's mouth; wherein the face mask further comprises an air impellor (e.g. air impellor, fan, turbine, propeller, pump, and/or blower) on the back of the person's head or neck; a right-side air tube (e.g. air tube or channel) which spans above the person's right ear between the transparent portion and the air impellor; a left-side air tube (e.g. air tube or channel) which spans above the person's left ear between the air impellor and a concave interior of the transparent portion.

In an example, a face mask can include an air valve which is in fluid communication with an air port and/or an air filter. In an example, this air valve can be a one-way valve. In an example, this air valve can be automatically opened or closed based on analysis of data from one or more environmental sensors or biometric sensors which are also part of the mask. In an example, this air valve can be closed when an airborne environmental hazard is detected by a sensor. In an example, this air valve can be opened when a greater need for oxygen by the wearer is indicated a sensor or when air inside a mask has low oxygen content. In an example, the direction of airflow through an air valve can be automatically changed based on analysis of data from one or more environmental sensors or biometric sensors in the mask.

In an example, when an air valve is in a first configuration, then air entering a face mask can go through just one air filter, but when the air valve is in a second configuration, then air entering the face mask can go through two or more air filters. In an example, when an air valve is in a first configuration, then air entering a face mask goes through an air filtering pathway with a first length, but when the air valve is in a second configuration, then air entering the face mask goes through an air filtering pathway with a second length, wherein the second length is longer than the first length. In an example, when an air valve is in a first configuration, then air entering a face mask goes through a first air filtering pathway, but when the air valve is in a second configuration, then air entering the face mask goes through a second air filtering pathway with a second length, wherein the second pathway is more convoluted than the first pathway.

In an example, a first air filter can have an electrostatic charge, a second air filter configured in series with the first air filter can have a second electrostatic charge, and the second charge can be greater than the first charge. In an example, a first air filter can have a first depth, a second air filter configured in series with the first air filter can have a second depth, and the second depth can be greater than the first depth. In an example, a first air filter can have a first width, a second air filter configured in series with the first air filter can have a second width, and the second width can be greater than the first width. In an example, a first air filter can have a first shape, a second air filter configured in series with the first air filter can have a second shape, and the second shape can be different than the first shape.

In an example, an air filter and/or air filtration pathway can be reticulated. In an example, an air filter and/or air filtration pathway can be pleated. In an example, an air filter and/or air filtration pathway can be corrugated. In an example, an air filter and/or air filtration pathway can be undulating and/or sinusoidal. In an example, an air filter and/or air filtration pathway can be convoluted.

In an example, a face mask can comprise: a concave transparent portion which covers a person's mouth; a first air filter which is in fluid communication with a concave interior of the transparent portion; a second air filter which is in fluid communication with the concave interior of the transparent portion; an environmental sensor or biometric sensor; and an air valve which is in fluid communication with the second air filter, wherein the air valve is closed when analysis of data from the environmental sensor detects an environmental hazard and/or is opened when analysis of data from the biometric sensor indicates that the person needs more airflow (e.g. more oxygen and/or less carbon dioxide).

In an example, a face mask can further comprise a chemical sensor. In an example, a face mask can further comprise a Global Positioning System (GPS) component. In an example, a face mask can further comprise a heart rate or pulse sensor. In an example, a face mask can further comprise a humidity sensor. In an example, a face mask can further comprise a microphone which is in acoustic communication with the interior of the mask and records a person's voice. In an example, the person's voice can then be broadcast and/or reproduced from a speaker on the exterior of the mask.

In an example, a face mask can further comprise a motion sensor (e.g. such as an accelerometer and gyroscope). In an example, the rotational speed of an air impellor can be increased when a motion sensor detects more vigorous motion (e.g. exercise) which is associated with greater need for oxygen by the wearer. In an example, a valve can open to allow airflow through a greater number of air filters and/or a greater surface area of air filtration when a motion sensor detects more vigorous motion (e.g. exercise) which is associated with greater need for oxygen by the wearer In an example, a face mask can be part of a wearable system which includes an EMG sensor on smart clothing and/or a separate wearable device with which the face mask is in wireless communication. In an example, the rotational speed of an air impellor can be increased when analysis of data from an EMG sensor detects more vigorous motion (e.g. exercise) which is associated with greater need for oxygen by the wearer. In an example, a valve can open to allow airflow through a greater number of air filters and/or a greater surface area of air filtration when analysis of data from an EMG sensor detects more vigorous motion (e.g. exercise) which is associated with greater need for oxygen by the wearer.

In an example, a face mask can have an oxygen sensor which monitors the oxygen level of the interior of the mask. In an example, a face mask can further comprise one or more environmental sensors which monitor for environmental hazards. In an example, a face mask can further comprise one or more biometric or physiological sensors which monitor the wearer's health and function. In an example, airflow speed or volume through an air impellor can be automatically changed based on analysis of data from an environmental, biometric, or physiological sensor.

In an example, a mask can be held on a person's head by a right-side strap and a left-side strap, wherein a strap loops around an ear, wherein there are one or more air tubes or channels within a strap, and wherein the one or more air tubes or channels conduct airflow between a front portion of the mask and an air impeller on the back of the person's head or neck. In an example, a mask can be held on a person's head by a right-side strap and a left-side strap, wherein a strap loops around an ear, wherein there are one or more flexible polymer cylindrical air tubes or channels within a strap, and wherein the one or more air tubes or channels conduct airflow between a front portion of the mask and an air impeller on the back of the person's head or neck.

In an example, air tubes or channels which conduct airflow between the front of a face mask and the back of a person's head or neck can be cylindrical. In an example, air tubes or channels which conduct airflow between the front of a face mask and the back of a person's head or neck can have a circular interior cross-section. In an example, air tubes or channels which conduct airflow between the front of a face mask and the back of a person's head or neck can have an elliptical or oval interior lumen. In an example, air tubes or channels which conduct airflow between the front of a face mask and the back of a person's head or neck can be reticulated, pleated, corrugated, undulating, and/or sinusoidal so that they can shrink or lengthen within an elastic strap as that strap shrinks or lengthens.

In an example, a protective face mask can comprise: a concave transparent portion which covers a person's mouth; an air intake filter within 4" of the concave transparent portion; an air exhaust filter within 4" of the concave transparent portion; an air impellor (e.g. air impellor, fan, turbine, propeller, pump, and/or blower) located on the back of the person's head or neck; a first air tube or channel which conducts air from the air intake filter to the air impellor; and a second air tube or channel which conducts air from the air impellor and to a concave interior of the transparent portion, wherein there are holes in the second air tube or channel which are in fluid communication with the concave interior of the transparent portion.

In an example, a protective face mask can comprise: a concave transparent portion which covers a person's mouth; an air intake filter around a first portion of the perimeter of the concave transparent portion; and an air exhaust filter around a second portion of the perimeter of the concave transparent portion. In an example, a protective face mask can comprise: a concave transparent portion which covers a person's mouth; an air intake filter around a first portion of a first side (e.g. right or left) of the perimeter of the concave transparent portion; and an air exhaust filter around a second portion of the opposite side (e.g. left or right) of the perimeter of the concave transparent portion.

In an example, a first virtual plane is the plane which best fits a transparent portion of a face mask, a second virtual plane is the plane which best fits an air intake filter, and the second plane can be substantially orthogonal to the first virtual plane. In an example, a first virtual plane is the vertical plane which divides the anterior vs. posterior halves of a person's head, a second virtual plane is the plane which best fits an air intake filter, and the second plane can be substantially orthogonal to the first virtual plane.

In an example, a concave transparent portion of a face mask can be horizontally asymmetric. In an example, the upper third of the transparent portion can be narrower than the lower third of the transparent portion. In an example, a concave transparent portion of a face mask can be horizontally asymmetric (e.g. its upper and lower halves can be different shapes and widths) but vertically symmetric (e.g. its right and left halves can be the same shape, albeit reflected, and width).

A "central vertical axis" of a transparent portion of mask can be defined as the vertical line which divides the transparent portion into two equal (right and left) sides. A "central horizontal axis" of a transparent portion of a mask can be defined as the horizontal line which intersects the mid-point of the central vertical axis. The "upper half" of the transparent portion can be defined as the part of the transparent portion which is above the central horizontal axis. The "lower half" of the transparent portion can be defined as the part of the transparent portion which is below the central horizontal axis. In an example, the front-facing surface area of the upper half of the transparent portion can be between 60% and 90% of the front-facing surface area of the lower half of the transparent portion. In an example, the front-facing surface area of the upper half of the transparent portion can be between 25% and 75% of the front-facing surface area of the lower half of the transparent portion.

In an example, a protective face mask can comprise: a concave transparent portion which covers a person's mouth; an air intake filter within 4" of the concave transparent portion; an air exhaust filter within 4" of the concave transparent portion; an air impellor (e.g. air impellor, fan, turbine, propeller, pump, and/or blower) located on the back of the person's head or neck; a first air tube (or channel) which conducts air between the air intake filter and the air impellor; and a second air tube (or channel) which conducts air between the air impellor and a concave interior of the transparent portion.

In an example, a protective face mask can comprise: a concave transparent portion which covers a person's mouth; an air intake filter to one side (e.g. to the right) of the concave transparent portion; an air exhaust filter to the opposite side (e.g. to the left) of the concave transparent portion; one or more air impellors (e.g. air impellors, fans, turbines, propellers, pumps, and/or blowers) located on the back of the person's head or neck; one or more air tubes (or channels) which conduct air from the air intake filter to the one or more air impellors; and one or more air tubes (or channels) which conduct air from the one or more air impellors to a concave interior of the transparent portion.

In an example, o'clock positions can be defined around the perimeter of a transparent portion of a face mask, wherein the 12 o'clock position is the highest point (centrally-located on a person's nose) and the 6 o'clock position is the lowest point (centrally-located under the person's mouth). In an example, an air filter can span the perimeter of a transparent portion of a face mask between the 7 o'clock to 11 o'clock positions. In an example, the ends of an air filter can be at the 7 o'clock position and the 11 o'clock position. In an example, an air filter can span the perimeter of a transparent portion of a face mask between 1 o'clock to 5 o'clock positions. In an example, the ends of an air filter can be at the 1 o'clock position and the 5 o'clock position.

In an example, a first air filter can span the perimeter of a transparent portion of a face mask between the 7 o'clock and 11 o'clock positions and a second air filter can span between the 1 o'clock and 5 o'clock positions around the perimeter of a transparent portion of a mask. In an example, a first air filter can span the perimeter of a transparent portion of a face mask between the 10 o'clock and 2 o'clock positions and a second air filter can span between the 4 o'clock and 8 o'clock positions around the perimeter of a transparent portion of a mask.

In an example, a protective face mask can comprise: a concave transparent portion which covers a person's mouth; an air intake port within 4" of the transparent portion; an air exhaust port within 4" of the transparent portion; an air intake filter; an air exhaust filter; and an air impellor (e.g. air impellor, fan, turbine, propeller, pump, and/or blower) on the back of the person's head or neck; and one or more air tubes or channels; wherein the one or more air tubes or channels conduct air from the air intake port to the air intake filter, from the air intake filter to the air impellor, from the air impellor to a concave interior of the transparent portion, from the transparent portion to the air exhaust filter, and from the air exhaust filter to the air exhaust port.

In an example, a protective face mask can comprise: a concave transparent portion which covers a person's mouth; an air intake port within 4" of the concave transparent portion; an air exhaust port within 4" of the concave transparent portion; an air impellor (e.g. air impellor, fan, turbine, propeller, pump, and/or blower) located on the back of the person's head or neck; a first air tube (or channel) which conducts air from the air intake port to the air impellor; a second air tube (or channel) which conducts air from the air impellor to a concave interior of the transparent portion, wherein there are a plurality of holes in the second air tube which are in fluid communication with the concave interior of the transparent portion; an air intake filter that filters airflow between the air intake port and the air impellor and an air exhaust filter that filters air which then flows out from the air exhaust port.

In an example, an air tube or channel which conducts air between a front portion of a face mask and an air impellor on the back of a person's head or neck can have a length between 7" to 15". In an example, an air tube or channel which conducts air between a front portion of a face mask and an air impellor on the back of a person's head or neck can have a length between 9" to 13". In an example, an air tube or channel which conducts air between a front portion of a face mask and an air impellor on the back of the person's head or neck can have a length which can change due to pleats, reticulations, and/or undulations of the air tube or channel. In an example, an air tube or channel which conducts air between a front portion of a face mask and an air impellor on the back of the person's head or neck can be within an elastic strap, wherein the length of the air tube or channel changes as the length of the strap changes due to pleats, reticulations, and/or undulations of the air tube or channel.

In an example, a protective face mask can comprise: a face mask worn by a person; wherein the face mask further comprises a concave transparent portion which covers the person's mouth; wherein the face mask further comprises an air intake port within 4" of the transparent portion, wherein air from the environment enters the air intake port; wherein the face mask further comprises an air intake filter within 4" of the transparent portion, wherein air from the air intake port enters the air intake filter; wherein the face mask further comprises a right-side air tube (e.g. air tube or channel) above the person's right ear, wherein air from the air intake filter enters the right-side air tube; wherein the face mask further comprises one or more air impellors (e.g. air impellors, fans, turbines, propellers, pumps, and/or blowers) on the back on the person's head or neck, wherein air from the right-side air tube enters the one or more air impellors; wherein the face mask further comprises a left-side air tube (e.g. air tube or channel) above the person's left ear, wherein air from the one or more air impellors enters the left-side air tube, and wherein air from the left-side air tube enters the concave interior of the transparent portion; wherein the face mask further comprises an air outflow filter on a front portion of the face mask, wherein air from the concave interior of the transparent portion enters the air outflow filter; and wherein the face mask further comprises an air exhaust port within 4" of the transparent portion; wherein air from air outflow filter enters the air outflow port, and wherein air from the air exhaust port is exhausted out into the environment.

In an example, a protective face mask can comprise: a first air impellor (e.g. air impellor, fan, turbine, propeller, pump, and/or blower) located on the back (e.g. on the posterior half) of a person's head or neck which draws air in from the environment into the interior concavity of the mask through an air intake filter; and a second air impellor located on the back (e.g. on the posterior half) of a person's head or neck which draws air out from the interior concavity of the mask into the environment through an air exhaust filter. In an example, a protective face mask can comprise: a first air impellor (e.g. air impellor, fan, turbine, propeller, pump, and/or blower) located on the back (e.g. on the posterior half) of a person's head or neck which draws air in from the environment through an air intake filter on the front (e.g. on the anterior half) of the person's head into the interior concavity of the mask; and a second air impellor located on the back (e.g. on the posterior half) of a person's head or neck which draws air out from the interior concavity of the mask through an air exhaust filter on the front (e.g. on the anterior half) of the person's head into the environment.

In an example, a protective face mask can comprise: a first air impellor (e.g. air impellor, fan, turbine, propeller, pump, and/or blower) which is located on the right side of the back of a person's head or neck and a second air impellor which is located on the left side of the back of the person's head or neck. In an example, a protective face mask can comprise: a first air impellor (e.g. air impellor, fan, turbine, propeller, pump, and/or blower) which draws air in from the environment through an air intake filter on the front (e.g. the anterior half) of the person's head into the interior concavity of the mask; and a second air impellor which draws air out from the interior concavity of the mask through an air exhaust filter on the front (e.g. the anterior half) of the person's head out into the environment.

In an example, a protective face mask can comprise: two air impellors (e.g. air impellors, fans, turbines, propellers, pumps, and/or blowers) which are located on the back (e.g. on the posterior half) of a person's head or neck, wherein an air intake impellor draws air in from the environment through an air intake filter into the interior concavity of the mask, and wherein an air exhaust impellor draws air out from the interior concavity of the mask through an air exhaust filter out to the environment.

In an example, a protective face mask can have a (concave) transparent portion which covers a person's mouth, wherein the (concave) transparent portion is attached to the person's head by one or more air tubes (or channels), wherein the one or more air tubes (or channels) conduct airflow between the interior of the transparent portion and an air impellor (e.g. air impellor, fan, turbine, propeller, pump, and/or blower) on the back of the person's head or neck. In an example, a protective face mask can have a (concave) transparent portion which covers a person's mouth, wherein the (concave) transparent portion is attached to the person's head by one or more air tubes (or channels).

In an example, a transparent portion of a face mask which covers a person's mouth can have a concave interior. In an example, a concave transparent portion can be a smoothly-arcuate three-dimensional surface. In an example, a concave transparent portion can be a geodesic three-dimensional surface. In an example, a concave transparent portion can be created by assembling a plurality of flat transparent polygonal surfaces. In an example, a concave transparent portion can be created by assembling a plurality of flat transparent hexagonal surfaces. In an example, a concave transparent portion can have a shape which is a section of a sphere or ellipsoid.

In an example, a transparent portion of a front portion of a protective face mask can cover a person's mouth. In an example, a transparent portion of a face mask which covers a person's mouth can have a hexagonal perimeter. In an example, a transparent portion of a face mask which covers a person's mouth can have an octagonal perimeter. In an example, a transparent portion of a face mask which covers a person's mouth can have an egg-shaped perimeter. In an example, a transparent portion of a front portion of a protective face mask can cover a person's mouth, nose, and cheeks.

In an example, a transparent portion of a face mask can have multiple layers. In an example, a transparent portion of a face mask can comprise an inward-facing transparent layer, an outward-facing transparent layer, and an air gap between the inward-facing and outward-facing layer. In an example, there can be (heated or cooled) airflow through the air gap to reduce fogging. In an example, a transparent portion of a face mask can further comprise transparent electroconductive elements through which electrical current is transmitted to reduce fogging.

In an example, a transparent front portion of a protective face mask can cover a person's nose and mouth. In an example, a transparent front portion of a protective face mask can be held on a person's head by (elastic) straps which loop or tie around the person's ears or the back of their head. In an example, a transparent front portion of a protective face mask can be held on a person's head by flexible right-side and left-side air tubes or channels. In an example, a transparent front portion of a protective face mask can be held on a person's head by pleated, reticulated, corrugated, and/or undulating right-side and left-side air tubes or channels.

In an example, an air filter can be a coarse particulate filter. In an example, an air filter can be a High Efficiency Particulate Air (HEPA) filter. In an example, an air filter can be disposable and/or replaceable. In an example, a disposable and/or replaceable air filter can snap, clip, or pop into place. In an example, a disposable and/or replacement air filter cartridge can snap, clip, or pop into in a recess in a face mask. In an example, an air filter can be made from one or more polymers selected from the group consisting of: polytetrafluoroethylene (PTFE), polypropylene (PP), polyester, polyethylene, and polyurethane (PVC). In an example, an air filter can be made from spun material, such as a spun polymer.

In an example, an air filter can have an electrically-charged mesh and/or grid. In an example, an air filter can have electrically-charged fibers. In an example, an air filter can include gold nanoparticles. In an example, an air filter can comprise multiple layers with different pore sizes and/or filtration mechanisms. In an example, an air filter can have salt crystals. In an example, an air filter can have convoluted, undulating, and/or sinusoidal air pathways.

In an example, an air filter can have two or more layers (configured in series) which filter different size particles or filter particles via different methodologies. In an example, an air filter can have a first layer which mechanically filters coarse (larger size) particles and a second layer which mechanically filters fine (smaller size particles). In an example, an air filter can have a first layer which filters particles mechanically and a second layer which mechanically filters particles with an electrostatic mesh or grid. In an example, an air filter can have a first layer which filters particles mechanically and a second layer which sanitizes airflow using an antimicrobial substance. In an example, an air filter can have a first layer which filters particles mechanically and a second layer which sanitizes airflow using heat. In an example, an air filter can have a first layer which filters particles mechanically and a second layer which sanitizes airflow using ultraviolet light.

In an example, an air impellor can be located on the back of a person's head, wherein a first horizontal plane spans the center of the air impellor (when the person is holding their head upright), wherein a second horizontal plane spans the centers of the person's auricles (when the person is holding their head upright), and wherein the second horizontal plane is higher than the first horizontal plane. In an example, an air impellor can be located on the back of a person's head, wherein a first horizontal plane spans the center of the air impellor (when the person is holding their head upright), wherein a second horizontal plane spans the centers of the person's auricles (when the person is holding their head upright), and wherein the second horizontal plane is 1" to 3" higher than the first horizontal plane.

In an example, an air impellor can be located on the back of a person's head, wherein a first horizontal plane spans the center of the air impellor (when the person is holding their head upright), wherein a second horizontal plane spans the centers of the person's auricles (when the person is holding their head upright), and wherein the second horizontal plane is 2" to 6" higher than the first horizontal plane.

In an example, an air intake filter can be located on a person's cheek. In an example, an air intake filter can be located on a person's right cheek and an air exhaust filter can be located on a person's left cheek, or vice versa. In an example, an air intake port can be located above a person's mouth and/or below the person's nose and an air exhaust port can be located below a person's mouth and/or on the person's chin, or vice versa. In an example, an air intake port can be located above a person's mouth and/or below the person's nose. In an example, an air intake port can be located below a person's mouth and/or on the person's chin and an air exhaust port can be located above a person's mouth and/or below the person's nose, or vice versa.

In an example, an air tube (or channel) between a transparent portion of a face mask and an air impellor (e.g. air impellor, fan, turbine, propeller, pump, and/or blower) on the back of a person's head can be substantially horizontal (when the person is holding their head upright), except for a conic-section-shaped undulation which curves over and around the person's ear. In an example, an air tube (or channel) between a transparent portion of a face mask and an air impellor on the back of a person's head can be substantially parallel to a virtual plane between the upper half of the person's head and the bottom half of the person's head, except for a conic-section-shaped undulation which curves over and around the person's ear.

In an example, an air tube or channel can be between an air intake filter on a front portion of a face mask and an air impellor (e.g. air impellor, fan, turbine, propeller, pump, and/or blower) on the back of a person's head or neck. In an example, this air tube or channel can be inside a strap, wherein the strap attaches the front of the face mask to the person's head. In an example, this strap can be made from elastic fabric. In an example, a strap which attaches the front of a face mask to a person's head can have an inner layer which is impermeable to air, wherein this inner layer forms an air channel that conducts air between mask components (such as an air impellor) on the back of the person's head and mask components (such as an air intake port) on the front of the person's head. In an example, an air tube (or channel) between a transparent portion on the front of a face mask and an air impellor on the back of a person's head can be inside a strap which attaches the front of the face mask to the person's head.

In an example, an air tube (or channel) can conduct air from the front of a face mask to an impellor on the back of the person's head or neck, or vice versa. In an example, "tube maximum height" can be defined as the height of the highest horizontal plane to which the highest portion of the tube reaches (when a person is holding their head upright). In an example, "tube minimum height" can be defined as the height of the lowest horizontal plane to which the lowest portion of the tube reaches (when a person is holding their head upright). In an example, "auricle height" can be defined as the height of the horizontal plane which spans the centers of a person's auricles (when a person is holding their head upright).

In an example, tube maximum height can be ¼" to 1" above auricle height. In an example, tube maximum height can be ½" to 3" above auricle height. In an example, tube maximum height can be ¼" to 1" below auricle height. In an example, tube minimum height can be ¼" to 4" below auricle height. In an example, tube minimum height can be ½" to 6" below auricle height. In an example, tube minimum height can be ¼" to 4" below auricle height.

In an example, an air tube (or channel) can span (at least a portion of) the perimeter of a transparent portion of a face mask which covers a person's mouth. In an example, an air tube (or channel) which conducts air between an air intake port and an air impellor (e.g. air impellor, fan, turbine, propeller, pump, and/or blower) can have an inner diameter within the range of ⅛" to ¼". In an example, an air tube (or channel) which conducts air between an air intake port and an air impellor (e.g. air impellor, fan, turbine, propeller, pump, and/or blower) can have an inner diameter within the range of ⅛" to ½". In an example, an air tube (or channel) which conducts air between an air intake port and an air impellor (e.g. air impellor, fan, turbine, propeller, pump, and/or blower) can have an inner diameter within the range of ¼" to ½".

In an example, an air tube (or channel) which conducts air between a transparent portion of a mask (which covers a person's mouth) and an air impellor (e.g. air impellor, fan, turbine, propeller, pump, and/or blower) can have an inner diameter within the range of ⅛" to ¼". In an example, an air tube (or channel) which conducts air between a transparent portion of a mask (which covers a person's mouth) and an air impellor (e.g. air impellor, fan, turbine, propeller, pump, and/or blower) can have an inner diameter within the range of ⅛" to ½". In an example, an air tube (or channel) which conducts air between a transparent portion of a mask (which covers a person's mouth) and an air impellor (e.g. air impellor, fan, turbine, propeller, pump, and/or blower) can have an inner diameter within the range of ¼" to ½".

In an example, an air tube (or channel) which conveys airflow between an air impellor (e.g. air impellor, fan, turbine, propeller, pump, and/or blower) on the back of a person's head or neck and a transparent portion of a mask which covers the person's mouth can span the side of the person's head around the person's ear. In an example, an air tube or channel can be reticulated. In an example, an air tube or channel can be pleated. In an example, an air tube or channel can be corrugated. In an example, an air tube or channel can be undulating. In an example, an air tube or channel can be convoluted.

In an example, a face mask can comprise two air filters which are in fluid communication with each other and in configured in series, wherein air flows first through a first air filter and then through a second air filter. In an example, a first air filter can have a first porosity level, a second air filter configured in series with the first air filter can have a second porosity level, and the second level can be greater than the first level. In an example, a first air filter can have a first pore size, a second air filter configured in series with the first air filter can have a second pore size, and the second size can be greater than the first size.

In an example, a face mask can comprise: a concave transparent portion which covers a person's mouth; a first air filter which is in fluid communication with a concave interior of the transparent portion; a second air filter which is in fluid communication with the concave interior of the transparent portion; an environmental or biometric sensor; and an air impellor which is in fluid communication with the second air filter, wherein the air impellor is turned off (or decreased in speed) when analysis of data from the environmental sensor detects an environmental hazard and/or is turned on (or increased in speed) when analysis of data from biometric sensor indicates that the person's needs more airflow (e.g. more oxygen and/or less carbon dioxide).

In an example, a face mask can further comprise a microphone which is in sonic communication with a concave interior of a transparent portion of the mask. In an example, a face mask can further comprise a speaker on the front of the mask. In an example, a face mask can have an ambient light sensor. In an example, a face mask can have a light on the interior of the mask which illuminates the wearer's mouth to further enhance visibility. In an example, a face mask can further comprise a collar component which is worn around a person's neck. In an example, an air impellor can be located on a collar on the back of the person's neck.

In an example, a face mask can further comprise one or more electric motors which rotate one or more air impellors. In an example, a face mask can further comprise a battery or other energy storage component. In an example, a face mask can harvest and store electrical energy from the rotation of an impellor (e.g. air impellor, fan, turbine, propeller, pump, and/or blower) due to air flow from a person's exhalation or inhalation. In an example, a face mask can further comprise a data processing unit. In an example, a face mask can further comprise a wireless data transmitter and/or receiver.

In an example, a first air filter can have an electrostatic charge, a second air filter configured in parallel with the first air filter can have a second electrostatic charge, and the second charge can be greater than the first charge. In an example, a first air filter can have a first depth, a second air filter configured in parallel with the first air filter can have a second depth, and the second depth can be greater than the first depth. In an example, a first air filter can have a first width, a second air filter configured in parallel with the first air filter can have a second width, and the second width can be greater than the first width. In an example, a first air filter can have a first shape, a second air filter configured in parallel with the first air filter can have a second shape, and the second shape can be different than the first shape.

In an example, a protective face mask can comprise: a concave transparent portion which covers a person's mouth; an air intake filter within 4" of the concave transparent portion; an air exhaust filter within 4" of the concave transparent portion; an air impellor (e.g. air impellor, fan, turbine, propeller, pump, and/or blower) located on the back of the person's head or neck; a first air tube (or channel) which loops above an ear and conducts air between the air intake filter and the air impellor; and a second air tube (or channel) which loops above an ear and conducts air between the air impellor and a concave interior of the transparent portion.

In an example, a protective face mask can comprise: a concave transparent portion which covers a person's mouth; a first air filter within 4" of the concave transparent portion; and a second air filter within 4" of the concave transparent portion. In an example, a protective face mask can comprise: a concave transparent portion which covers a person's mouth; a first air filter within 4" of the concave transparent portion; a first one-way valve which regulates the direction of airflow through the first air filter; a second air filter within 4" of the concave transparent portion; and a second one-way valve which regulates the direction of airflow through the second air filter.

In an example, a protective face mask can comprise: a concave transparent portion which covers a person's mouth; a first air filter around a first percentage of the perimeter of the concave transparent portion, wherein the first portion is between 25% and 50%; and a second air filter around a second percentage of the perimeter of the concave transparent portion, wherein the second portion is between 25% and 50%. In an example, a protective face mask can comprise: a concave transparent portion which covers a person's mouth; a first air filter around a first percentage of the perimeter of the concave transparent portion, wherein the first portion is between 25% and 50%; and a second air filter around a second percentage of the perimeter of the concave transparent portion, wherein the second portion is between 50% and 75%.

In an example, a protective face mask can comprise: a concave transparent portion which covers a person's mouth; an air intake filter within 4" of the concave transparent portion; an air exhaust filter within 4" of the concave transparent portion; one or more air impellors (e.g. air impellors, fans, turbines, propellers, pumps, and/or blowers) located on the back of the person's head or neck; one or more air tubes (or channels) which conduct air from the air intake filter to the one or more air impellors; and one or more air tubes (or channels) which conduct air from the one or more air impellors to a concave interior of the transparent portion.

In an example, a protective face mask can comprise: a concave transparent portion which covers a person's mouth; an air intake port within 4" of the concave transparent portion; an air exhaust port within 4" of the concave transparent portion; an air impellor (e.g. air impellor, fan, turbine, propeller, pump, and/or blower) located on the back of the person's head or neck; a first air tube (or channel) which loops below an ear and conducts air from the air intake port to the air impellor; a second air tube (or channel) which loops below an ear and conducts air from the air impellor to a concave interior of the transparent portion; an air intake filter that filters airflow between the air intake port and the air impellor; and an air exhaust filter that filters air which then flows out from the air exhaust port.

In an example, (radial) o'clock positions can be defined around the perimeter of a transparent portion of a face mask, wherein the 12 o'clock position is centrally located under a person's nose, the 6 o'clock position is centrally located under the person's mouth. In an example, an air port can span the perimeter of a transparent portion of a face mask entirely between the 7 o'clock to 11 o'clock positions. In an example, the ends of an air port can be at the 7 o'clock position and the 11 o'clock position. In an example, an air port can span the perimeter of a transparent portion of a face mask entirely between 1 o'clock to 5 o'clock positions. In an example, the ends of an air port can be at the 1 o'clock position and the 5 o'clock position.

In an example, an air intake port can span the perimeter of a transparent portion of a face mask between the 7 o'clock and 11 o'clock positions and an air exhaust port can span between the 1 o'clock and 5 o'clock positions around the perimeter of a transparent portion of a mask, or vice versa. In an example, an air intake port can span the perimeter of a transparent portion of a face mask between the 10 o'clock and 2 o'clock positions and an air exhaust port can span between the 4 o'clock and 8 o'clock positions around the perimeter of a transparent portion of a mask, or vice versa.

In an example, a protective face mask can comprise: a concave transparent portion which covers a person's mouth; an air intake port on the concave transparent portion; an air exhaust port on the concave transparent portion; an air impellor (e.g. air impellor, fan, turbine, propeller, pump, and/or blower) located on the back of the person's head or neck; a first air tube (or channel) which conducts air from the air intake port to the air impellor; and a second air tube (or channel) which conducts air from the air impellor to a concave interior of the transparent portion. In an example, the first air tube (or channel) can be on one side (e.g. the right side) of the person's head and the second air tube (or channel) can be on the opposite side (e.g. the left side) of the person's head. Alternatively, the first and second air tubes (or channels) can both be on the same (e.g. right or left) side of the person's head.

In an example, a protective face mask can comprise: a concave transparent portion which covers a person's mouth; an air intake port within 4" of the concave transparent portion; an air exhaust port within 4" of the concave transparent portion; an air impellor (e.g. air impellor, fan, turbine, propeller, pump, and/or blower) located on the back of the person's head or neck; a first air tube (or channel) which loops below an ear and conducts air from the air intake port to the air impellor; and a second air tube (or channel) which loops below an ear and conducts air from the air impellor to a concave interior of the transparent portion.

In an example, a protective face mask can comprise: a concave transparent portion which covers a person's mouth; an air intake port to one side (e.g. to the right) of the concave transparent portion; an air exhaust port to the other side (e.g. to the left) of the concave transparent portion; an air impellor (e.g. air impellor, fan, turbine, propeller, pump, and/or blower) located on the back of the person's head or neck; a first air tube (or channel) which conducts air from the air intake port to the air impellor; a second air tube (or channel)

which conducts air from the air impellor to a concave interior of the transparent portion; an air intake filter that filters airflow between the air intake port and the air impellor; and an air exhaust filter that filters air which then flows out from the air exhaust port.

In an example, a protective face mask can comprise: a concave transparent portion which covers a person's mouth; an air intake port along a perimeter of the concave transparent portion; an air exhaust port along the perimeter of the concave transparent portion; an air impellor (e.g. air impellor, fan, turbine, propeller, pump, and/or blower) located on the back of the person's head or neck; a first air tube (or channel) which conducts air from the air intake port to the air impellor; and a second air tube (or channel) which conducts air from the air impellor to a concave interior of the transparent portion.

In an example, a protective face mask can comprise: a face mask worn by a person; wherein the face mask further comprises a concave transparent portion which covers the person's mouth; wherein the face mask further comprises an air intake port within 4" of the transparent portion, wherein air from the environment enters the air intake port; wherein the face mask further comprises an air intake filter within 4" of the transparent portion, wherein air from the air intake port enters the air intake filter; wherein the face mask further comprises a first air tube (e.g. air tube or channel), wherein air from the air intake filter enters the first air tube; wherein the face mask further comprises one or more air impellors (e.g. air impellors, fans, turbines, propellers, pumps, and/or blowers) on the back on the person's head or neck, wherein air from the first air tube enters the one or more air impellors; wherein the face mask further comprises a second air tube (e.g. air tube or channel), wherein air from the one or more air impellors enters the second air tube, and wherein air from the second air tube enters the concave interior of the transparent portion; wherein the face mask further comprises an air outflow filter on a front portion of the face mask, wherein air from the concave interior of the transparent portion enters the air outflow filter; and wherein the face mask further comprises an air exhaust port within 4" of the transparent portion; wherein air from air outflow filter enters the air outflow port, and wherein air from the air exhaust port is exhausted out into the environment.

In an example, a protective face mask can comprise: a first air impellor (e.g. air impellor, fan, turbine, propeller, pump, and/or blower) located on the back (e.g. on the posterior half) of a person's head or neck which draws air in from the environment into the interior concavity of the mask through an air intake filter on a first side (e.g. right or left) of the person's head; and a second air impellor located on the back (e.g. on the posterior half) of a person's head or neck which draws air out from the interior concavity of the mask out to the environment through an air exhaust filter on an opposite side (e.g. left or right) of the person's head.

In an example, a protective face mask can comprise: a first air impellor (e.g. air impellor, fan, turbine, propeller, pump, and/or blower) located on the back (e.g. on the posterior half) of a person's head or neck which draws air in from the environment through an air intake filter on the front of the mask into the interior concavity of the mask; and a second air impellor located on the back (e.g. on the posterior half) of a person's head or neck which draws air out from the interior concavity of the mask through an air exhaust filter on the front of the mask out to the environment. In an example, a protective face mask can comprise: a first air impellor (e.g. air impellor, fan, turbine, propeller, pump, and/or blower) located on the right side of a person's head or neck which draws air in from the environment into the interior concavity of the mask through an air intake filter on the right side of the person's head; and a second air impellor located on the left side of a person's head or neck which draws air out from the interior concavity of the mask out to the environment through an air exhaust filter on a the left side of the person's head.

In an example, a protective face mask can comprise: a transparent portion which covers a person's mouth; an air impellor (e.g. air impellor, fan, turbine, propeller, pump, and/or blower) located on the back of the person's head or neck; a right-side air tube (or channel) which conveys airflow between the transparent portion and the air impellor, spanning a right side of the person's head above and/or around the person's right ear; and a left-side air tube (or channel) which conveys airflow between the transparent portion and the air impellor, spanning a left side of the person's head above and/or around the person's left ear.

In an example, a protective face mask can have a (concave) transparent portion which covers a person's mouth, wherein the (concave) transparent portion is attached to the person's head by one or more elastic straps. In an example, a transparent front portion of a protective face mask can be held on a person's head by flexible right-side and left-side air tubes (or channels) which span the right side and the left side, respectively, of the person's head and connect to an air impellor (e.g. air impellor, fan, turbine, propeller, pump, and/or blower) on the back of the person's head or neck.

In an example, a transparent front portion of a protective face mask can be held on a person's head by flexible right-side and left-side air tubes (or channels) which span the right side and the left side of the person's head, above the person's right and left ears, respectively, and connect to an air impellor (e.g. air impellor, fan, turbine, propeller, pump, and/or blower) on the back of the person's head or neck.

In an example, a transparent front portion of a protective face mask can be held on a person's head by straps and/or air tubes which loop around the person's ears. In an example, a transparent front portion of a protective face mask can be held on a person's head by straps and/or air tubes which loop over the person's ears. In an example, a transparent front portion of a protective face mask can be held on a person's head by straps and/or air tubes which pass under the person's ears. In an example, a transparent front portion of a protective face mask can be held on a person's head by straps and/or air tubes which loop around the person's head.

In an example, a protective face mask can have one or more air tubes (or channels) between an air intake port on the front portion of the mask and an air impellor (e.g. air impellor, fan, turbine, propeller, pump, and/or blower) on a rear portion of the mask. In an example, a protective face mask can have one or more air tubes (or channels) between a front portion of the mask and an air impellor (e.g. air impellor, fan, turbine, propeller, pump, and/or blower) on a rear portion of the mask. In an example, a protective face mask can have one or more air tubes (or channels) between a transparent portion of a front portion of the mask and an air impellor (e.g. air impellor, fan, turbine, propeller, pump, and/or blower) on a rear portion of the mask.

In an example, a transparent portion of a front portion of a protective face mask can cover a person's mouth. In an example, a transparent portion of a mask can cover a person's mouth, nose, and cheeks. In an example, a transparent portion of a mask can cover a person's mouth. In an example, an air exhaust filter can be located above a person's mouth and/or below the person's nose. In an example, an air exhaust filter can be located below a person's mouth and/or on the person's chin. In an example, an air exhaust filter can be located on a person's cheek.

In an example, an air filter can be made from woven or knitted material. In an example, an air filter can be made with nonwoven and/or melt-blown materials, such as a melt-blown polymer. In an example, an air filter can be made with closed-cell foam. In an example, an air filter can be made with open-cell foam. In an example, an air filter can have one or more reticulated layers. In an example, an air filter can have an elongated and/or tapered shape. In an example, an air filter can have a convoluted, undulating, and/or sinusoidal shape. In an example, the amplitude or frequency of undulations in an air filtration pathway can be automatically increased in response to detection of an environmental hazard.

In an example, an air filter can be made with carbon material, such as carbon nanotubes or activated carbon. In an example, an air filter can be made with cellulose. In an example, an air filter can be made with copper, such as copper nanoparticles or copper iodide particles. In an example, an air filter can further comprise zinc alloy and/or nanoparticles. In an example, an air filter can include silver material. In an example, an air filter can include electrostatic attraction and/or precipitation. In an example, an air filter can include ionizing sanitization. In an example, an air filter can include metal oxide particles.

In an example, an air impellor can have a rotating member which rotates around an axle. In an example, an air impellor can have a rotating member which rotates around an axle which is generally parallel to the direction of airflow through the impellor. In an example, an air impellor can comprise a rotating member which rotates around an axle which is generally orthogonal (or perpendicular) to the direction of airflow through the impellor (such as with a paddle wheel design).

In an example, an air intake port can be located below a person's mouth and/or on the person's chin. In an example, an air intake port can be located on a person's cheek. In an example, an air intake port can be located on a person's right cheek and an air exhaust port can be located on a person's left cheek, or vice versa. In an example, an air tube (or channel) can have a plurality of holes which are in fluid communication with the interior of a (transparent) front portion of a protective face mask. In an example, an air tube (or channel) can span (at least a portion of) the perimeter of a transparent portion of a face mask which covers a person's mouth, wherein there are a plurality of holes in the air tube (or channel) which deliver air to different locations in the interior of the transparent portion.

In an example, an air tube or channel between a transparent portion of a face mask and an air impellor (e.g. air impellor, fan, turbine, propeller, pump, and/or blower) on the back of a person's head can include an arcuate loop around and over a person's ear, wherein the arcuate loop has a conic section shape. In an example, an air tube or channel between a transparent portion of a face mask which covers a person's mouth and an air impellor on the back of the person's head can have an undulating and/or sinusoidal shape.

In an example, an air tube (or channel) between an air intake port on a front part of a face mask and an air impellor (e.g. air impellor, fan, turbine, propeller, pump, and/or blower) on the back of a person's head or neck can have longitudinal variation in size (e.g. diameter). In an example, the size (e.g. diameter) of such an air tube (or channel) can decrease as it spans from the front part of the face mask to the air impellor. Alternatively, the size (e.g. diameter) of such an air tube (or channel) can increase as it spans from the front part of the face mask to the air impellor. In an example, there can be longitudinal variation in the durometer of an air tube (or channel). In an example, some longitudinal portions of the air tube (or channel) can be more compressible and/or flexible than other longitudinal portions.

In an example, an air tube (or channel) can have a circular or elliptical cross-sectional shape. In an example, an air tube (or channel) can be a polymer tube. In an example, an air tube (or channel) can be pleated. In an example, an air tube (or channel) can be reticulated. In an example, an air tube (or channel) can be undulating and/or sinusoidal. In an example, an air tube (or channel) can be a fabric channel. In an example, an air tube (or channel) can be inside an elastic strap. In an example, an air tube (or channel) itself can be elastic and/or stretchable.

In an example, an air tube (or channel) on which conducts air between the front of a face mask and an air impellor (e.g. air impellor, fan, turbine, propeller, pump, and/or blower) on the back of a person's head or neck can have a first diameter, the impellor can have a second diameter, and the second diameter can be least 2 times the size of the first diameter. In an example, an air tube (or channel) on which conducts air between the front of a face mask and an air impellor on the back of a person's head or neck can have a first diameter, the impellor can have a second diameter, and the second diameter can be between 2 and 5 times the size of the first diameter. In an example, an air tube (or channel) on which conducts air between the front of a face mask and an air impellor can have a first diameter, the impellor can have a second diameter, and the second diameter can be between 90% and 110% of the size of the first diameter.

In an example, an air tube (or channel) which conveys airflow between an air impellor (e.g. air impellor, fan, turbine, propeller, pump, and/or blower) on the back of a person's head or neck and a transparent portion of a mask which covers the person's mouth can span the side of the person's head above the person's ear. In an example, an air tube (or channel) which conveys airflow between an air impellor (e.g. air impellor, fan, turbine, propeller, pump, and/or blower) on the back of a person's head or neck and a transparent portion of a mask which covers the person's mouth can span the side of the person's head below the person's ear.

In an example, an elastic strap can contain, enclose, and/or cover a reticulated and/or undulating air tube, wherein pleats and/or undulations in the air tube enable it to expand or contract as the elastic strap expands or contracts. In an example, the diameter of an air tube (or channel) inside an elastic strap can be between 25% and 75% of the width of the elastic strap. In an example, an air tube (or channel) can be concentric with an elastic strap. In an example, an elastic strap which attaches a front portion of a face mask to a person's head can have a coaxial structure with an air-permeable outer layer and an air impermeable inner layer, wherein air is conducted through a lumen defined by the inner layer.

In an example, a face mask can comprise two air filters which are in fluid communication with each other and configured in parallel, wherein air flows first through a first air filter only or through a second air filter only. In an example, a first air filter can have a first porosity level, a second air filter configured in parallel with the first air filter can have a second porosity level, and the second level can be greater than the first level. In an example, a first air filter can have a first pore size, a second air filter configured in parallel with the first air filter can have a second pore size, and the second size can be greater than the first size. In an example, opening or closing one or more air valves determines whether air flows through only the first air filter, only the second air filter, or both air filters.

In an example, a face mask can comprise: a first air filter and a second air filter; and one or more air valves; wherein the first and second air filters have a series configuration (wherein air flows through the first air filter and then through the second air filter) and a parallel configuration (wherein air can flow through first air filter only or through the second air filter only), and wherein the air filters can be changed from their first configuration to their second configuration, or vice versa, by opening or closing the one or more air valves.

In an example, a face mask can further comprise a respiration sensor. In an example, a face mask can further comprise a sound sensor and/or microphone. In an example, a face mask can further comprise a spectroscopic sensor. In an example, a face mask can further comprise a temperature sensor. In an example, a face mask can further comprise an air flow sensor. In an example, a face mask can further comprise an air pressure sensor. In an example, an air pressure sensor can measure air pressure within a mask. In an example, a face mask can further comprise an air quality sensor which monitors one or more of the following: air borne pollution, chemicals, dust, gas, and pathogens.

In an example, a face mask can include an air impellor. In an example, the speed and/or volume of air flow through this impellor can be automatically changed based on analysis of data from one or more environmental sensors or biometric sensors which are also part of the mask. In an example, air flow speed can be changed by changing the rotational speed of the impellor. In an example, the rotational speed of an impellor can be automatically changed based on analysis of data from one or more environmental sensors or biometric sensors which are part of the mask. In an example, airflow can be increased or decreased when an environmental sensor indicates an environmental hazard. In an example, airflow can be increased when a biometric sensor indicates that the wearer has a greater need for oxygen. In an example, the direction of airflow through an impellor can be automatically change based on analysis of data from one or more environmental sensors or biometric sensors.

In an example, a front part of a face mask can be held on a person's head by right-side and left-side adjustable and/or elastic straps, wherein each of the straps contains an elastic, undulating, sinusoidal, and/or elastic air tube or channel. In an example, a front part of a face mask can be held on a person's head by right-side and left-side adjustable and/or elastic straps, wherein each of the straps loops around an ear and contains an elastic, undulating, sinusoidal, and/or elastic air tube or channel. In an example, a front part of a face mask can be held on a person's head by right-side and left-side adjustable and/or elastic straps which loop around the back of the person's head or neck, wherein each of the straps contains an elastic, undulating, sinusoidal, and/or elastic air tube or channel.

In an example, a protective face mask can comprise: a concave transparent portion which covers a person's mouth; an air intake filter within 4" of the concave transparent portion; an air exhaust filter within 4" of the concave transparent portion; an air impellor (e.g. air impellor, fan, turbine, propeller, pump, and/or blower) located on the back of the person's head or neck; a first air tube (or channel) which loops below an ear and conducts air between the air intake filter and the air impellor; and a second air tube (or channel) which loops below an ear and conducts air between the air impellor and a concave interior of the transparent portion.

In an example, a protective face mask can comprise: a concave transparent portion which covers a person's mouth; an air intake port; an air intake filter; a first air tube or channel; an air impellor (e.g. air impellor, fan, turbine, propeller, pump, and/or blower); a second air tube or channel; an air exhaust filter; and an air exhaust port; wherein the first air tube or channel conducts air from the air intake filter to the air impellor; wherein the length of the first air tube or channel is at least 5"; wherein the second air tube or channel conducts air from the air impellor to a concave interior of the transparent portion; and wherein the length of the second air tube or channel is at least 5".

In an example, a protective face mask can comprise: a concave transparent portion which covers a person's mouth; an air intake port; an air intake filter; a first air tube or channel; an air impellor (e.g. air impellor, fan, turbine, propeller, pump, and/or blower); a second air tube or channel; an air exhaust filter; and an air exhaust port; wherein the first air tube or channel conducts air from the air intake filter to the air impellor; wherein the length of the first air tube or channel is at least 8"; wherein the second air tube or channel conducts air from the air impellor to a concave interior of the transparent portion; and wherein the length of the second air tube or channel is at least 8".

In an example, a protective face mask can comprise: a face mask; wherein the face mask further comprises a concave transparent portion which covers a person's mouth; wherein the face mask further comprises an air intake port within 4" of the transparent portion; wherein the face mask further comprises an air intake filter within 4" of the transparent portion; wherein the face mask further comprises an air impellor (e.g. air impellor, fan, turbine, propeller, pump, and/or blower) located on the back of the person's head or neck; wherein the face mask further comprises a first air tube or channel which conducts air from the air intake filter to the air impellor, wherein the first air tube or channel is at least 5" long; wherein the face mask further comprises a second air tube or channel which conducts air from the air impellor to a concave interior of the transparent portion, wherein the second air tube or channel is at least 5" long; an air exhaust filter; and an air exhaust port.

In an example, an air tube or channel which conducts air from an air intake filter to an air impellor can be at least 5" long. In an example, an air tube or channel which conducts air from an air intake filter to an air impellor can be at least 8" long. In an example, an air tube or channel which conducts air from an air intake filter to an air impellor can be between 5" and 15" long. In an example, an air tube or channel which conducts air from an air impeller to a transparent portion of a face mask can be at least 5" long. In an example, an air tube or channel which conducts air from an air impeller to a transparent portion of a face mask can be at least 8" long. In an example, an air tube or channel which conducts air from an air impeller to a transparent portion of a face mask can between 5" and 15" long.

In an example, a protective face mask can comprise: a concave transparent portion which covers a person's mouth; a first air filter around a first portion of the perimeter of the concave transparent portion; a first one-way valve which regulates the direction of airflow through the first air filter; a second air filter around a second portion of the perimeter of the concave transparent portion; and a second one-way valve which regulates the direction of airflow through the second air filter.

In an example, a protective face mask can comprise: a concave transparent portion which covers a person's mouth; a first conic-section-shaped air filter which is in fluid communication with a concave interior of the transparent portion; and a second conic-section-shaped air filter which is in fluid communication with the concave interior of the transparent portion. In an example, an air filter which is in fluid communication with a concave interior of a transparent portion of a face mask can have a circular or elliptical shape. In an example, an air filter which is in fluid communication with a concave interior of a transparent portion of a face mask can have a conic section shape. In an example, an air filter which is in fluid communication with a concave interior of a transparent portion of a face mask can span between 25% and 50% of the perimeter of the transparent portion.

In an example, a perimeter of a face mask which comes into contact with a person's face can be inflated to create a soft, but close-fitting, seal between the mask and the person's face. In an example, the perimeter of a face mask which comes into contact with a person's face can comprise a plurality of inflatable segments. In an example, different inflatable segments around the mask perimeter can be individually and selectively inflated (to different extents and/or pressure levels) in order to best conform to the contour of a person's face.

In an example, a protective face mask can comprise: a concave transparent portion which covers a person's mouth; an air intake filter on a first portion of the perimeter of the concave transparent portion; an air exhaust filter on a second portion of the perimeter of the concave transparent portion; one or more air impellors (e.g. air impellors, fans, turbines, propellers, pumps, and/or blowers) located on the back of the person's head or neck; one or more air tubes (or channels) which conduct air from the air intake filter to the one or more air impellors; and one or more air tubes (or channels) which conduct air from the one or more air impellors to a concave interior of the transparent portion.

In an example, a protective face mask can comprise: a concave transparent portion which covers a person's mouth; a first air tube (or channel) which attaches (a side of) the transparent portion to the person's head; a second air tube (or channel) which attaches (a side of) the transparent portion to the person's head; an air intake port within 4" of the transparent portion; an air exhaust port within 4" of the transparent portion; an air impellor (e.g. air impellor, fan, turbine, propeller, pump, and/or blower) on the back of the person's head or neck; wherein the first air tube (or channel) conducts air from the air intake port to the air impellor; and wherein the second air tube (or channel) conducts air from the air impellor to the concave interior of the transparent portion.

In an example, a protective face mask can comprise: a concave transparent portion which covers a person's mouth; an air intake port within 4" of the concave transparent portion; an air exhaust port within 4" of the concave transparent portion; an air impellor (e.g. air impellor, fan, turbine, propeller, pump, and/or blower) located on the back of the person's head or neck; a first air tube (or channel) which conducts air from the air intake port to the air impellor; and a second air tube (or channel) which conducts air from the air impellor to a concave interior of the transparent portion, wherein there are holes in the second air tube which are in fluid communication with the concave interior of the transparent portion.

In an example, a protective face mask can comprise: a concave transparent portion which covers a person's mouth; an air intake port on the concave transparent portion; an air exhaust port on the concave transparent portion; an air impellor (e.g. air impellor, fan, turbine, propeller, pump, and/or blower) located on the back of the person's head or neck; a first air tube (or channel) which conducts air from the air intake port to the air impellor; a second air tube (or channel) which conducts air from the air impellor (e.g. air impellor, fan, turbine, propeller, pump, and/or blower) to a concave interior of the transparent portion; an air intake filter that filters airflow between the air intake port and the air impellor; and an air exhaust filter that filters air between the concave interior of the transparent portion and the air exhaust port.

In an example, a protective face mask can comprise: a concave transparent portion which covers a person's mouth; an air intake port within 4" of the concave transparent portion; an air exhaust port within 4" of the concave transparent portion; an air impellor (e.g. air impellor, fan, turbine, propeller, pump, and/or blower) located on the back of the person's head or neck; a first air tube (or channel) which loops above an ear and conducts air from the air intake port to the air impellor; a second air tube (or channel) which loops above an ear and conducts air from the air impellor to a concave interior of the transparent portion; an air intake filter that filters airflow between the air intake port and the air impellor; and an air exhaust filter that filters air which then flows out from the air exhaust port.

In an example, a protective face mask can comprise: a concave transparent portion which covers a person's mouth; an air intake port within 4" of the concave transparent portion; an air exhaust port within 4" of the concave transparent portion; an air impellor (e.g. air impellor, fan, turbine, propeller, pump, and/or blower) located on the back of the person's head or neck; a first air tube (or channel) which conducts air from the air intake port to the air impellor; and a second air tube (or channel) which conducts air from the air impellor to a concave interior of the transparent portion.

In an example, a protective face mask can comprise: a concave transparent portion which covers a person's mouth; an air intake port along a perimeter of the concave transparent portion; an air exhaust port along the perimeter of the concave transparent portion; an air impellor (e.g. air impellor, fan, turbine, propeller, pump, and/or blower) located on the back of the person's head or neck; a first air tube (or channel) which conducts air from the air intake port to the air impellor; a second air tube (or channel) which conducts air from the air impellor to a concave interior of the transparent portion; an air intake filter that filters airflow between the air intake port and the air impellor; and an air exhaust filter which filters airflow between the transparent portion and the air exhaust port.

In an example, a protective face mask can comprise: a face mask worn by a person; wherein the face mask further comprises a concave transparent portion which covers the person's mouth; wherein the face mask further comprises an air intake port within 4" of the transparent portion, wherein air from the environment enters the air intake port; wherein the face mask further comprises an air intake filter within 4" of the transparent portion, wherein air from the air intake port enters the air intake filter; wherein the face mask further comprises a right-side air tube (e.g. air tube or channel), wherein air from the air intake filter enters the right-side air tube; wherein the face mask further comprises one or more air impellors (e.g. air impellors, fans, turbines, propellers, pumps, and/or blowers) on the back on the person's head or neck, wherein air from the right-side air tube enters the one or more air impellors; wherein the face mask further comprises a left-side air tube (e.g. air tube or channel), wherein air from the one or more air impellors enters the left-side air tube, and wherein air from the left-side air tube enters the concave interior of the transparent portion; wherein the face mask further comprises an air outflow filter on a front portion of the face mask, wherein air from the concave interior of the transparent portion enters the air outflow filter; and wherein the face mask further comprises an air exhaust port within 4" of the transparent portion; wherein air from air outflow filter enters the air outflow port, and wherein air from the air exhaust port is exhausted out into the environment.

In an example, a protective face mask can comprise: a first air impellor (e.g. air impellor, fan, turbine, propeller, pump, and/or blower) located on the back (e.g. on the posterior half) of a person's head or neck which draws air in from the environment into the interior concavity of the mask through a first air filter; and a second air impellor located on the back (e.g. on the posterior half) of a person's head or neck which draws air out from the interior concavity of the mask into the environment through a second air filter. In an example, a protective face mask can comprise: a first air impellor (e.g. air impellor, fan, turbine, propeller, pump, and/or blower) which draws air in from the environment through an air intake filter on the front of the mask into the interior concavity of the mask; and a second air impellor which draws air out from the interior concavity of the mask through an air exhaust filter on the front of the mask into the environment.

In an example, a protective face mask can comprise: a first air impellor (e.g. air impellor, fan, turbine, propeller, pump, and/or blower) which draws air in from the environment into the interior concavity of the mask through an air filter; and a second air impellor which draws air out from the interior concavity of the mask into the environment through an air filter. In an example, a protective face mask can comprise: a first air impellor (e.g. air impellor, fan, turbine, propeller, pump, and/or blower) which draws air in from the environment through an air intake filter into the interior concavity of the mask; and a second air impellor which draws air out from the interior concavity of the mask through an air exhaust filter into to the environment.

In an example, a protective face mask can have one or more air tubes (or channels) between an air filter on the front portion of the mask and an air impellor (e.g. air impellor, fan, turbine, propeller, pump, and/or blower) on a rear portion of the mask. In an example, a protective face mask can have: a first air tube (or channel) between an air intake port on a front portion of the mask and an air impellor on the back of the person's head or neck; and a second air tube (or channel) between the air impellor (e.g. air impellor, fan, turbine, propeller, pump, and/or blower) and an interior of the front portion of the mask.

In an example, an air exhaust port can be located above a person's mouth and/or below the person's nose. In an example, an air exhaust port can be located below a person's mouth and/or on the person's chin. In an example, an air exhaust port can be located on a person's cheek. In an example, an air impellor (e.g. air impellor, fan, turbine, propeller, pump, and/or blower) which is located on the back of a person's head can be located on the middle of the person's head (e.g. centered on a virtual plane which separates the right and left sides of the person's head).

In an example, a transparent portion of a face mask which covers a person's mouth can be impermeable to air. In an example, a transparent portion of a face mask which covers a person's mouth can be clear plastic. In an example, a transparent portion of a face mask which covers a person's mouth can have a perimeter which is shaped like the perimeter of a bicycle seat. In an example, a transparent portion of a face mask which covers a person's mouth can have an elliptical or oval shaped perimeter. In an example, a transparent portion of a face mask which covers a person's mouth can have a circular perimeter.

In an example, a first virtual plane is the plane which best fits a transparent portion of a face mask, a second virtual plane is the plane which best fits an air intake filter, and the second plane intersects the first virtual plane at an angle between 30 and 60 degrees. In an example, a first virtual plane is the vertical plane which divides the anterior vs. posterior halves of a person's head, a second virtual plane is the plane which best fits an air intake filter, and the second plane intersects the first virtual plane at an angle between 30 and 60 degrees.

In an example, an air filter can be shaped like a conic section. In an example, an air filter can comprise a mesh or grid of metal strands. In an example, an air filter can comprise a mesh or grid of polymer fibers. In an example, an air filter can feature electrostatic filtration. In an example, an air filter can include antimicrobial, antibacterial, and/or disinfectant material. In an example, an air filter can be made with silver material, such as silver nanoparticles or silver zinc. In an example, an air filter can use light energy for filtration and/or sanitization via an ultraviolet light emitter or an infrared light emitter. In an example, one or more layers of an air filter can be made with fabric. In an example, one or more layers of an air filter can be made with cotton, cotton-polyester, nylon, rayon, or felt.

In an example, a face mask can further comprise a blood oxygen sensor. In an example, a face mask can further comprise a carbon dioxide sensor. In an example, a face mask can further comprise a blood pressure sensor. In an example, a face mask can further comprise a camera and/or imaging sensor. In an example, the speed and/or volume of airflow through an air impellor can be increased or decreased based on analysis (e.g. pattern detection) of images captured by a camera on a face mask. In an example, the speed and/or volume of airflow through an air impellor can be increased when an environmental hazard is detected based on analysis (e.g. pattern detection) of images captured by a camera on a face mask.

In an example, an air intake filter can be located above a person's mouth and/or below the person's nose and an air exhaust filter can be located below a person's mouth and/or on the person's chin, or vice versa. In an example, an air intake filter can be located above a person's mouth and/or below the person's nose. In an example, an air intake filter can be located below a person's mouth and/or on the person's chin and an air exhaust filter can be located above a person's mouth and/or below the person's nose, or vice versa. In an example, an air intake filter can be located below a person's mouth and/or on the person's chin.

In an example, an air tube or channel between a transparent portion of a face mask and an air impellor (e.g. air impellor, fan, turbine, propeller, pump, and/or blower) on the back of a person's head can be substantially horizontal (when the person's head is upright) except for an undulation which curves over and around the person's ear. In an example, an air tube or channel between a transparent portion of a face mask and an air impellor on the back of a person's head can be substantially parallel to a virtual plane between the upper half of the person's head and the bottom half of the person's head, except for an undulation which curves over and around the person's ear.

In an example, an air tube (or channel) between a transparent portion of a face mask which covers a person's mouth and an air impellor (e.g. air impellor, fan, turbine, propeller, pump, and/or blower) on the back of the person's head can span the side of the person's head in a loop above and around the person's ear. In an example, an air tube (or channel) between a transparent portion of a face mask which covers a person's mouth and an air impellor on the back of the person's head can span the side of the person's head in a loop under and around the person's ear.

In an example, an air tube (or channel) between mask components on the back of a person's head and mask components on the front of the person's head can include an arcuate loop with a conic section shape which curves around and over a person's ear. In an example, an air tube (or channel) between an air intake filter on a front portion of a face mask and an air impellor (e.g. air impellor, fan, turbine, propeller, pump, and/or blower) on the back of a person's head can further comprise an arcuate loop with a conic section shape which curves around and over a person's ear. In an example, an air tube (or channel) between an air intake filter on a front portion of a face mask and an air impellor on the back of a person's head can further comprise an arcuate loop with downward-facing concavity which curves around and over a person's ear.

In an example, an air tube (or channel) can span (at least a portion of) the perimeter of a transparent portion of a face mask which covers a person's mouth, wherein there are a plurality of holes in the air tube (or channel) which draw air from different locations in a concave interior of the transparent portion. In an example, an air tube (or channel) can span (at least a portion of) the perimeter of a transparent portion of a face mask which covers a person's mouth, wherein there are a plurality of holes in the air tube (or channel) which expel air into different locations in a concave interior of the transparent portion and draw air out from different locations in the concave interior of the transparent portion.

In an example, an air tube (or channel) which conducts air between an air filter and an air impellor (e.g. air impellor, fan, turbine, propeller, pump, and/or blower) can have an inner diameter within the range of ⅛" to ¼". In an example, an air tube (or channel) which conducts air between an air filter and an air impellor (e.g. air impellor, fan, turbine, propeller, pump, and/or blower) can have an inner diameter within the range of ⅛" to ½". In an example, an air tube (or channel) which conducts air between an air filter and an air impellor (e.g. air impellor, fan, turbine, propeller, pump, and/or blower) can have an inner diameter within the range of ¼" to ½".

In an example, an air tube (or channel) which conveys airflow between an air impellor (e.g. air impellor, fan, turbine, propeller, pump, and/or blower) on the back of a person's head or neck and a transparent portion of a mask which covers the person's mouth can span a side of the person's head over the person's ear. In an example, an air tube (or channel) which conveys airflow between an air impellor (e.g. air impellor, fan, turbine, propeller, pump, and/or blower) on the back of a person's head or neck and a transparent portion of a mask which covers the person's mouth can span a side of the person's neck (e.g. within a collar).

In an example, a protective face mask can comprise: a transparent portion of a face mask which covers a person's mouth; an air intake filter on a portion of the perimeter of the transparent portion; an air impellor (e.g. air impellor, fan, turbine, propeller, pump, and/or blower) on the back of the person's head or neck; and an air tube (or channel) which conducts air between the air intake filter and the air impellor. In an example, a protective face mask can comprise: a transparent portion of a face mask which covers a person's mouth; an air exhaust filter on a portion of the perimeter of the transparent portion; an air impellor on the back of the person's head or neck; and an air tube (or channel) which conducts air between the air intake filter and the transparent portion.

In an example, a protective face mask can have a (concave) transparent portion which covers a person's mouth and is connected to the person's head by a right-side air tube (or channel) and a left-side air tube (or channel), wherein the right-side air tube (or channel) conducts air from an air filter on the front portion of the mask to an air impellor (e.g. air impellor, fan, turbine, propeller, pump, and/or blower) on the back of the person's head or neck, and wherein the left-side air tube (or channel) conducts air from the air impellor to the interior of the transparent portion.

In an example, a protective face mask can comprise: a face mask; a concave transparent portion of the face mask which is configured to cover a person's mouth; an air intake filter within 4" of the transparent portion; an air exhaust filter within 4" of the transparent portion; a first air tube or channel; a second air tube or channel; and an air impellor which is configured to be worn on the back of the person's head or neck; wherein air flows from the air intake filter to the air impellor through the first air tube or channel, and wherein air flows from the air impellor to the concave interior of the transparent portion through the second air tube or channel.

In an example, a protective face mask can comprise: a face mask; a concave transparent portion of the face mask which is configured to cover a person's mouth; an air intake port within 4" of the transparent portion; an air exhaust port within 4" of the transparent portion; an air intake filter; an air exhaust filter; a first air tube or channel; second air tube or channel; and an air impellor which is configured to be worn on the back of the person's head or neck; wherein air flows in from the environment to the air intake port, wherein air flows from the air intake port to the air intake filter, wherein air flows from the air intake filter to the air impellor through the first air tube or channel, wherein air flows from the air impellor to the concave interior of the transparent portion through the second air tube or channel, and wherein air flows out from a concave interior of the transparent portion to the environment through the air exhaust port.

In an example, a protective face mask can comprise: a face mask; wherein the face mask further comprises a concave transparent portion which covers a person's mouth; wherein the face mask further comprises an air intake port within 4" of the transparent portion; wherein the face mask further comprises an air intake filter within 4" of the transparent portion; wherein the face mask further comprises an air impellor, fan, turbine, propeller, pump, and/or blower located on the back of the person's head or neck; wherein the face mask further comprises a first air tube or channel which conducts air from the air intake filter to the air impellor, fan, turbine, propeller, pump, and/or blower; wherein the first air tube or channel is at least 5" long; wherein the face mask further comprises a second air tube or channel which conducts air from the air impellor, fan, turbine, propeller, pump, and/or blower to a concave interior of the transparent portion; wherein the second air tube or channel is at least 5" long; an air exhaust filter; and an air exhaust port.

In an example, a pathogen-filtering semi-transparent face mask can comprise: a transparent portion of a face mask which covers at least part of a person's mouth; a first-side air filter on a first side of the mask on the person's jaw; a first-side air impellor on the first side of the mask on the person's jaw which draws air into the mask from the environment through the first-side air filter; a second-side air filter on a second side of the mask on the person's jaw; a second-side air impellor on the second side of the mask on the person's jaw which draws air into the mask from the environment through the second-side air filter; a central air filter between the first-side air filter and the second-side air filter; and one or more air tubes or channels between the first-side and second-side air filters and an interior space of the transparent portion.

In an example, a pathogen-filtering semi-transparent face mask can comprise: a transparent portion of a face mask which covers at least part of a person's mouth; non-transparent portions of the face mask which hold the transparent portion on the person's head; a first-side air filter on a first side of the transparent portion; a first-side air impellor which moves air through the first-side air filter; a second-side air filter on a second side of the transparent portion; a second-side air impellor which moves air through the second-side air filter; and a concave air filter with a concavity which opens upwards toward the person's mouth.

In an example, a pathogen-filtering semi-transparent face mask can comprise: a transparent portion of a face mask which covers at least part of a person's mouth; a first-side air filter on a first side of the person's head, wherein the first-side air filter is behind the person's first-side ear; a first-side air impellor which moves air through the first-side air filter; a first-side air tube or channel which directs airflow between the first-side air filter and the transparent portion; a second-side air filter on a second side of the person's head, wherein the second-side air filter is behind the person's second-side ear; a second-side air impellor which moves air through the second-side air filter; a second-side air tube or channel which directs airflow between the second-side air filter and the transparent portion; and a lower air filter which spans at least 25% of the lower perimeter of the mask.

This disclosure now transitions from generic design concepts and variations to discussion of the specific examples shown in FIGS. 1 through 49. The design concepts and variations discussed above and in priority-linked disclosures can be applied to the specific examples in FIGS. 1 through 49 where relevant.

FIG. 1 shows an example of a pathogen-filtering semi-transparent face mask comprising: a transparent portion 104 of a face mask which covers at least part of a person's mouth; a non-transparent portion 105 of the face mask which holds the transparent portion on the person's head; an upper air filter 103 above the person's mouth; a lower air filter 102 below the person's mouth; and an air impellor 101 which draws air from the environment in through lower air filter.

In an example, a transparent portion of a face mask can cover (and/or span) a person's entire mouth. In an example, a transparent portion can cover a person's mouth and also portions of the person's cheeks. In an example, a transparent portion can cover a person's mouth, portions of the person's cheeks, and also a lower portion of the person's nose. In an example, the maximum distance from a transparent portion of a face mask to a person's mouth can be within the range of ½" to 3". In an example, the maximum distance from a transparent portion of a face mask to a person's mouth can be within the range of 1" to 4".

In an example, a transparent portion of a face mask can have a concave shape, wherein the concave interior of the transparent portion faces towards the person's mouth. In an example, a transparent portion of a face mask can have an arcuate concave shape. In an example, a transparent portion can have a shape which is a section of a sphere. In an example, a transparent portion can have a hemispherical shape. In an example, a transparent portion can have a shape which is a section of an oblate spheroid. In an example, a transparent portion can have a shape which is a section of an ellipsoid. In an example, a transparent portion can have a frustal shape. In an example, a transparent portion can have a shape which is a section of a round cylinder. In an example, a transparent portion can have a shape which is a section of a polygonal (e.g. quadrilateral, hexagonal, or octagonal) cylinder. In an example, a transparent portion can be shaped like the upper surface of a bicycle seat. In an example, a transparent portion can be shaped like the upper surface of a saddle.

In an example, a transparent portion of a face mask can be impermeable to air. In an example, a transparent portion of a face mask can be less permeable to air than a non-transparent portion of a face mask. In an example, a transparent portion can be less flexible than a non-transparent portion. In an example, a transparent portion can be rigid. In an example, a transparent portion can be made with a transparent polymer. In an example, a transparent portion can be coated with an anti-fogging coating. In an example, a transparent portion of a face mask can be heated to reduce fogging. In an example, airflow from an air impellor can be directed across the mouth-facing surface of a transparent portion of a face mask to reduce fogging.

In an example, a non-transparent portion of a face mask can hold a transparent portion of a face mask on a person's head by being attached to (e.g. looping around) the person's ears. In an example, a non-transparent portion can hold the transparent portion on a person's head by being attached to (e.g. looping around) the rear of the person's head. In an example, a non-transparent portion can comprise straps, bands, cords, or strings. In an example, a non-transparent portion can comprise four straps, bands, cords, or strings. In an example, a non-transparent portion can comprise two straps, bands, cords, or strings. In an example, a non-transparent portion can comprise elastic and/or stretchable straps, bands, cords, or strings.

In an example, a non-transparent portion can comprise fabric straps. In an example, a non-transparent portion can be made from a flexible fabric and/or textile. In an example, a non-transparent portion can be permeable to air. In an example, a non-transparent portion can be impermeable to air. In an example, a non-transparent portion can be less permeable to air than an air filter.

In an example, a transparent portion and a non-transparent portion of a face mask can be attached to each other by sewing or weaving. In an example, a transparent portion and a non-transparent portion can be attached to each other by adhesion and/or gluing. In an example, a transparent portion and a non-transparent portion can be attached to each other by melting and/or welding. In an example, a transparent portion and a non-transparent portion can be attached to each other by snaps, clips, clamps, hooks, pins, prongs, or buttons.

In an example, an upper air filter on a face mask can have a longitudinal shape. In an example, an upper air filter can have an arcuate longitudinal shape. In an example, an upper air filter can be located along the upper perimeter of a transparent portion of a face mask. In an example, an upper air filter can be located between an upper perimeter of a transparent portion of a face mask and a non-transparent portion of the face mask. In an example, an upper air filter can be located on the upper half of the transparent portion of a face mask. In an example, the closest distance between an upper air filter and a person's nose nostrils can be between ¼" and 2". In an example, an upper air filter can be substantially parallel with the surface of a non-transparent portion of a face mask. In an example, an upper air filter can be substantially orthogonal to the surface of a non-transparent portion of a face mask. In an example, an upper air filter can be located below a person's nose. In an example, an upper air filter can be located over a person's nose.

In an example, an upper air filter can be removably attached to a face mask via a clip, snap, clasp, hook, clamp, adhesive substance, or pin. In an example, an upper air filter can be disposable. In an example, an upper air filter can be detached from a face mask, cleaned, and then reattached to the face mask. In an example, a mask can further comprise a sensor which tracks the cumulative airflow through an upper filter and indicates when the upper air filter should be changed and/or cleaned. In an example, a mask can further comprise a sensor which tracks the level of airflow resistance through an upper filter and indicates when the upper air filter should be changed and/or cleaned. In an example, there can be two air filters, wherein the mask directs airflow through a first filter until a sensor detects that the first filter is dirty, at which time the mask automatically redirects airflow through a second filter. In an example, an upper air filter can further comprise two air filters, wherein the mask directs air through a second filter when the first filter becomes dirty and/or clogged.

In an example, when an air impellor is active (e.g. rotating and drawing air in through the lower filter) then airflow through an upper air filter can be: primarily or entirely from the interior of a face mask (e.g. the interior of the concavity of a transparent portion of the mask) out to the environment. In an example, when an air impellor is not active (e.g. not rotating and drawing air in through the lower filter), then airflow through the upper air filter can be: from the environment in to the interior of the face mask (e.g. the interior of the concavity of a transparent portion of the mask) when the person is inhaling; and from the interior of the face mask to the environment when the person is exhaling. This can enable passive two-way air filtering when the air impellor is not active in order to save energy. Alternatively, an upper air filter can further comprise a one-way valve which does not allow air to flow from the environment to the interior of the face mask.

In an example, a lower air filter on a face mask can have a circular shape. In an example, a lower air filter can have an arcuate shape. In an example, a lower air filter can be located along the lower perimeter of the transparent portion of a face mask. In an example, a lower air filter can be located between a lower perimeter of a transparent portion of a face mask and a non-transparent portion of the face mask. In an example, a lower air filter can be located in the lower half of the transparent portion of a face mask. In an example, a lower air filter can be located on a person's jaw and/or chin. In an example, a lower air filter can be located below a person's jaw and/or chin.

In an example, a lower air filter can be between an air impellor and the environment. In an example, a lower air filter can be between an air impellor and the interior of the mask. In an example, a lower filter can comprise two filter layers, one layer between an air impellor and the environment and one layer between the air impellor and the interior of the mask (e.g. the space inside a concave transparent portion of the mask). In an example, a face mask can further comprise one or more air tubes, channels, and/or pathways through which air flows from a lower air filter to an interior concavity of a transparent portion of the mask. In an example, a face mask can further comprise one or more flexible air tubes, channels, and/or pathways through which air flows from a lower air filter to the interior concavity of a transparent portion of the mask.

In an example, a lower air filter can be removably attached to a face mask via a clip, snap, clasp, hook, clamp, adhesive substance, or pin. In an example, a lower air filter can be disposable. In an example, a lower air filter can be detached from a face mask, cleaned, and then reattached to the face mask. In an example, a mask can further comprise a sensor which tracks the cumulative airflow through a lower air filter and indicates when the lower air filter should be changed and/or cleaned. In an example, a mask can further comprise a sensor which tracks the level of airflow resistance through a lower air filter and indicates when the lower air filter should be changed and/or cleaned. In an example, there can be two air filters, wherein the mask directs airflow through a first filter until a sensor detects that the first filter is dirty, at which time the mask automatically redirects airflow through a second filter. In an example, a lower air filter can further comprise two air filters, wherein the mask directs air through a second filter when the first filter becomes dirty and/or clogged.

In an example, when an air impellor is active (e.g. rotating and drawing air in through the lower filter) then airflow through a lower air filter can be: primarily or entirely from the environment to the interior of a face mask (e.g. the interior of the concavity of a transparent portion of the mask). In an example, when an air impellor is not active (e.g. not rotating and drawing air in through the lower filter), then airflow through the lower air filter can be: from the environment to the interior of the face mask (e.g. the interior of the concavity of a transparent portion of the mask) when the person is inhaling; and from the interior of the face mask to the environment when the person is exhaling. Alternatively, a lower air filter can further comprise a one-way valve which does not allow air to flow from the interior of the face mask to the environment.

In an example, an air impellor can be selected from the group consisting of: a fan, a turbine, a propeller, a helix, and a pump. In an example, an air impellor can rotate. In an example, an air impellor can be rotated by an electromagnetic motor. In an example, an air impellor can move air from the environment through a lower air filter into the interior of a face mask. In an example, a face mask can further comprise one or more air tubes, channels, and/or pathways through which air flows from an air impellor to an interior concavity of a transparent portion of the mask. In an example, a face mask can further comprise one or more flexible air tubes, channels, and/or pathways through which air flows from an air impellor to the interior concavity of a transparent portion of the mask.

In an example, the rotational speed of an air impellor can be varied. In an example, an air impellor can have different speed settings. In an example, a user can manually change the rotational speed of an air impellor. In an example, a face mask can automatically change the rotational speed of an air impellor in response to data from biometric and/or environmental sensors. In an example, a user can manually change the rotational direction of an air impellor (and thus the direction of active airflow). In an example, a face mask can automatically change the rotational direction of an air impellor (and thus the direction of active airflow).

In an example, a face mask can further comprise one or more sensors. In an example, the airflow of a face mask is automatically adjusted based on analysis of data from one or more sensors on the mask. In an example, the airflow of a face mask is automatically adjusted based on analysis of data from one or more biometric and/or physiological sensors on the mask. In an example, the airflow of a face mask is automatically adjusted based on analysis of data from one or more environmental sensors on the mask. In an example, a face mask can further comprise one or more sensors and the rotational speed of an air impellor is automatically changed in response to data from the one or more sensors.

In an example, a face mask can further comprise one or more sensors which evaluate attributes of air inside the mask (e.g. oxygen level, carbon dioxide level, temperature, and/or humidity level) and the rotational speed of an air impellor is automatically changed in response to data from the one or more sensors. In an example, a face mask can further comprise one or more sensors which evaluate attributes of air inside the mask (e.g. oxygen level, carbon dioxide level, temperature, and/or humidity level) and the rotational speed of an air impellor is automatically increased in response to data from the one or more sensors (e.g. in response to low oxygen level, high carbon dioxide level, high or low temperature, and/or high humidity level). In an example, a face mask can further comprise one or more biometric and/or physiological sensors (e.g. pulse oximeter, EMG sensor, and/or motion sensor) and the rotational speed of an air impellor is automatically changed in response to data from the one or more sensors.

In an example, a face mask can have: an active filtration mode (wherein movement of air through one or more air filters on the mask is caused primarily or entirely by one or more air impellors); and a passive filtration mode (wherein the air impellors are not activated and movement of air through one or more air filters on the mask is caused entirely or primarily by a person's inhalation and exhalation). In an example, a face mask can automatically switch to active filtration mode when data from biometric and/or environmental sensors indicates that a high level of air filtration and/or airflow is needed and can automatically switch to passive filtration mode when data from those sensors indicates that a high level of air filtration and/or airflow is not needed. In an example, active filtration can be initiated when the oxygen level inside the mask is low or when a wearer enters a high-risk environmental situation. In this manner, a face mask can conserve energy (and prolong battery life) by only initiating active filtration only when it is needed.

In an example, a face mask can further comprise one or more components selected from the group consisting of: data processor, power source (e.g. battery), data transmitter/receiver, biometric and/or physiological sensor, environmental sensor, microphone, speaker, interior mask light, exterior mask light, ultraviolet light emitter in optical communication with airflow within the mask, touch screen, push buttons or switches, a strap or band which loops around the back of a person's head, and a strap or band which loops over the top of a person's head. In an example, a face mask can further comprise a microphone which is in acoustic communication with the interior of the mask (e.g. with the interior of the transparent portion) and a speaker which reproduces sound recorded by the microphone. In an example, a face mask can further comprise a microphone on the inside of the mask which records a person's voice and a speaker on the outside of the mask which reproduces the person's voice. In an example, a face mask can further comprise one or more lights on the inside of the mask which highlight a person's mouth in order to increase visibility of the person's mouth (e.g. lip motion and facial expression) by nearby people. Other design variations discussed elsewhere in this disclosure or in priority-linked disclosures can also be applied to this example where relevant.

Figure 2:
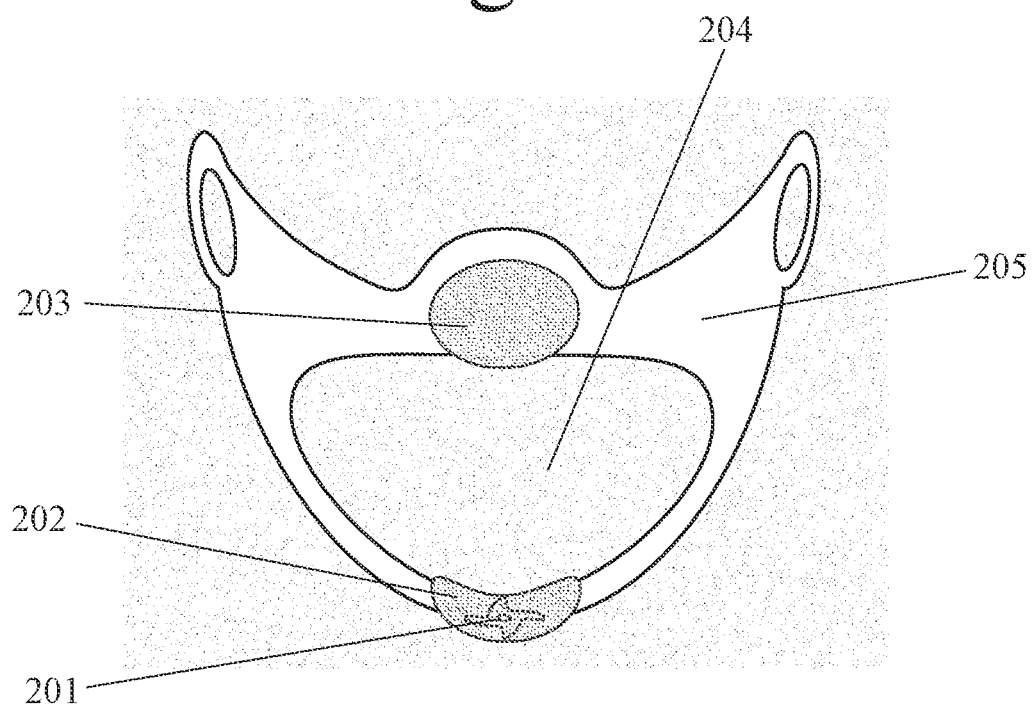
FIG. 2 shows a face mask with a transparent portion, a non-transparent portion, a convex air filter above a mouth, and an air filter and impellor below the mouth.

FIG. 2 shows an example of a face mask which is similar to the one shown in FIG. 1 except that the upper air filter is more circular (e.g. elliptical or oval) in shape. FIG. 2 shows an example of a pathogen-filtering semi-transparent face mask comprising: a transparent portion 204 of a face mask which covers at least part of a person's mouth; a non-transparent portion 205 of the face mask which holds the transparent portion on the person's head; an upper air filter 203 above the person's mouth; a lower air filter 202 below the person's mouth; and an air impellor 201 which draws air from the environment in through lower air filter. Other design variations discussed elsewhere in this disclosure or in priority-linked disclosures can also be applied to this example where relevant.

Figure 3:
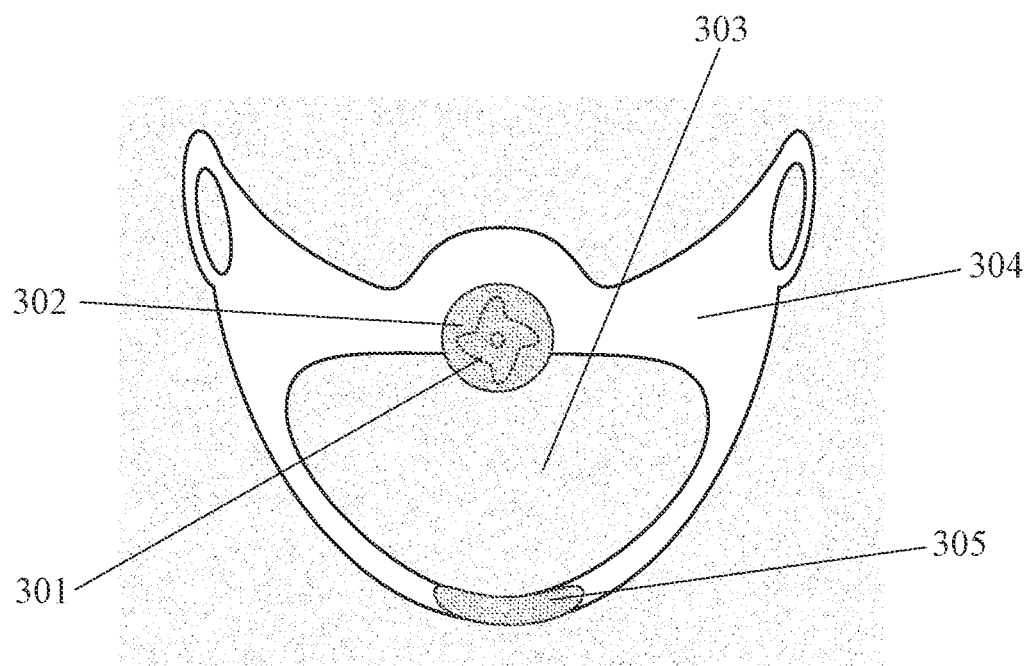
FIG. 3 shows a face mask with a transparent portion, a non-transparent portion, an air filter and impellor above a mouth, and an air filter below the mouth.

FIG. 3 shows an example of a face mask which is similar to the one shown in FIG. 2 except that an air impellor draws air in through the upper air filter instead of the lower air filter. FIG. 3 shows an example of a pathogen-filtering semi-transparent face mask comprising: a transparent portion 303 of a face mask which covers at least part of a person's mouth; a non-transparent portion 304 of the face mask which holds the transparent portion on the person's head; an upper air filter 302 above the person's mouth; an air impellor 301 which draws air from the environment in through lower air filter; and a lower air filter 305 below the person's mouth.

In an example, an upper air filter on a face mask can have a circular, elliptical, or oval shape. In an example, an upper air filter can be located on the upper perimeter of the transparent portion of a face mask. In an example, an upper air filter can be located between an upper perimeter of a transparent portion of a face mask and a non-transparent portion of the face mask. In an example, an upper air filter can be located in the upper half of the transparent portion of a face mask. In an example, the closest distance between an upper air filter and a person's nose nostrils can be between ¼" and 2". In an example, an upper air filter can be substantially parallel with the surface of a non-transparent portion of a face mask. In an example, an upper air filter can be substantially orthogonal to the surface of a non-transparent portion of a face mask. In an example, an upper air filter can be located below a person's nose. In an example, an upper air filter can be located over a person's nose.

In an example, an upper air filter can be removably attached to a face mask via a clip, snap, clasp, hook, clamp, adhesive substance, or pin. In an example, an upper air filter can be disposable. In an example, an upper air filter can be detached from a face mask, cleaned, and then reattached to the face mask. In an example, a mask can further comprise a sensor which tracks the cumulative airflow through an upper filter and indicates when the upper air filter should be changed and/or cleaned. In an example, a mask can further comprise a sensor which tracks the level of airflow resistance through an upper filter and indicates when the upper air filter should be changed and/or cleaned. In an example, there can be two air filters, wherein the mask directs airflow through a first filter until a sensor detects that the first filter is dirty, at which time the mask automatically redirects airflow through a second filter. In an example, an upper air filter can further comprise two air filters, wherein the mask directs air through a second filter when the first filter becomes dirty and/or clogged.

In an example, an upper air filter can be between an air impellor and the environment. In an example, an upper air filter can be between an air impellor and the interior of the mask. In an example, an upper filter can comprise two filter layers, one layer between an air impellor and the environment and one layer between the air impellor and the interior of the mask (e.g. the space inside a concave transparent portion of the mask).

In an example, when an air impellor is active (e.g. rotating and drawing air through the upper air filter) then airflow through an upper air filter can be: primarily or entirely from the environment to the interior of a face mask (e.g. the interior of the concavity of a transparent portion of the mask). In an example, when an air impellor is not active (e.g. not rotating and drawing air through the upper air filter), then airflow through the upper air filter can be: from the environment to the interior of the face mask (e.g. the interior of the concavity of a transparent portion of the mask) when the person is inhaling; and from the interior of the face mask to the environment when the person is exhaling. Alternatively, an upper air filter can further comprise a one-way valve which does not allow air to flow from the interior of the face mask to the environment.

In an example, an air impellor can be selected from the group consisting of: a fan, a turbine, a propeller, a helix, and a pump. In an example, an air impellor can rotate. In an example, an air impellor can be rotated by an electromagnetic motor. In an example, an air impellor can move air from the environment through an upper air filter into the interior of a face mask. In an example, a face mask can further comprise one or more air tubes, channels, and/or pathways through which air flows from an air impellor to an interior concavity of a transparent portion of the mask. In an example, a face mask can further comprise one or more flexible air tubes, channels, and/or pathways through which air flows from an air impellor to the interior concavity of a transparent portion of the mask.

In an example, the rotational speed of an air impellor can be varied. In an example, an air impellor can have different speed settings. In an example, a user can manually change the rotational speed of an air impellor. In an example, a face mask can automatically change the rotational speed of an air impellor in response to data from biometric and/or environmental sensors. In an example, a user can manually change the rotational direction of an air impellor (and thus the direction of active airflow). In an example, a face mask can automatically change the rotational direction of an air impellor (and thus the direction of active airflow).

In an example, a face mask can further comprise one or more sensors. In an example, the airflow of a face mask is automatically adjusted based on analysis of data from one or more sensors on the mask. In an example, the airflow of a face mask is automatically adjusted based on analysis of data from one or more biometric and/or physiological sensors on the mask. In an example, the airflow of a face mask is automatically adjusted based on analysis of data from one or more environmental sensors on the mask. In an example, a face mask can further comprise one or more sensors and the rotational speed of an air impellor is automatically changed in response to data from the one or more sensors.

In an example, a face mask can further comprise one or more sensors which evaluate attributes of air inside the mask (e.g. oxygen level, carbon dioxide level, temperature, and/or humidity level) and the rotational speed of an air impellor is automatically changed in response to data from the one or more sensors. In an example, a face mask can further comprise one or more sensors which evaluate attributes of air inside the mask (e.g. oxygen level, carbon dioxide level, temperature, and/or humidity level) and the rotational speed of an air impellor is automatically increased in response to data from the one or more sensors (e.g. in response to low oxygen level, high carbon dioxide level, high or low temperature, and/or high humidity level). In an example, a face mask can further comprise one or more biometric and/or physiological sensors (e.g. pulse oximeter, EMG sensor, and/or motion sensor) and the rotational speed of an air impellor is automatically changed in response to data from the one or more sensors.

In an example, a face mask can have: an active filtration mode (wherein movement of air through one or more air filters on the mask is caused primarily or entirely by one or more air impellors); and a passive filtration mode (wherein the air impellors are not activated and movement of air through one or more air filters on the mask is caused entirely or primarily by a person's inhalation and exhalation). In an example, a face mask can automatically switch to active filtration mode when data from biometric and/or environmental sensors indicates that a high level of air filtration and/or airflow is needed and can automatically switch to passive filtration mode when data from those sensors indicates that a high level of air filtration and/or airflow is not needed. In an example, active filtration can be initiated when the oxygen level inside the mask is low or when a wearer enters a high-risk environmental situation. In this manner, a face mask can conserve energy (and prolong battery life) by only initiating active filtration only when it is needed.

In an example, a lower air filter on a face mask can have a longitudinal shape. In an example, a lower air filter can have a circular, elliptical, or oval. In an example, a lower air filter can be located along the lower perimeter of the transparent portion of a face mask. In an example, a lower air filter can be located between a lower perimeter of a transparent portion of a face mask and a non-transparent portion of the face mask. In an example, a lower air filter can be located in the lower half of the transparent portion of a face mask. In an example, a lower air filter can be located on a person's jaw and/or chin. In an example, a lower air filter can be located below a person's jaw and/or chin. In an example, a face mask can further comprise one or more air tubes, channels, and/or pathways through which air flows from a lower air filter to the interior concavity of a transparent portion of the mask. In an example, a face mask can further comprise one or more flexible air tubes, channels, and/or pathways through which air flows from a lower air filter to the interior concavity of a transparent portion of the mask.

In an example, a lower air filter can be removably attached to a face mask via a clip, snap, clasp, hook, clamp, adhesive substance, or pin. In an example, a lower air filter can be disposable. In an example, a lower air filter can be detached from a face mask, cleaned, and then reattached to the face mask. In an example, a mask can further comprise a sensor which tracks the cumulative airflow through a lower air filter and indicates when the lower air filter should be changed and/or cleaned. In an example, a mask can further comprise a sensor which tracks the level of airflow resistance through a lower air filter and indicates when the lower air filter should be changed and/or cleaned. In an example, there can be two air filters, wherein the mask directs airflow through a first filter until a sensor detects that the first filter is dirty, at which time the mask automatically redirects airflow through a second filter. In an example, a lower air filter can further comprise two air filters, wherein the mask directs air through a second filter when the first filter becomes dirty and/or clogged.

In an example, when an air impellor is active (e.g. rotating and drawing air in through the upper air filter) then airflow through a lower air filter can be: primarily or entirely from the interior of a face mask (e.g. the interior of the concavity of a transparent portion of the mask) out to the environment. In an example, when an air impellor is not active (e.g. not rotating and drawing air in through the upper air filter), then airflow through the lower air filter can be: from the environment in to the interior of the face mask (e.g. the interior of the concavity of a transparent portion of the mask) when the person is inhaling; and from the interior of the face mask to the environment when the person is exhaling. This can enable passive two-way air filtering when the air impellor is not active in order to save energy. Alternatively, a lower air filter can further comprise a one-way valve which does not allow air to flow from the environment in to the interior of the face mask.

In an example, a face mask can further comprise one or more components selected from the group consisting of: data processor, power source (e.g. battery), data transmitter/receiver, biometric and/or physiological sensor, environmental sensor, microphone, speaker, interior mask light, exterior mask light, ultraviolet light emitter in optical communication with airflow within the mask, touch screen, push buttons or switches, a strap or band which loops around the back of a person's head, and a strap or band which loops over the top of a person's head. In an example, a face mask can further comprise a microphone which is in acoustic communication with the interior of the mask (e.g. with the interior of the transparent portion) and a speaker which reproduces sound recorded by the microphone. In an example, a face mask can further comprise a microphone on the inside of the mask which records a person's voice and a speaker on the outside of the mask which reproduces the person's voice. In an example, a face mask can further comprise one or more lights on the inside of the mask which highlight a person's mouth in order to increase visibility of the person's mouth (e.g. lip motion and facial expression) by nearby people. Other design variations discussed elsewhere in this disclosure or in priority-linked disclosures can also be applied to this example where relevant.

Figure 4:
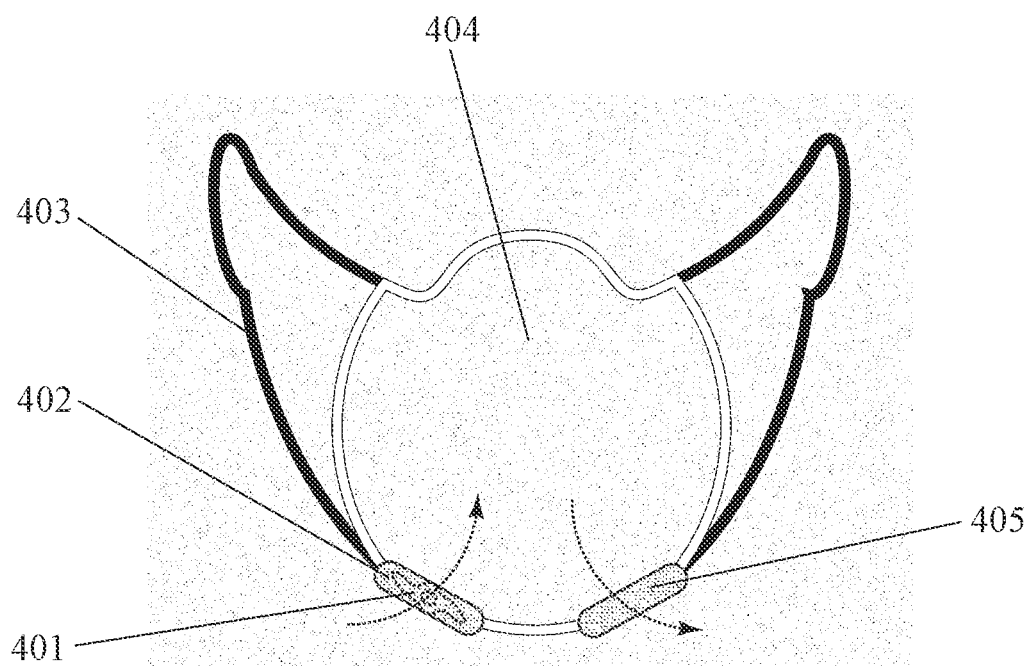
FIG. 4 shows a face mask with a transparent portion, straps, a first-side air filter and impellor on a person's jaw, and a second-side air filter on the person's jaw.

FIG. 4 shows an example of a pathogen-filtering semi-transparent face mask comprising: a transparent portion 404 of a face mask which covers at least part of a person's mouth; straps (including strap 403) which hold the transparent portion on the person's head; a first-side air filter 402 on a first side (e.g. the right side) of the mask below the person's mouth; a second-side air filter 405 on a second side (e.g. the left side) of the mask below the person's mouth; and an air impellor 401 which draws air from the environment in through first-side air filter.

In an example, a first-side air filter on a face mask can have a circular, elliptical, or oval shape. In an example, a first-side air filter can be located on a first-side (e.g. right side) perimeter of the transparent portion of a face mask. In an example, a first-side air filter can be located between a first-side (e.g. right side) perimeter of a transparent portion of a face mask and a non-transparent portion of the face mask. In an example, a first-side air filter can be located on the first-side half (e.g. on the right half) of a transparent portion of a face mask. In an example, a first-side air filter can be located on a person's jaw, chin, and/or neck. In an example, being "below a person's mouth" can be defined as being located at a height which is lower than the height of the lowest point of a person's mouth when the person is standing up with their head erect.

In an example, a first-side air filter can be removably attached to a face mask via a clip, snap, clasp, hook, clamp, adhesive substance, or pin. In an example, a first-side air filter can be disposable. In an example, a first-side air filter can be detached from a face mask, cleaned, and then reattached to the face mask. In an example, a mask can further comprise a sensor which tracks the cumulative airflow through a first-side filter and indicates when the first-side air filter should be changed and/or cleaned. In an example, a mask can further comprise a sensor which tracks the level of airflow resistance through a first-side filter and indicates when the first-side air filter should be changed and/or cleaned. In an example, there can be two air filters, wherein the mask directs airflow through a first filter until a sensor detects that the first filter is dirty, at which time the mask automatically redirects airflow through a second filter. In an example, a first-side air filter can further comprise two air filters, wherein the mask directs air through a second filter when the first filter becomes dirty and/or clogged.

In an example, a first-side air filter can be between an air impellor and the environment. In an example, a first-side air filter can be between an air impellor and the interior of the mask. In an example, a first-side filter can comprise two filter layers, one layer between an air impellor and the environment and one layer between the air impellor and the interior of the mask (e.g. the space inside a concave transparent portion of the mask).

In an example, when an air impellor is active (e.g. rotating and drawing air in through the first-side air filter) then airflow through a first-side air filter can be: primarily or entirely from the environment to the interior of a face mask (e.g. the interior of the concavity of a transparent portion of the mask). In an example, when an air impellor is not active (e.g. not rotating and drawing air in through the first-side air filter), then airflow through the first-side air filter can be: from the environment to the interior of the face mask (e.g. the interior of the concavity of a transparent portion of the mask) when the person is inhaling; and from the interior of the face mask to the environment when the person is exhaling. Alternatively, a first-side air filter can further comprise a one-way valve which does not allow air to flow from the interior of the face mask to the environment.

In an example, an air impellor can be selected from the group consisting of: a fan, a turbine, a propeller, a helix, and a pump. In an example, an air impellor can rotate. In an example, an air impellor can be rotated by an electromagnetic motor. In an example, an air impellor can move air from the environment through a first-side air filter into the interior of a face mask. In an example, a face mask can further comprise one or more air tubes, channels, and/or pathways through which air flows from an air impellor to the interior concavity of a transparent portion of the mask. In an example, a face mask can further comprise one or more flexible air tubes, channels, and/or pathways through which air flows from an air impellor to the interior concavity of a transparent portion of the mask.

In an example, the rotational speed of an air impellor can be varied. In an example, an air impellor can have different speed settings. In an example, a user can manually change the rotational speed of an air impellor. In an example, a face mask can automatically change the rotational speed of an air impellor in response to data from biometric and/or environmental sensors. In an example, a user can manually change the rotational direction of an air impellor (and thus the direction of active airflow). In an example, a face mask can automatically change the rotational direction of an air impellor (and thus the direction of active airflow).

In an example, a face mask can further comprise one or more sensors. In an example, the airflow of a face mask is automatically adjusted based on analysis of data from one or more sensors on the mask. In an example, the airflow of a face mask is automatically adjusted based on analysis of data from one or more biometric and/or physiological sensors on the mask. In an example, the airflow of a face mask is automatically adjusted based on analysis of data from one or more environmental sensors on the mask. In an example, a face mask can further comprise one or more sensors and the rotational speed of an air impellor is automatically changed in response to data from the one or more sensors.

In an example, a face mask can further comprise one or more sensors which evaluate attributes of air inside the mask (e.g. oxygen level, carbon dioxide level, temperature, and/or humidity level) and the rotational speed of an air impellor is automatically changed in response to data from the one or more sensors. In an example, a face mask can further comprise one or more sensors which evaluate attributes of air inside the mask (e.g. oxygen level, carbon dioxide level, temperature, and/or humidity level) and the rotational speed of an air impellor is automatically increased in response to data from the one or more sensors (e.g. in response to low oxygen level, high carbon dioxide level, high or low temperature, and/or high humidity level). In an example, a face mask can further comprise one or more biometric and/or physiological sensors (e.g. pulse oximeter, EMG sensor, and/or motion sensor) and the rotational speed of an air impellor is automatically changed in response to data from the one or more sensors.

In an example, a face mask can have: an active filtration mode (wherein movement of air through one or more air filters on the mask is caused primarily or entirely by the activation of one or more air impellors); and a passive filtration mode (wherein the air impellors are not activated and movement of air through one or more air filters on the mask is caused entirely or primarily by a person's inhalation and exhalation). In an example, a face mask can automatically switch to active filtration mode when data from biometric and/or environmental sensors indicates that a high level of air filtration and/or airflow is needed and can automatically switch to passive filtration mode when data from those sensors indicates that a high level of air filtration and/or airflow is not needed. In an example, active filtration can be initiated when the oxygen level inside the mask is low or when a wearer enters a high-risk environmental situation. In this manner, a face mask can conserve energy (and prolong battery life) by only initiating active filtration only when it is needed.

In an example, a second-side (e.g. left side) air filter on a face mask can have a circular, elliptical, oval, or longitudinal shape. In an example, a second-side air filter can be located along a second-side (e.g. left side) perimeter of the transparent portion of a face mask. In an example, a second-side air filter can be located between a second-side (e.g. left side) perimeter of a transparent portion of a face mask and a non-transparent portion of the face mask. In an example, a second-side air filter can be located on the second-side half (e.g. the left half) of a transparent portion of a face mask. In an example, a second-side air filter can be located on a person's jaw and/or chin. In an example, a second-side air filter can be located on a person's jaw, chin, or neck. In an example, a face mask can further comprise one or more air tubes, channels, and/or pathways through which air flows from a second-side air filter to the interior concavity of a transparent portion of the mask. In an example, a face mask can further comprise one or more flexible air tubes, channels, and/or pathways through which air flows from a second-side air filter to the interior concavity of a transparent portion of the mask.

In an example, a second-side air filter can be removably attached to a face mask via a clip, snap, clasp, hook, clamp, adhesive substance, or pin. In an example, a second-side air filter can be disposable. In an example, a second-side air filter can be detached from a face mask, cleaned, and then reattached to the face mask. In an example, a mask can further comprise a sensor which tracks the cumulative airflow through a second-side air filter and indicates when the second-side air filter should be changed and/or cleaned. In an example, a mask can further comprise a sensor which tracks the level of airflow resistance through a second-side air filter and indicates when the second-side air filter should be changed and/or cleaned. In an example, there can be two air filters, wherein the mask directs airflow through a first filter until a sensor detects that the first filter is dirty, at which time the mask automatically redirects airflow through a second filter. In an example, a second-side air filter can further comprise two air filters, wherein the mask directs air through a second filter when the first filter becomes dirty and/or clogged.

In an example, when an air impellor is active (e.g. rotating and drawing air in through the first-side air filter) then airflow through a second-side air filter can be: primarily or entirely from the interior of a face mask (e.g. the interior of the concavity of a transparent portion of the mask) out to the environment. In an example, when an air impellor is not active (e.g. not rotating and drawing air in through the first-side air filter), then airflow through the second-side air filter can be: from the environment in to the interior of the face mask (e.g. the interior of the concavity of a transparent portion of the mask) when the person is inhaling; and from the interior of the face mask to the environment when the person is exhaling. This can enable passive two-way air filtering when the air impellor is not active in order to save energy. Alternatively, a second-side air filter can further comprise a one-way valve which does not allow air to flow from the environment in to the interior of the face mask.

In an example, a face mask can further comprise one or more components selected from the group consisting of: data processor, power source (e.g. battery), data transmitter/receiver, biometric and/or physiological sensor, environmental sensor, microphone, speaker, interior mask light, exterior mask light, ultraviolet light emitter in optical communication with airflow within the mask, touch screen, push buttons or switches, a strap or band which loops around the back of a person's head, and a strap or band which loops over the top of a person's head. In an example, a face mask can further comprise a microphone which is in acoustic communication with the interior of the mask (e.g. with the interior of the transparent portion) and a speaker which reproduces sound recorded by the microphone. In an example, a face mask can further comprise a microphone on the inside of the mask which records a person's voice and a speaker on the outside of the mask which reproduces the person's voice. In an example, a face mask can further comprise one or more lights on the inside of the mask which highlight a person's mouth in order to increase visibility of the person's mouth (e.g. lip motion and facial expression) by nearby people. Other design variations discussed elsewhere in this disclosure or in priority-linked disclosures can also be applied to this example where relevant.

Figure 5:
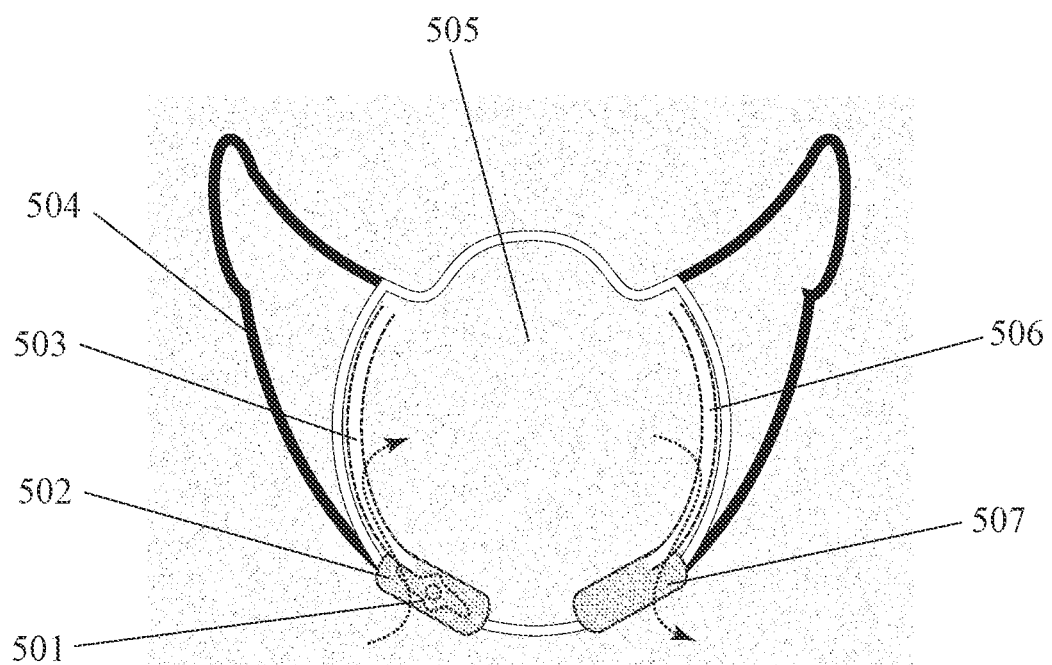
FIG. 5 shows a face mask with a transparent portion, straps, a first-side air filter and impellor on a person's jaw, a second-side air filter on the person's jaw, and air tubes or channels.

FIG. 5 shows an example of a face mask which is similar to the one shown in FIG. 4 except that it further comprises air tubes (e.g. air tubes, channels, or pathways) through which air flows between air filters and the interior of a transparent portion of the mask. FIG. 5 shows an example of a pathogen-filtering semi-transparent face mask comprising: a transparent portion 505 of a face mask which covers at least part of a person's mouth; straps (including strap 504) which hold the transparent portion on the person's head; a first-side air filter 502 on a first side (e.g. the right side) of the mask below the person's mouth; a first-side air tube (or channel) 503 between the first-side air filter and an interior space of the transparent portion; a second-side air filter 507 on a second side (e.g. the left side) of the mask below the person's mouth; a second-side air tube (or channel) 506 between the first-side air filter and the interior space of the transparent portion; and an air impellor 501 which draws air from the environment in through first-side air filter.

In an example, an air tube (e.g. air tube, channel, or pathway) can channel airflow between an air filter and an interior space of a transparent portion of a mask. This can be especially useful when an air filter and/or an air impellor are located relatively far away from the transparent portion of the mask for esthetic and/or other design reasons. In an example, a first air tube can channel airflow between a first air filter and an interior space of a transparent portion of a mask and a second air tube can channel airflow between a second air filter and the interior space of the transparent portion of the mask. In an example, a first air tube can (primarily) channel air from the environment into the interior space of the mask and a second air tube can (primarily) channel air out from the interior space into the environment. In an example, an air tube can channel airflow between an air impellor and an interior space of a transparent portion of a mask. In an example, an air impellor and the interior space of a transparent portion of a mask can be in fluid communication with each other through an air tube. In an example, an air filter and the interior space of a transparent portion of a mask can be in fluid communication with each other through an air tube.

In an example, an air tube (e.g. air tube, channel, or pathway) can span a portion of the perimeter of a transparent portion of a mask. In an example, an arcuate air tube can curve around a portion of an arcuate perimeter of a transparent portion of a mask. In an example, a right-side air tube can span the right-side perimeter of a transparent portion of a mask and a left-side air tube can span the left-side perimeter of the transparent portion of the mask. In an example, a right-side air tube can be on the right side of a transparent portion of a mask and a left-side air tube can be on the left side of the transparent portion of the mask. In an example, the perimeter of a transparent portion of a mask can be generally circular and an air tube can be generally semicircular. In an example, the perimeter of a transparent portion of a mask can be generally circular and an air tube can have a shape which is a section (e.g. an arc portion) of a circle.

In an example, an air tube in a mask can have an air-impermeable section and an air-permeable (e.g. perforated) section. In an example, the air-permeable section can have holes, openings, and perforations which allow fluid communication (e.g. air flow) with the interior space of the mask. In an example, the air-impermeable section can be closer to an air filter or air impellor and the air-permeable section can be closer to the interior space of a mask. In an example, the air-permeable section can have holes, openings, and perforations which allow fluid communication (e.g. air flow) with the interior space of transparent portion of the mask. In an example, the air-impermeable section can be closer to an air filter or air impellor and the air-permeable section can be closer to the interior space of the transparent portion of a mask.

In an example, the inner diameter of an air tube (e.g. air tube, channel, or pathway) can be within the range of ⅛" to ½". In an example, the length of an air tube can be within the range of ½" to 5". In an example, between 25% and 75% of the length of an air tube can be perforated with holes. In an example, between 50% and 80% of the length of an air tube can be perforated with holes. In an example, the interior of an air tube can have a circular cross-sectional shape. In an example, the interior of an air tube can have an elliptical, oval, and/or oblong cross-sectional shape. In an example, an air tube can be detached from a mask for cleaning and then reattached. Other design variations discussed elsewhere in this disclosure or in priority-linked disclosures can also be applied to this example where relevant.

Figure 6:
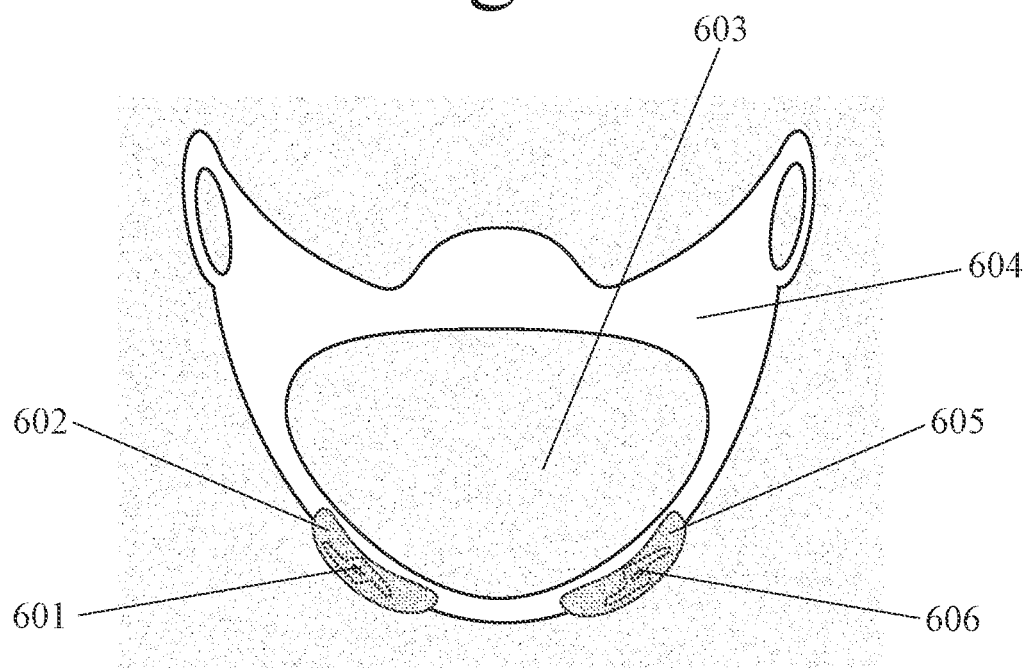
FIG. 6 shows a face mask with a transparent portion, a non-transparent portion, a first-side air filter and impellor on a person's jaw, and a second-side air filter and impellor on the person's jaw.

FIG. 6 shows an example of a pathogen-filtering semi-transparent face mask comprising: a transparent portion 603 of a face mask which covers at least part of a person's mouth; a non-transparent portion 604 of the face mask which holds the transparent portion on the person's head; a first-side air filter 602 on a first side (e.g. the right side) of the mask on the person's jaw; a first-side air impellor 601 on the first side of the mask on the person's jaw which draws air through the first-side air filter; a second-side air filter 605 on a second side (e.g. the left side) of the mask on the person's jaw; and a second-side air impellor 606 on the second side of the mask on the person's jaw which draws air through the second-side air filter.

In an example, a first and/or second air filter can be on a person's jaw, chin, or neck. In an example, a first and/or second air filter can be below a person's jaw and/or chin. In an example, a first and/or second air filter can be location at substantially the same height as a person's mouth. In an example, a first and/or second air filter can be on the lower-half perimeter of a transparent portion of a face mask. In an example, a first and/or second air filter can be between a transparent portion of a face mask and a non-transparent portion of the face mask. In an example, a first and/or second air filter can be between an air impellor and the environment. In an example, a first and/or second air filter can be between an air impellor and the interior of the mask. In an example, a first air filter can be on a person's jaw on a first side (e.g. the right side) of a mask and a second air filter can be on the person's jaw on a second side (e.g. the left side) of the mask.

In an example, a first and/or second air filter on a face mask can have a circular, elliptical, oval, or longitudinal shape. In an example, a first and/or second air filter can be removably attached to a face mask via a clip, snap, clasp, hook, clamp, adhesive substance, or pin. In an example, a first and/or second air filter can be disposable. In an example, a first and/or second air filter can be detached from a face mask, cleaned, and then reattached to the face mask. In an example, a first and/or second air filter can comprise two filter layers, one layer between an air impellor and the environment and one layer between the air impellor and the interior of the mask (e.g. the space inside a concave transparent portion of the mask). In an example, a first and/or second air filter can further comprise a one-way airflow valve.

In an example, a mask can further comprise a sensor which tracks the cumulative airflow through a first and/or second air filter and indicates when the first and/or second air filter should be changed and/or cleaned. In an example, a mask can further comprise a sensor which tracks the level of airflow resistance through a first and/or second air filter and indicates when the first and/or second air filter should be changed and/or cleaned. In an example, there can be two air filters, wherein the mask directs airflow through a first filter until a sensor detects that the first filter is dirty, at which time the mask automatically redirects airflow through a second filter. In an example, a first and/or second air filter can further comprise two air filters, wherein the mask directs air through a second filter when the first filter becomes dirty and/or clogged.

In an example, when an air impellor is active (e.g. rotating and drawing air through an air filter) then airflow through the air filter can be: primarily or entirely from the environment to the interior of a face mask (e.g. the interior of the concavity of a transparent portion of the mask). In an example, when an air impellor is active (e.g. rotating and drawing air through an air filter) then airflow through the air filter can be: primarily or entirely from the interior of a face mask (e.g. the interior of the concavity of a transparent portion of the mask) out to the environment. In an example, when an air impellor is not active (e.g. not rotating and drawing air through an air filter), then airflow through the air filter can be: from the environment to the interior of the face mask (e.g. the interior of the concavity of a transparent portion of the mask) when the person is inhaling; and from the interior of the face mask to the environment when the person is exhaling.

In an example, a first and/or second air impellor can be selected from the group consisting of: a fan, a turbine, a propeller, a helix, and a pump. In an example, a first and/or second air impellor can rotate. In an example, a first and/or second air impellor can be rotated by an electromagnetic motor. In an example, a first and/or second air impellor can move air from the environment through one or more air filters into the interior of a face mask. In an example, a first and/or second air impellor can move air from the interior of a face mask through one or more air filters out into the environment.

In an example, the rotational speed of a first and/or second air impellor can be varied. In an example, a first and/or second air impellor can have different speed settings. In an example, a user can manually change the rotational speed of a first and/or second air impellor. In an example, a face mask can automatically change the rotational speed of a first and/or second air impellor in response to data from biometric and/or environmental sensors. In an example, a user can manually change the rotational direction of a first and/or second air impellor (and thus the direction of active airflow). In an example, a face mask can automatically change the rotational direction of a first and/or second air impellor (and thus the direction of active airflow).

In an example, a face mask can further comprise one or more sensors. In an example, the airflow of a face mask is automatically adjusted based on analysis of data from one or more sensors on the mask. In an example, the airflow of a face mask is automatically adjusted based on analysis of data from one or more biometric and/or physiological sensors on the mask. In an example, the airflow of a face mask is automatically adjusted based on analysis of data from one or more environmental sensors on the mask. In an example, a face mask can further comprise one or more sensors and the rotational speed of a first and/or second air impellor is automatically changed in response to data from the one or more sensors.

In an example, a face mask can further comprise one or more sensors which evaluate attributes of air inside the mask (e.g. oxygen level, carbon dioxide level, temperature, and/or humidity level) and the rotational speed of a first and/or second air impellor is automatically changed in response to data from the one or more sensors. In an example, a face mask can further comprise one or more sensors which evaluate attributes of air inside the mask (e.g. oxygen level, carbon dioxide level, temperature, and/or humidity level) and the rotational speed of a first and/or second air impellor is automatically increased in response to data from the one or more sensors (e.g. in response to low oxygen level, high carbon dioxide level, high or low temperature, and/or high humidity level). In an example, a face mask can further comprise one or more biometric and/or physiological sensors (e.g. pulse oximeter, EMG sensor, and/or motion sensor) and the rotational speed of a first and/or second air impellor is automatically changed in response to data from the one or more sensors.

In an example, a face mask can have: an active filtration mode (wherein movement of air through one or more air filters on the mask is caused primarily or entirely by the activation of one or more air impellors); and a passive filtration mode (wherein the air impellors are not activated and movement of air through one or more air filters on the mask is caused entirely or primarily by a person's inhalation and exhalation). In an example, a face mask can automatically switch to active filtration mode when data from biometric and/or environmental sensors indicates that a high level of air filtration and/or airflow is needed and can automatically switch to passive filtration mode when data from those sensors indicates that a high level of air filtration and/or airflow is not needed. In an example, active filtration can be initiated when the oxygen level inside the mask is low or when a wearer enters a high-risk environmental situation. In this manner, a face mask can conserve energy (and prolong battery life) by only initiating active filtration only when it is needed.

In an example, a face mask can further comprise one or more components selected from the group consisting of: data processor, power source (e.g. battery), data transmitter/receiver, biometric and/or physiological sensor, environmental sensor, microphone, speaker, interior mask light, exterior mask light, ultraviolet light emitter in optical communication with airflow within the mask, touch screen, push buttons or switches, a strap or band which loops around the back of a person's head, and a strap or band which loops over the top of a person's head. In an example, a face mask can further comprise a microphone which is in acoustic communication with the interior of the mask (e.g. with the interior of the transparent portion) and a speaker which reproduces sound recorded by the microphone. In an example, a face mask can further comprise a microphone on the inside of the mask which records a person's voice and a speaker on the outside of the mask which reproduces the person's voice. In an example, a face mask can further comprise one or more lights on the inside of the mask which highlight a person's mouth in order to increase visibility of the person's mouth (e.g. lip motion and facial expression) by nearby people. Other design variations discussed elsewhere in this disclosure or in priority-linked disclosures can also be applied to this example where relevant.

Figure 7:
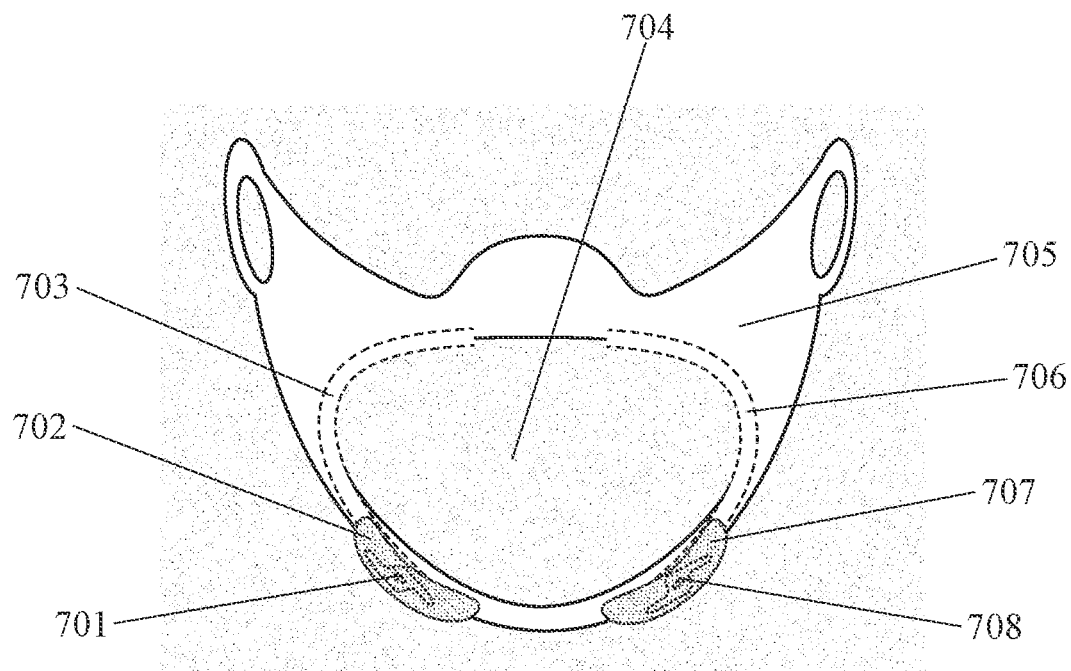
FIG. 7 shows a face mask with a transparent portion, a non-transparent portion, a first-side air filter and impellor on a person's jaw, a second-side air filter and impellor on the person's jaw, and air tubes or channels.

FIG. 7 shows an example of a face mask which is similar to the one shown in FIG. 6 except that it further comprises air tubes (e.g. air tubes, channels, or pathways) through which air flows between air filters and the interior of a transparent portion of the mask. FIG. 7 shows an example of a pathogen-filtering semi-transparent face mask comprising: a transparent portion 704 of a face mask which covers at least part of a person's mouth; a non-transparent portion 705 of the face mask which holds the transparent portion on the person's head; a first-side air filter 702 on a first side (e.g. the right side) of the mask on the person's jaw; a first-side air impellor 701 on the first side of the mask on the person's jaw which draws air through the first-side air filter; a first-side air tube (or channel) 703 between the first-side air filter and an interior space of the transparent portion; a second-side air filter 707 on a second side (e.g. the left side) of the mask on the person's jaw; a second-side air impellor 708 on the second side of the mask on the person's jaw which draws air through the second-side air filter; and a second-side air tube (or channel) 706 between the second-side air filter and an interior space of the transparent portion;

In an example, an air tube (e.g. air tube, channel, or pathway) can channel airflow between an air filter and an interior space of a transparent portion of a mask. This can be especially useful when an air filter and/or an air impellor are located relatively far away from the transparent portion of the mask for esthetic and/or other design reasons. In an example, a first air tube can channel airflow between a first air filter and an interior space of a transparent portion of a mask and a second air tube can channel airflow between a second air filter and the interior space of the transparent portion of the mask. In an example, an air tube (e.g. air tube, channel, or pathway) can span a portion of the perimeter of a transparent portion of a mask. In an example, an arcuate air tube can curve around a portion of an arcuate perimeter of a transparent portion of a mask.

In an example, an air tube in a mask can have an air-impermeable section and an air-permeable (e.g. perforated) section. In an example, the air-permeable section can have holes, openings, and perforations which allow fluid communication (e.g. air flow) with the interior space of the mask. In an example, the air-impermeable section can be closer to an air filter or air impellor and the air-permeable section can be closer to the interior space of a mask. In an example, the air-permeable section can have holes, openings, and perforations which allow fluid communication (e.g. air flow) with the interior space of transparent portion of the mask. In an example, the air-impermeable section can be closer to an air filter or air impellor and the air-permeable section can be closer to the interior space of the transparent portion of a mask.

In an example, the inner diameter of an air tube (e.g. air tube, channel, or pathway) can be within the range of ⅛" to ½". In an example, the length of an air tube can be within the range of ½" to 5". In an example, between 25% and 75% of the length of an air tube can be perforated with holes. In an example, between 50% and 80% of the length of an air tube can be perforated with holes. In an example, the interior of an air tube can have a circular cross-sectional shape. In an example, the interior of an air tube can have an elliptical, oval, and/or oblong cross-sectional shape. In an example, an air tube can be detached from a mask for cleaning and then reattached. Other design variations discussed elsewhere in this disclosure or in priority-linked disclosures can also be applied to this example where relevant.

Figure 8:
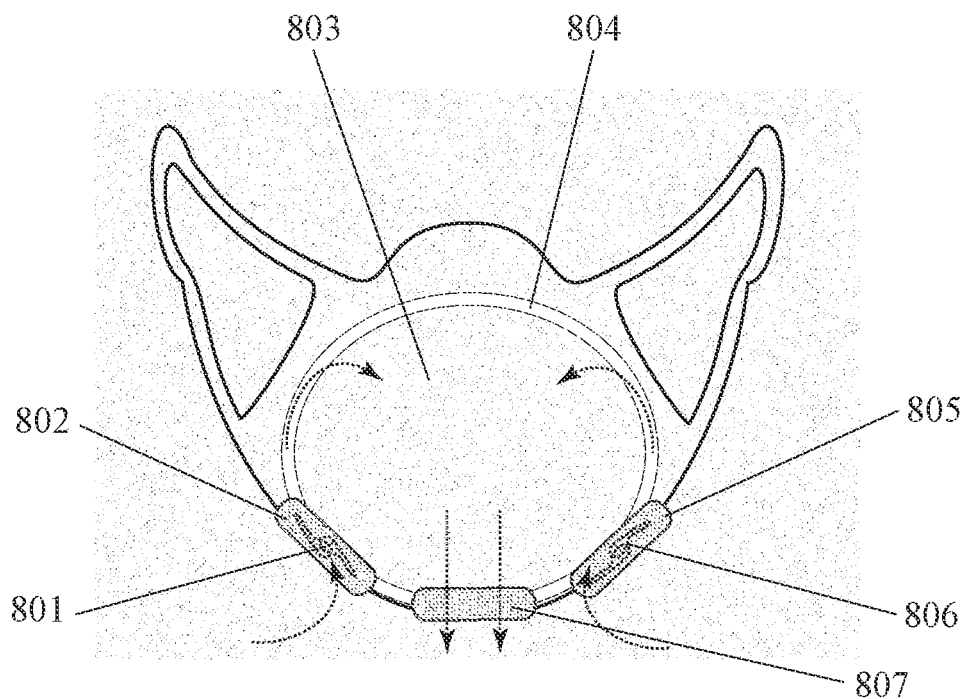
FIG. 8 shows a face mask with a transparent portion, a non-transparent portion, a first-side air filter and impellor on a person's jaw, a second-side air filter and impellor on the person's jaw, a central air filter between the first-side air filter and the second-side air filter, and air tubes or channels.

FIG. 8 shows an example of a pathogen-filtering semi-transparent face mask comprising: a transparent portion 803 of a face mask which covers at least part of a person's mouth; a first-side air filter 802 on a first side (e.g. the right side) of the mask on the person's jaw; a first-side air impellor 801 on the first side of the mask on the person's jaw which draws air into the mask from the environment through the first-side air filter; a central air filter 807 on the right-to-left central longitudinal axis of the mask on the person's jaw; a second-side air filter 805 on a second side (e.g. the left side) of the mask on the person's jaw; a second-side air impellor 806 on the second side of the mask on the person's jaw which draws air into the mask from the environment through the second-side air filter; and one or more air tubes (or channels) 804 between the first-side and second-side air filters and an interior space of the transparent portion.

In an example, when the air impellors are activated (e.g. rotating), the mask has active airflow. In an example, when the air impellors are activated (e.g. rotating), air flows from the environment into the mask through the first-side and second-side air filters and air flows out from the mask into the environment through the central air filter. In an example, when the air impellors are not activated (e.g. not rotating), then the mask has passive airflow. In an example, when the air impellors are not activated (e.g. not rotating), air flows from the environment into the mask through all of the filters when the person inhales and air flows out from the mask into the environment through all of the filters when the person exhales. Other design variations discussed elsewhere in this disclosure or in priority-linked disclosures can also be applied to this example where relevant.

Figure 9:
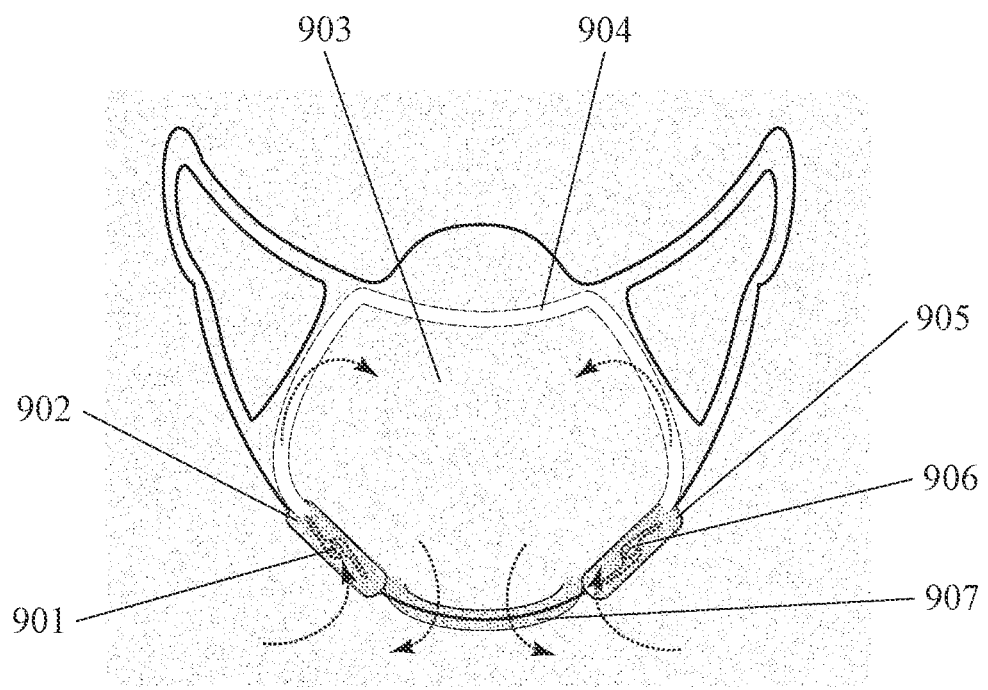
FIG. 9 shows a face mask with a transparent portion, a non-transparent portion, a first-side air filter and impellor on a person's jaw, a second-side air filter and impellor on the person's jaw, a central air filter on the perimeter of the mask between the first-side air filter and the second-side air filter, and air tubes or channels.

FIG. 9 shows an example of a face mask which is similar to the one shown in FIG. 8 except that the central air filter is longer, spanning the perimeter of the transparent portion between the first-side air filter and the second-side air filter. FIG. 9 shows an example of a pathogen-filtering semi-transparent face mask comprising: a transparent portion 903 of a face mask which covers at least part of a person's mouth; a first-side air filter 902 on a first side (e.g. the right side) of the mask on the person's jaw; a first-side air impellor 901 on the first side of the mask on the person's jaw which draws air into the mask from the environment through the first-side air filter; a second-side air filter 905 on a second side (e.g. the left side) of the mask on the person's jaw; a second-side air impellor 906 on the second side of the mask on the person's jaw which draws air into the mask from the environment through the second-side air filter; a central air filter 907 on the perimeter of the transparent portion between the first-side air filter and the second-side air filter; and one or more air tubes (or channels) 904 between the first-side and second-side air filters and an interior space of the transparent portion. Other design variations discussed elsewhere in this disclosure or in priority-linked disclosures can also be applied to this example where relevant.

Figure 10:
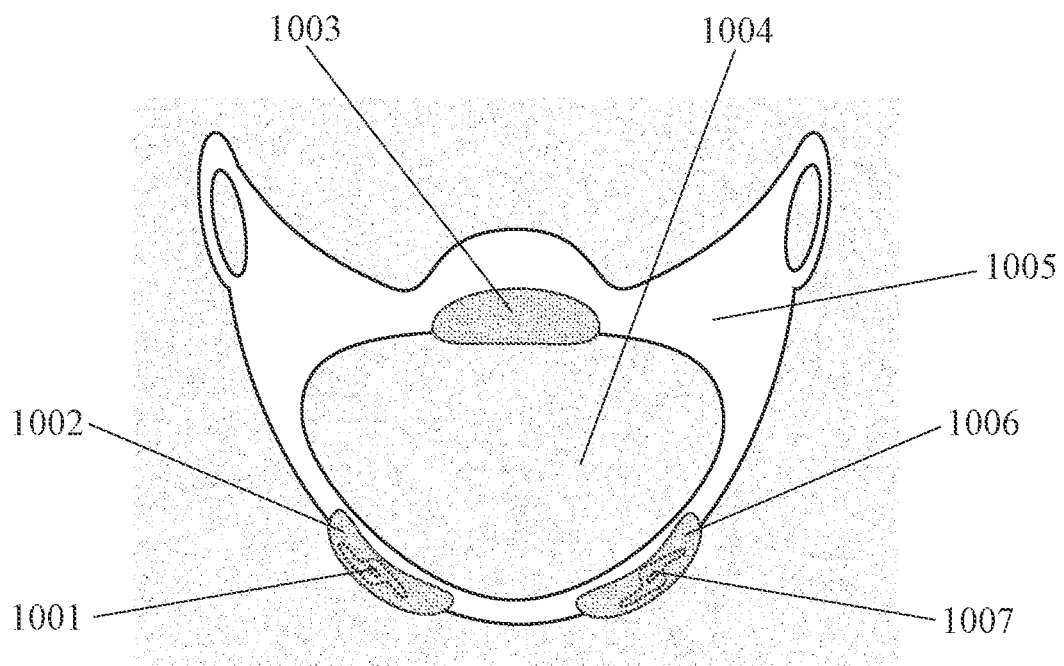
FIG. 10 shows a face mask with a transparent portion, a non-transparent portion, a first-side air filter and impellor on a person's jaw, a second-side air filter and impellor on the person's jaw, and a central air filter above the person's mouth.

FIG. 10 shows an example of a pathogen-filtering semi-transparent face mask comprising: a transparent portion 1004 of a face mask which covers at least part of a person's mouth; a non-transparent portion 1005 of the face mask which holds the transparent portion on the person's head; a first-side air filter 1002 on a first side (e.g. the right side) of the mask on the person's jaw; a first-side air impellor 1001 on the first side of the mask on the person's jaw which draws air into the mask from the environment through the first-side air filter; a second-side air filter 1006 on a second side (e.g. the left side) of the mask on the person's jaw; a second-side air impellor 1007 on the second side of the mask on the person's jaw which draws air into the mask from the environment through the second-side air filter; and an upper air filter 1003 above the person's mouth.

In an example, when the air impellors are activated (e.g. rotating), the mask has active airflow. In an example, when the air impellors are activated (e.g. rotating), air flows from the environment into the mask through the first-side and second-side air filters and air flows out from the mask into the environment through the upper air filter. In an example, when the air impellors are not activated (e.g. not rotating), then the mask has passive airflow. In an example, when the air impellors are not activated (e.g. not rotating), air flows from the environment into the mask through all of the filters when the person inhales and air flows out from the mask into the environment through all of the filters when the person exhales. Other design variations discussed elsewhere in this disclosure or in priority-linked disclosures can also be applied to this example where relevant.

Figure 11:
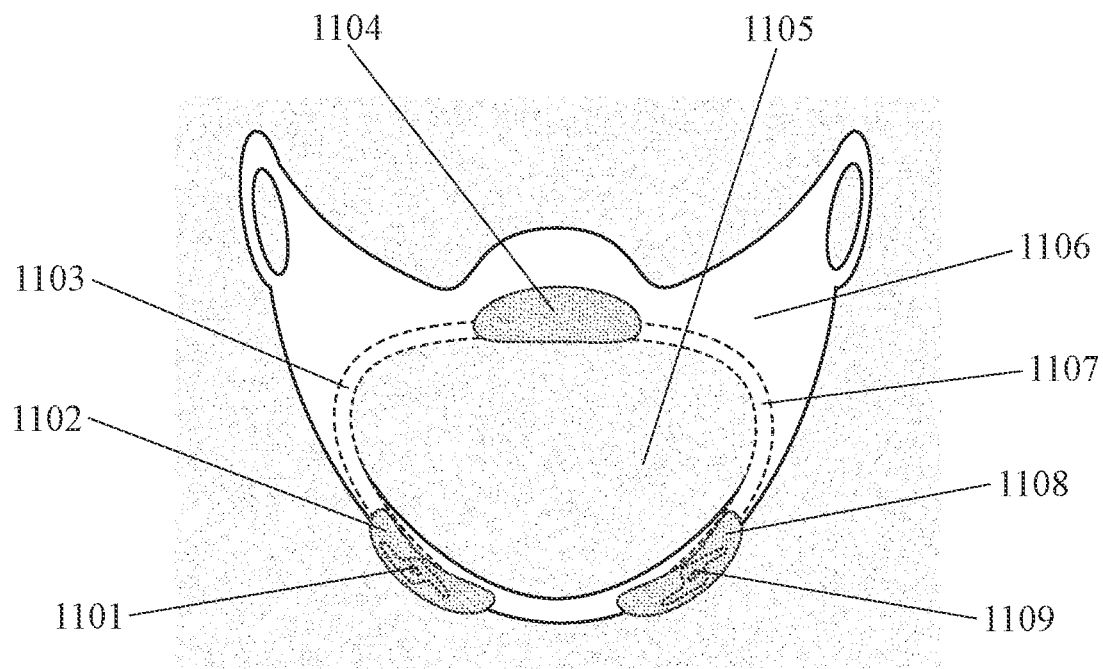
FIG. 11 shows a face mask with a transparent portion, a non-transparent portion, a first-side air filter and impellor on a person's jaw, a second-side air filter and impellor on the person's jaw, a central air filter above the person's mouth; and air tubes or channels.

FIG. 11 shows an example of a face mask which is similar to the one shown in FIG. 10 except that it further comprises air tubes (e.g. air tubes, channels, or pathways) through which air flows between air filters and the interior of a transparent portion of the mask. FIG. 11 shows an example of a pathogen-filtering semi-transparent face mask comprising: a transparent portion 1105 of a face mask which covers at least part of a person's mouth; a non-transparent portion 1106 of the face mask which holds the transparent portion on the person's head; a first-side air filter 1102 on a first side (e.g. the right side) of the mask on the person's jaw; a first-side air impellor 1101 on the first side of the mask on the person's jaw which draws air into the mask from the environment through the first-side air filter; a first-side air tube (or channel) 1103 between the first-side air filter and an interior space of the transparent portion; a second-side air filter 1108 on a second side (e.g. the left side) of the mask on the person's jaw; a second-side air impellor 1109 on the second side of the mask on the person's jaw which draws air into the mask from the environment through the second-side air filter; a second-side air tube (or channel) 1107 between the second-side air filter and an interior space of the transparent portion; and an upper air filter 1104 above the person's mouth.

In an example, when the air impellors are activated (e.g. rotating), the mask has active airflow. In an example, when the air impellors are activated (e.g. rotating), air flows from the environment into the mask through the first-side and second-side air filters and air flows out from the mask into the environment through the upper air filter. In an example, when the air impellors are not activated (e.g. not rotating), then the mask has passive airflow. In an example, when the air impellors are not activated (e.g. not rotating), air flows from the environment into the mask through all of the filters when the person inhales and air flows out from the mask into the environment through all of the filters when the person exhales. Other design variations discussed elsewhere in this disclosure or in priority-linked disclosures can also be applied to this example where relevant.

Figure 12:
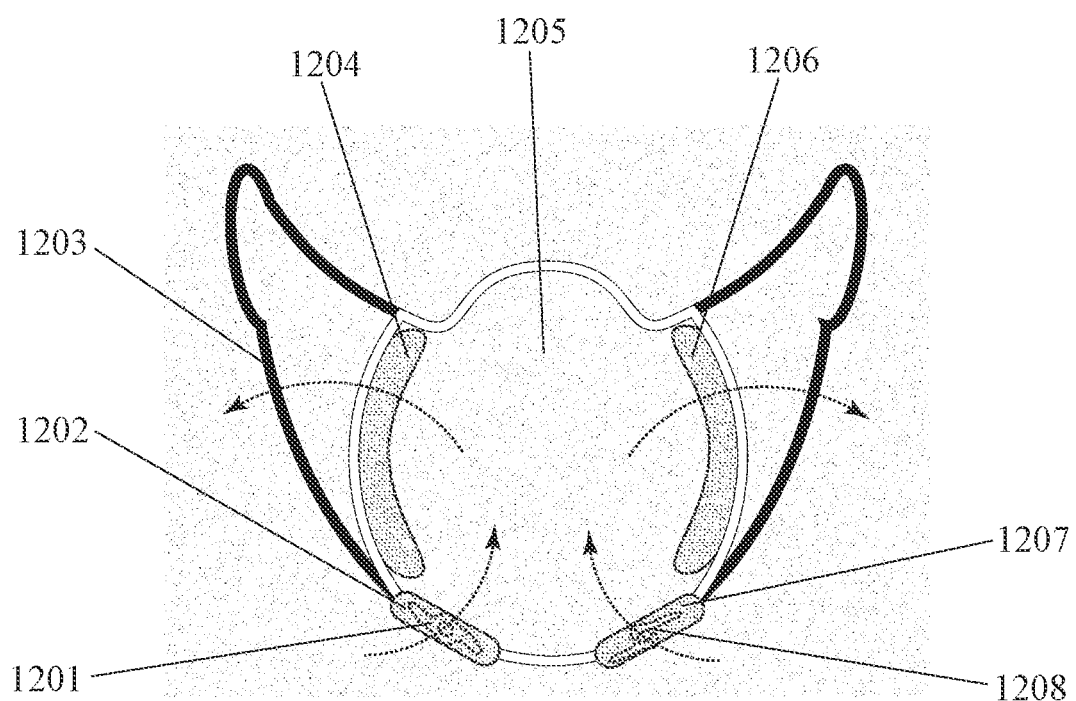
FIG. 12 shows an example of a face mask with a transparent portion, a non-transparent portion, a first-side lower air filter and impellor on a person's jaw, a second-side lower air filter and impellor on the person's jaw, a first-side upper air filter, and a second-side upper air filter.

FIG. 12 shows an example of a pathogen-filtering semi-transparent face mask comprising: a transparent portion 1205 of a face mask which covers at least part of a person's mouth; straps (including strap 1203) which hold the transparent portion on the person's head; a first-side lower air filter 1202 on a first side (e.g. the right side) of the mask on the person's jaw and/or neck; a first-side air impellor 1201 on the first side of the mask on the person's jaw which moves air through the first-side lower air filter; a first-side upper air filter 1204 on the first side of the mask which is higher than the first side lower air filter; a second-side lower air filter 1207 on a second side (e.g. the left side) of the mask on the person's jaw and/or neck; a second-side air impellor 1208 on the second side of the mask on the person's jaw which moves air through the second-side lower air filter; and a second-side upper air filter 1206 on the second side of the mask which is higher than the second side lower air filter.

In an example, a lower air filter can be on a person's jaw, chin, or neck. In an example, a lower air filter can be below a person's jaw and/or chin. In an example, a lower air filter can be on the lower-half perimeter of a transparent portion of a face mask. In an example, a lower air filter can be between a transparent portion of a face mask and a non-transparent portion of the face mask. In an example, a lower air filter can be between an air impellor and the environment. In an example, a lower air filter can be between an air impellor and the interior of the mask. In an example, a first lower air filter can be on a person's jaw on a first side (e.g. the right side) of a mask and a second lower air filter can be on the person's jaw on a second side (e.g. the left side) of the mask.

In an example, a lower air filter on a face mask can have a circular, elliptical, or oval shape. In an example, a lower air filter can be removably attached to a face mask via a clip, snap, clasp, hook, clamp, adhesive substance, or pin. In an example, a lower air filter can be disposable. In an example, a lower air filter can be detached from a face mask, cleaned, and then reattached to the face mask. In an example, a lower air filter can comprise two filter layers, one layer between an air impellor and the environment and one layer between the air impellor and the interior of the mask (e.g. the space inside a concave transparent portion of the mask). In an example, a lower air filter can further comprise a one-way airflow valve.

In an example, when an air impellor is active (e.g. rotating and drawing air through a lower air filter) then airflow through the lower air filter can be: primarily or entirely from the environment to the interior of a face mask (e.g. the interior of the concavity of a transparent portion of the mask). In an example, when an air impellor is not active (e.g. not rotating and drawing air through a lower air filter), then airflow through the lower air filter can be: from the environment in to the interior of the face mask (e.g. the interior of the concavity of a transparent portion of the mask) when the person is inhaling; and from the interior of the face mask to the environment when the person is exhaling.

In an example, an upper air filter can be to the right or left of a person's mouth. In an example, an upper air filter can be directly to the right or left of a person's mouth. In an example, an upper air filter can be on a person's cheek. In an example, an upper air filter can be on the right-side or left-side perimeter of a transparent portion of a face mask. In an example, an upper air filter can be between a transparent portion of a face mask and a non-transparent portion of the face mask. In an example, an upper air filter can curve around the right side or the left side of a transparent portion of a face mask.

In an example, an upper air filter on a face mask can have a semicircular shape. In an example, an upper air filter on a face mask can be shaped like a section of a circle, ellipse, or oval. In an example, an upper air filter can be removably attached to a face mask via a clip, snap, clasp, hook, clamp, adhesive substance, or pin. In an example, an upper air filter can be disposable. In an example, an upper air filter can be detached from a face mask, cleaned, and then reattached to the face mask. In an example, an upper air filter can further comprise a one-way airflow valve.

In an example, when an air impellor is active (e.g. rotating and drawing air through a lower air filter) then airflow through the higher air filter can be: primarily or entirely out from the interior of a face mask (e.g. the interior of the concavity of a transparent portion of the mask) to the environment. In an example, when an air impellor is not active (e.g. not rotating and drawing air through a lower air filter), then airflow through the upper air filter can be: from the environment in to the interior of the face mask (e.g. the interior of the concavity of a transparent portion of the mask)

when the person is inhaling; and from the interior of the face mask to the environment when the person is exhaling. Other design variations discussed elsewhere in this disclosure or in priority-linked disclosures can also be applied to this example where relevant.

Figure 13:
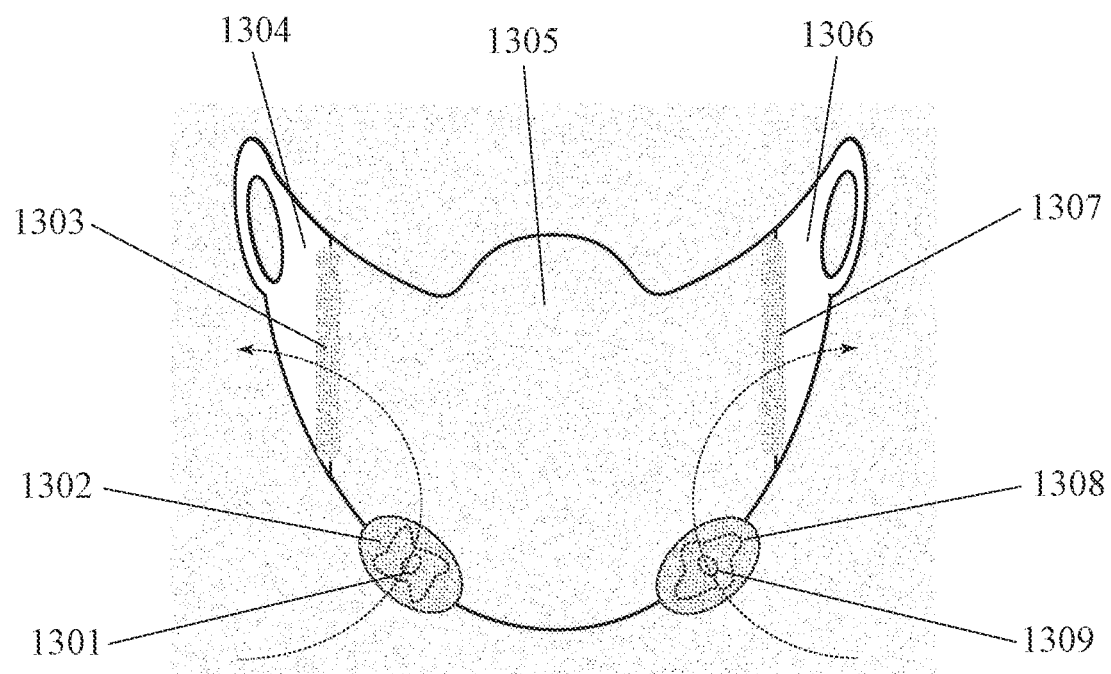
FIG. 13 shows another example of a face mask with a transparent portion, a non-transparent portion, a first-side lower air filter and impellor on a person's jaw, a second-side lower air filter and impellor on the person's jaw, a first-side upper air filter, and a second-side upper air filter.

FIG. 13 shows an example of a pathogen-filtering semi-transparent face mask comprising: a transparent portion 1305 of a face mask which covers at least part of a person's mouth; non-transparent portions 1304 and 1306 of the mask which hold the transparent portion on the person's head; a first-side lower air filter 1302 on a first side (e.g. the right side) of the mask on the person's jaw and/or neck; a first-side air impellor 1301 on the first side of the mask on the person's jaw which moves air through the first-side lower air filter; a first-side upper air filter 1303 on the first side of the mask which is higher than the first side lower air filter; a second-side lower air filter 1308 on a second side (e.g. the left side) of the mask on the person's jaw and/or neck; a second-side air impellor 1309 on the second side of the mask on the person's jaw which moves air through the second-side lower air filter; and a second-side upper air filter 1307 on the second side of the mask which is higher than the second side lower air filter.

In an example, non-transparent portions of a face mask can hold a transparent portion of a face mask on a person's head by being attached to (e.g. looping around) the person's ears. In an example, non-transparent portions can hold the transparent portion on a person's head by being attached to (e.g. looping around) the rear of the person's head. In an example, non-transparent portions can comprise elastic and/or stretchable straps, bands, cords, or strings. In an example, non-transparent portions can comprise fabric straps. In an example, non-transparent portions can be made from a flexible fabric and/or textile. In an example, non-transparent portions can be permeable to air. In an example, non-transparent portions can be impermeable to air. In an example, non-transparent portions can be less permeable to air than an air filter.

In an example, a transparent portion and non-transparent portions of a face mask can be attached to each other by sewing or weaving. In an example, a transparent portion and non-transparent portions can be attached to each other by adhesion and/or gluing. In an example, a transparent portion and non-transparent portions can be attached to each other by melting and/or welding. In an example, a transparent portion and non-transparent portions can be attached to each other by snaps, clips, clamps, hooks, pins, prongs, or buttons.

In an example, a lower air filter can be on a person's jaw, chin, or neck. In an example, a lower air filter can be below a person's jaw and/or chin. In an example, a lower air filter can be on the lower-half perimeter of a transparent portion of a face mask. In an example, a lower air filter can be between a transparent portion of a face mask and a non-transparent portion of the face mask. In an example, a lower air filter can be between an air impellor and the environment. In an example, a lower air filter can be between an air impellor and the interior of the mask. In an example, a first lower air filter can be on a person's jaw on a first side (e.g. the right side) of a mask and a second lower air filter can be on the person's jaw on a second side (e.g. the left side) of the mask.

In an example, a lower air filter on a face mask can have a circular, elliptical, or oval shape. In an example, a lower air filter can be removably attached to a face mask via a clip, snap, clasp, hook, clamp, adhesive substance, or pin. In an example, a lower air filter can be disposable. In an example, a lower air filter can be detached from a face mask, cleaned, and then reattached to the face mask. In an example, a lower air filter can comprise two filter layers, one layer between an air impellor and the environment and one layer between an air impellor and the interior of the mask (e.g. the space inside a concave transparent portion of the mask). In an example, a lower air filter can further comprise a one-way airflow valve.

In an example, when an air impellor is active (e.g. rotating and drawing air through a lower air filter) then airflow through the lower air filter can be: primarily or entirely from the environment to the interior of a face mask (e.g. the interior of the concavity of a transparent portion of the mask). In an example, when an air impellor is not active (e.g. not rotating and drawing air through a lower air filter), then airflow through the lower air filter can be: from the environment in to the interior of the face mask (e.g. the interior of the concavity of a transparent portion of the mask) when the person is inhaling; and from the interior of the face mask to the environment when the person is exhaling.

In an example, an upper air filter can be to the right or left of a person's mouth. In an example, an upper air filter can be directly to the right or left of a person's mouth. In an example, an upper air filter can be on a person's cheek. In an example, an upper air filter can be on the right-side or left-side perimeter of a transparent portion of a face mask. In an example, an upper air filter can be between a transparent portion of a face mask and a non-transparent portion of the face mask. In an example, an upper air filter can curve around the right side or the left side of a transparent portion of a face mask.

In an example, an upper air filter on a face mask can have a vertical longitudinal orientation. In an example, an upper air filter can be removably attached to a face mask via a clip, snap, clasp, hook, clamp, adhesive substance, or pin. In an example, an upper air filter can be disposable. In an example, an upper air filter can be detached from a face mask, cleaned, and then reattached to the face mask. In an example, an upper air filter can further comprise a one-way airflow valve.

In an example, when an air impellor is active (e.g. rotating and drawing air through a lower air filter) then airflow through the higher air filter can be: primarily or entirely out from the interior of a face mask (e.g. the interior of the concavity of a transparent portion of the mask) to the environment. In an example, when an air impellor is not active (e.g. not rotating and drawing air through a lower air filter), then airflow through the upper air filter can be: from the environment in to the interior of the face mask (e.g. the interior of the concavity of a transparent portion of the mask) when the person is inhaling; and from the interior of the face mask to the environment when the person is exhaling. Other design variations discussed elsewhere in this disclosure or in priority-linked disclosures can also be applied to this example where relevant.

Figure 14:
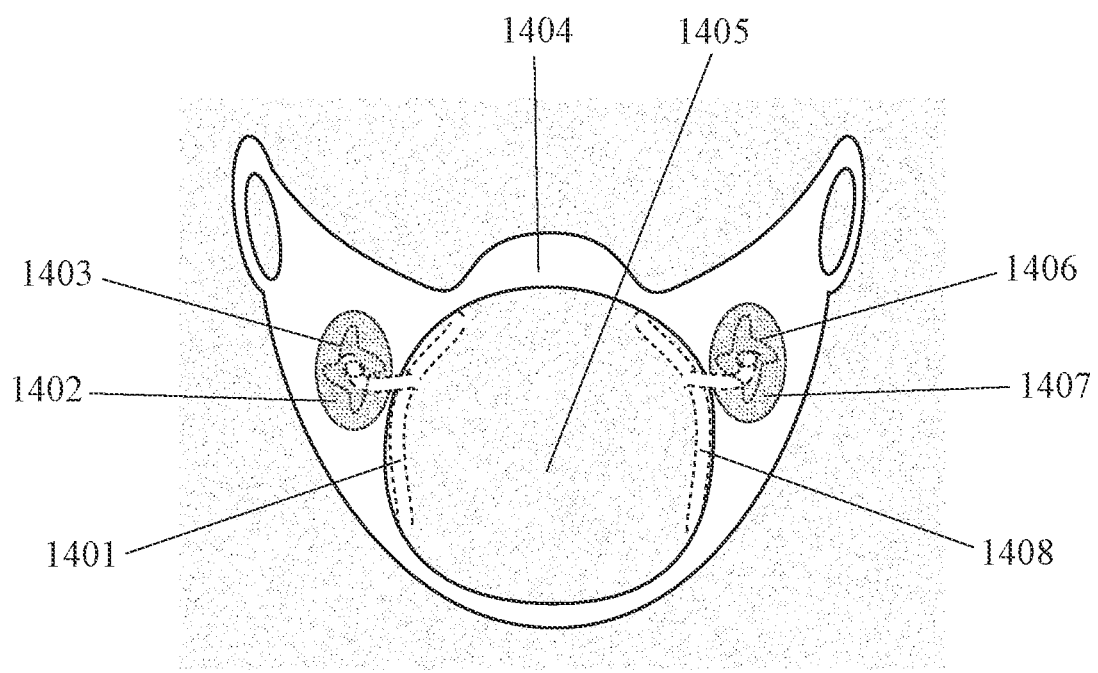
FIG. 14 shows a face mask with a transparent portion, a non-transparent portion, a first-side air filter and impellor on a person's first-side cheek, a second-side air filter and impellor on the person's second-side cheek, and air tubes or channels.

FIG. 14 shows an example of a pathogen-filtering semi-transparent face mask comprising: a transparent portion 1405 of a face mask which covers at least part of a person's mouth; a non-transparent portion 1404 of the face mask which holds the transparent portion on the person's head; a first-side air filter 1402 on a first side (e.g. the right side) of the mask over the person's cheek (e.g. between the person's mouth and an ear); a first-side air impellor 1403 on the first side of the mask on the person's jaw which moves air through the first-side air filter; a first-side air tube (or channel) 1401 between the first-side air filter and an interior space of the transparent portion; a second-side air filter 1407 on a second side (e.g. the left side) of the mask over the person's cheek (e.g. between the person's mouth and an ear); a second-side air impellor 1406 on the second side of the mask on the person's jaw which draws air through the second-side air filter; and a second-side air tube (or channel) 1408 between the second-side air filter and an interior space of the transparent portion.

In an example, a first and/or second air filter can be over (e.g. partially cover) a person's cheek. In an example, a first and/or second air filter can be between a person's mouth and an ear. In an example, a first air filter can be over a person's cheek on a first side (e.g. the right side) of a mask and a second air filter can be over the person's cheek on a second side (e.g. the left side) of the mask. In an example, a first and/or second air filter can be between an air impellor and the environment. In an example, a first and/or second air filter can be between an air impellor and the interior of the mask.

In an example, a first and/or second air filter on a face mask can have a circular, elliptical, oval, or longitudinal shape. In an example, a first and/or second air filter can be removably attached to a face mask via a clip, snap, clasp, hook, clamp, adhesive substance, or pin. In an example, a first and/or second air filter can be disposable. In an example, a first and/or second air filter can be detached from a face mask, cleaned, and then reattached to the face mask. In an example, a first and/or second air filter can comprise two filter layers, one layer between an air impellor and the environment and one layer between the air impellor and the interior of the mask (e.g. the space inside a concave transparent portion of the mask). In an example, a first and/or second air filter can further comprise a one-way airflow valve.

In an example, a mask can further comprise a sensor which tracks the cumulative airflow through a first and/or second air filter and indicates when the first and/or second air filter should be changed and/or cleaned. In an example, a mask can further comprise a sensor which tracks the level of airflow resistance through a first and/or second air filter and indicates when the first and/or second air filter should be changed and/or cleaned. In an example, there can be two air filters, wherein the mask directs airflow through a first filter until a sensor detects that the first filter is dirty, at which time the mask automatically redirects airflow through a second filter. In an example, a first and/or second air filter can further comprise two air filters, wherein the mask directs air through a second filter when the first filter becomes dirty and/or clogged.

In an example, when an air impellor is active (e.g. rotating and drawing air through an air filter) then airflow through the air filter can be: primarily or entirely from the environment to the interior of a face mask (e.g. the interior of the concavity of a transparent portion of the mask). In an example, when an air impellor is active (e.g. rotating and drawing air through an air filter) then airflow through the air filter can be: primarily or entirely from the interior of a face mask (e.g. the interior of the concavity of a transparent portion of the mask) out to the environment. In an example, when an air impellor is not active (e.g. not rotating and drawing air through an air filter), then airflow through the air filter can be: from the environment in to the interior of the face mask (e.g. the interior of the concavity of a transparent portion of the mask) when the person is inhaling; and from the interior of the face mask to the environment when the person is exhaling.

In an example, a first and/or second air impellor can be selected from the group consisting of: a fan, a turbine, a propeller, a helix, and a pump. In an example, a first and/or second air impellor can rotate. In an example, a first and/or second air impellor can be rotated by an electromagnetic motor. In an example, a first and/or second air impellor can move air from the environment through one or more air filters into the interior of a face mask. In an example, a first and/or second air impellor can move air from the interior of a face mask through one or more air filters out into the environment.

In an example, the rotational speed of a first and/or second air impellor can be varied. In an example, a first and/or second air impellor can have different speed settings. In an example, a user can manually change the rotational speed of a first and/or second air impellor. In an example, a face mask can automatically change the rotational speed of a first and/or second air impellor in response to data from biometric and/or environmental sensors. In an example, a user can manually change the rotational direction of a first and/or second air impellor (and thus the direction of active airflow). In an example, a face mask can automatically change the rotational direction of a first and/or second air impellor (and thus the direction of active airflow).

In an example, a face mask can further comprise one or more sensors. In an example, the airflow of a face mask is automatically adjusted based on analysis of data from one or more sensors on the mask. In an example, the airflow of a face mask is automatically adjusted based on analysis of data from one or more biometric and/or physiological sensors on the mask. In an example, the airflow of a face mask is automatically adjusted based on analysis of data from one or more environmental sensors on the mask. In an example, a face mask can further comprise one or more sensors and the rotational speed of a first and/or second air impellor is automatically changed in response to data from the one or more sensors.

In an example, a face mask can further comprise one or more sensors which evaluate attributes of air inside the mask (e.g. oxygen level, carbon dioxide level, temperature, and/or humidity level) and the rotational speed of a first and/or second air impellor is automatically changed in response to data from the one or more sensors. In an example, a face mask can further comprise one or more sensors which evaluate attributes of air inside the mask (e.g. oxygen level, carbon dioxide level, temperature, and/or humidity level) and the rotational speed of a first and/or second air impellor is automatically increased in response to data from the one or more sensors (e.g. in response to low oxygen level, high carbon dioxide level, high or low temperature, and/or high humidity level). In an example, a face mask can further comprise one or more biometric and/or physiological sensors (e.g. pulse oximeter, EMG sensor, and/or motion sensor) and the rotational speed of a first and/or second air impellor is automatically changed in response to data from the one or more sensors.

In an example, a face mask can have: an active filtration mode (wherein movement of air through one or more air filters on the mask is caused primarily or entirely by the activation of one or more air impellors); and a passive filtration mode (wherein the air impellors are not activated and movement of air through one or more air filters on the mask is caused entirely or primarily by a person's inhalation and exhalation). In an example, a face mask can automatically switch to active filtration mode when data from biometric and/or environmental sensors indicates that a high level of air filtration and/or airflow is needed and can automatically switch to passive filtration mode when data from those sensors indicates that a high level of air filtration and/or airflow is not needed. In an example, active filtration can be initiated when the oxygen level inside the mask is low or when a wearer enters a high-risk environmental situation. In this manner, a face mask can conserve energy (and prolong battery life) by only initiating active filtration only when it is needed.

In an example, an air tube (e.g. air tube, channel, or pathway) can channel airflow between an air filter and an interior space of a transparent portion of a mask. This can be especially useful when an air filter and/or an air impellor are located relatively far away from the transparent portion of the mask for esthetic and/or other design reasons. In an example, a first air tube can channel airflow between a first air filter and an interior space of a transparent portion of a mask and a second air tube can channel airflow between a second air filter and the interior space of the transparent portion of the mask. In an example, an air tube (e.g. air tube, channel, or pathway) can span a portion of the perimeter of a transparent portion of a mask. In an example, an arcuate air tube can curve around a portion of an arcuate perimeter of a transparent portion of a mask.

In an example, an air tube in a mask can have an air-impermeable section and an air-permeable (e.g. perforated) section. In an example, the air-permeable section can have holes, openings, and perforations which allow fluid communication (e.g. air flow) with the interior space of the mask. In an example, the air-impermeable section can be closer to an air filter or air impellor and the air-permeable section can be closer to the interior space of a mask. In an example, the air-permeable section can have holes, openings, and perforations which allow fluid communication (e.g. air flow) with the interior space of transparent portion of the mask. In an example, the air-impermeable section can be closer to an air filter or air impellor and the air-permeable section can be closer to the interior space of the transparent portion of a mask.

In an example, the inner diameter of an air tube (e.g. air tube, channel, or pathway) can be within the range of ⅛" to ½". In an example, the length of an air tube can be within the range of ½" to 5". In an example, between 25% and 75% of the length of an air tube can be perforated with holes. In an example, between 50% and 80% of the length of an air tube can be perforated with holes. In an example, the interior of an air tube can have a circular cross-sectional shape. In an example, the interior of an air tube can have an elliptical, oval, and/or oblong cross-sectional shape. In an example, an air tube can be detached from a mask for cleaning and then reattached.

In an example, a face mask can further comprise one or more components selected from the group consisting of: data processor, power source (e.g. battery), data transmitter/receiver, biometric and/or physiological sensor, environmental sensor, microphone, speaker, interior mask light, exterior mask light, ultraviolet light emitter in optical communication with airflow within the mask, touch screen, push buttons or switches, a strap or band which loops around the back of a person's head, and a strap or band which loops over the top of a person's head. In an example, a face mask can further comprise a microphone which is in acoustic communication with the interior of the mask (e.g. with the interior of the transparent portion) and a speaker which reproduces sound recorded by the microphone. In an example, a face mask can further comprise a microphone on the inside of the mask which records a person's voice and a speaker on the outside of the mask which reproduces the person's voice. In an example, a face mask can further comprise one or more lights on the inside of the mask which highlight a person's mouth in order to increase visibility of the person's mouth (e.g. lip motion and facial expression) by nearby people. Other design variations discussed elsewhere in this disclosure or in priority-linked disclosures can also be applied to this example where relevant.

Figure 15:
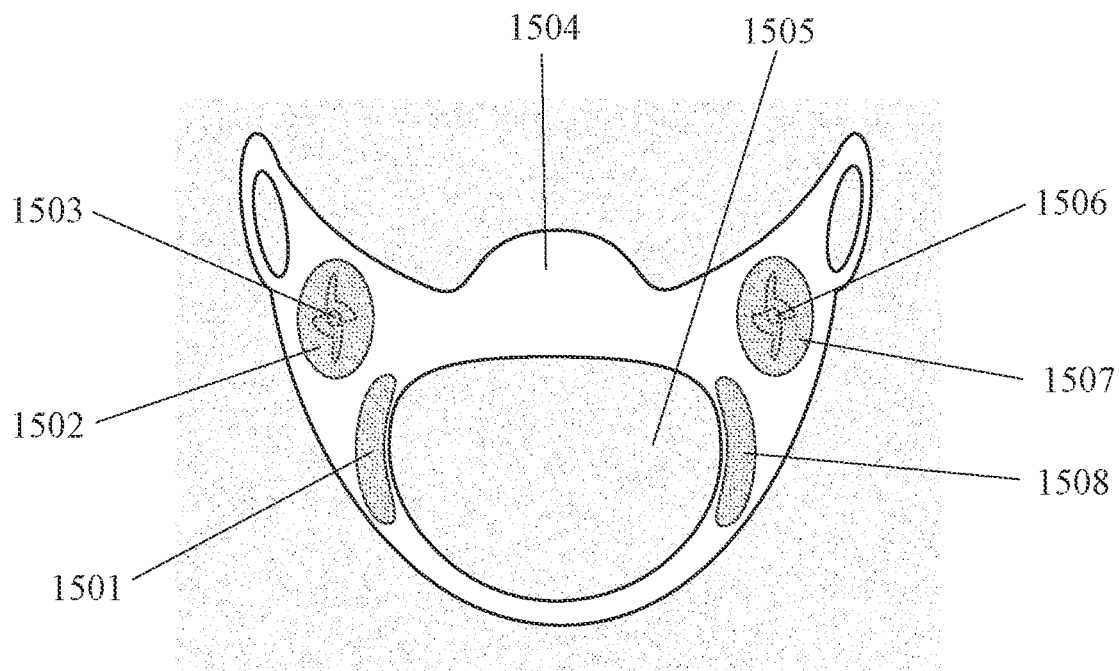
FIG. 15 shows an example of a face mask with a transparent portion, a non-transparent portion, posterior first-side and second-side air filters and impellors, and anterior first-side and second-side air filters.

FIG. 15 shows an example of a pathogen-filtering semi-transparent face mask comprising: a transparent portion 1505 of a face mask which covers at least part of a person's mouth; a non-transparent portion 1504 of the face mask which holds the transparent portion on the person's head; a posterior first-side air filter 1502 on a first side (e.g. the right side) of the mask between the person's mouth and an ear; an anterior first-side air filter 1501 on the first side of the mask between the person's mouth and an ear, wherein the anterior first-side air filter is closer to the person's mouth than the posterior first-side air filter; a first-side air impellor 1503 on the first side of the mask which moves air through the posterior first-side air filter; a posterior second-side air filter 1507 on a second side (e.g. the left side) of the mask between the person's mouth and an ear; an anterior second-side air filter 1508 on the second side of the mask between the person's mouth and an ear, wherein the anterior second-side air filter is closer to the person's mouth than the posterior second-side air filter; and a second-side air impellor 1506 on the second side of the mask which moves air through the posterior second-side air filter.

In an example, a posterior (first or second side) air filter can be between a person's mouth and an ear. In an example, a posterior air filter can be in the posterior third of the distance between a person's mouth and an ear. In an example, a posterior air filter can be in the posterior half of the distance between a person's mouth and an ear. In an example, a posterior air filter can be over (e.g. partially cover) a person's cheek. In an example, a posterior air filter can be between an air impellor and the environment. In an example, a posterior air filter can be between an air impellor and the interior of the mask. In an example, a posterior air filter on a face mask can have a circular, elliptical, or oval shape. In an example, a posterior (first or second side) air filter can be removably attached to a face mask via a clip, snap, clasp, hook, clamp, adhesive substance, or pin. In an example, a posterior air filter can be disposable. In an example, a posterior air filter can be detached from a face mask, cleaned, and then reattached to the face mask. In an example, a posterior air filter can comprise two filter layers, one layer between an air impellor and the environment and one layer between the air impellor and the interior of the mask (e.g. the space inside a concave transparent portion of the mask). In an example, a posterior air filter can further comprise a one-way airflow valve.

In an example, an anterior (first or second side) air filter can be between a person's mouth and an ear. In an example, an anterior air filter can be in the anterior third of the distance between a person's mouth and an ear. In an example, an anterior air filter can be in the anterior half of the distance between a person's mouth and an ear. In an example, an anterior air filter can be over (e.g. partially cover) a person's cheek. In an example, an anterior air filter on a face mask can have a circular, semi-circular, elliptical, or oblong shape. In an example, an anterior air filter on a face mask can curve around the right or left side perimeter of a transparent portion of a mask. In an example, an anterior air filter can be between a transparent portion of a mask and a non-transparent portion of the mask. In an example, an anterior (first or second side) air filter can be removably attached to a face mask via a clip, snap, clasp, hook, clamp, adhesive substance, or pin. In an example, an anterior air filter can be disposable. In an example, an anterior air filter can be detached from a face mask, cleaned, and then reattached to the face mask. In an example, an anterior air filter can further comprise a one-way airflow valve.

In an example, a face mask can further comprise one or more components selected from the group consisting of: data processor, power source (e.g. battery), data transmitter/receiver, biometric and/or physiological sensor, environmental sensor, microphone, speaker, interior mask light, exterior mask light, ultraviolet light emitter in optical communication with airflow within the mask, touch screen, push buttons or switches, a strap or band which loops around the back of a person's head, and a strap or band which loops over the top of a person's head. In an example, a face mask can further comprise a microphone which is in acoustic communication with the interior of the mask (e.g. with the interior of the transparent portion) and a speaker which reproduces sound recorded by the microphone. In an example, a face mask can further comprise a microphone on the inside of the mask which records a person's voice and a speaker on the outside of the mask which reproduces the person's voice. In an example, a face mask can further comprise one or more lights on the inside of the mask which highlight a person's mouth in order to increase visibility of the person's mouth (e.g. lip motion and facial expression) by nearby people. Other design variations discussed elsewhere in this disclosure or in priority-linked disclosures can also be applied to this example where relevant.

Figure 16:
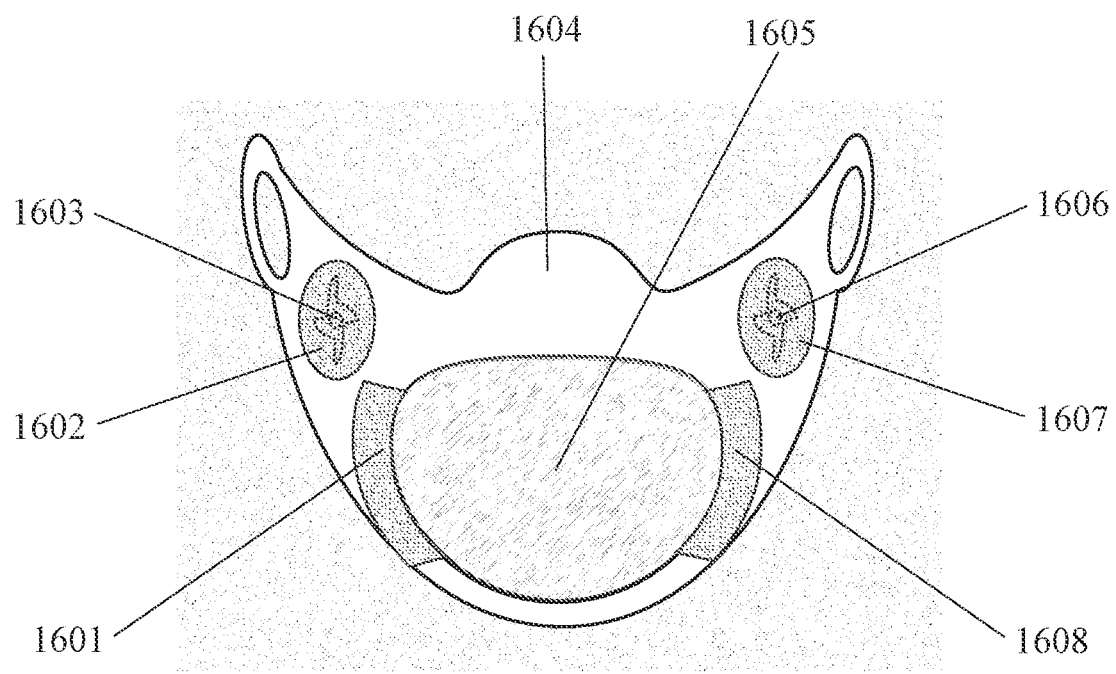
FIG. 16 shows another example of a face mask with a transparent portion, a non-transparent portion, a posterior first-side and second-side air filters and impellors, and anterior first-side and second-side air filters.

FIG. 16 shows an example of a face mask which is similar to the one shown in FIG. 15 except that the anterior right-side and left-side filters curve around the right-side and left-side perimeters, respectively, of the transparent portion of the mask. FIG. 16 shows an example of a pathogen-filtering semi-transparent face mask comprising: a transparent portion 1605 of a face mask which covers at least part of a person's mouth; a non-transparent portion 1604 of the face mask which holds the transparent portion on the person's head; a posterior first-side air filter 1602 on a first side (e.g. the right side) of the mask between the person's mouth and an ear; an anterior first-side air filter 1601 on the first side of the mask between the person's mouth and an ear, wherein the anterior first-side air filter is closer to the person's mouth than the posterior first-side air filter, and wherein the anterior first-side air filter is along the first side of the perimeter of the transparent portion; a first-side air impellor 1603 on the first side of the mask which moves air through the posterior first-side air filter; a posterior second-side air filter 1607 on a second side (e.g. the left side) of the mask between the person's mouth and an ear; an anterior second-side air filter 1608 on the second side of the mask between the person's mouth and an ear, wherein the anterior second-side air filter is closer to the person's mouth than the posterior second-side air filter, and wherein the anterior second-side air filter is along the second side of the perimeter of the transparent portion; and a second-side air impellor 1606 on the second side of the mask which moves air through the posterior second-side air filter. Other design variations discussed elsewhere in this disclosure or in priority-linked disclosures can also be applied to this example where relevant.

Figure 17:
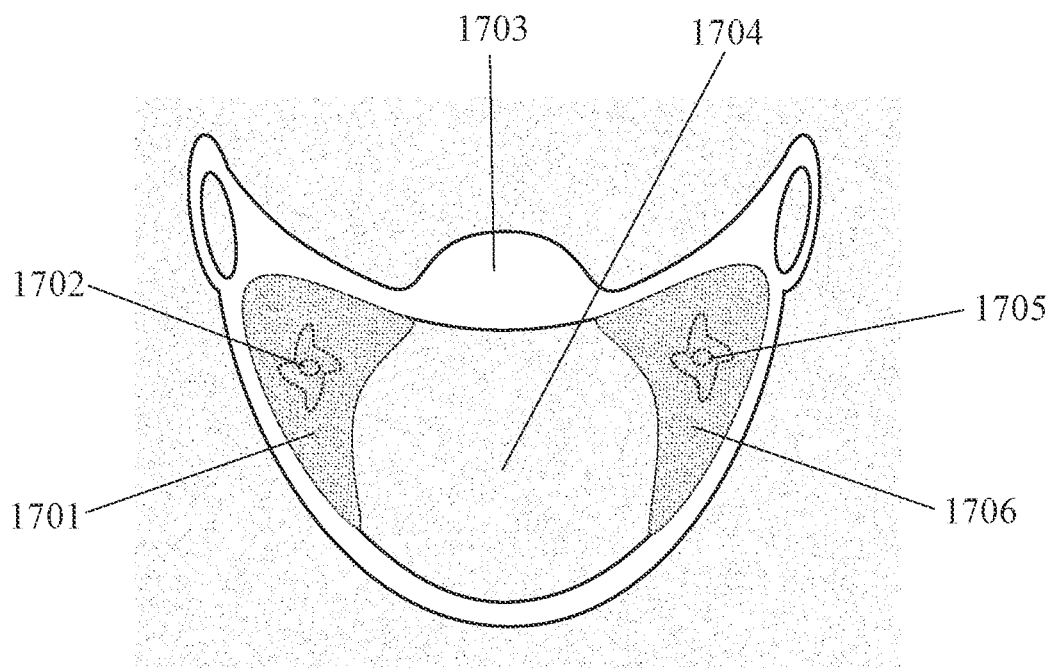
FIG. 17 shows a face mask with a transparent portion, a non-transparent portion, first-side and second-side air filters adjacent to the transparent portion, and first-side and second-side air impellors.

FIG. 17 shows an example of a pathogen-filtering semi-transparent face mask comprising: a transparent portion 1704 of a face mask which covers at least part of a person's mouth; a non-transparent portion 1703 of the face mask which holds the transparent portion on the person's head; a first-side air filter 1701 on a first side (e.g. the right side) of the mask between the person's mouth and an ear, wherein the first-side air filter is adjacent to the transparent portion; a first-side air impellor 1702 on the first side of the mask which moves air through the first-side air filter; a second-side air filter 1706 on a second side (e.g. the left side) of the mask between the person's mouth and an ear, wherein the second-side air filter is adjacent to the transparent portion; and a second-side air impellor 1705 on the second side of the mask which moves air through the second-side air filter.

In an example, a (first or second) side air filter can be adjacent to the (first or second) side perimeter of a transparent portion of the mask. In an example, a (first or second) side air filter can be contiguous to the (first or second) side perimeter of the transparent portion. In an example, a (first or second) side air filter can curve around the (first or second) side perimeter of the transparent portion. In an example, a (first or second) side air filter can span between 10% and 50% of the perimeter of the transparent portion. In an example, a (first or second) side air filter can span between 20% and 40% of the perimeter of the transparent portion. In an example, a (first or second) side air filter can span between 20% and 80% of the distance between a person's mouth and an ear. In an example, a (first or second) side air filter can span between 20% and 80% of the distance between a person's nose and the bottom of their jaw. In an example, a (first or second) side air filter can have a shape selected from the group consisting of: conic section; rounded arrowhead shape; StarTrek™ communications badge shape (OK, so I am nerd, but that is what it looks like to me); and Nike™ logo swoosh shape (OK, so I know a little about sports logos, but I am still a nerd). Other design variations discussed elsewhere in this disclosure or in priority-linked disclosures can also be applied to this example where relevant.

Figure 18:
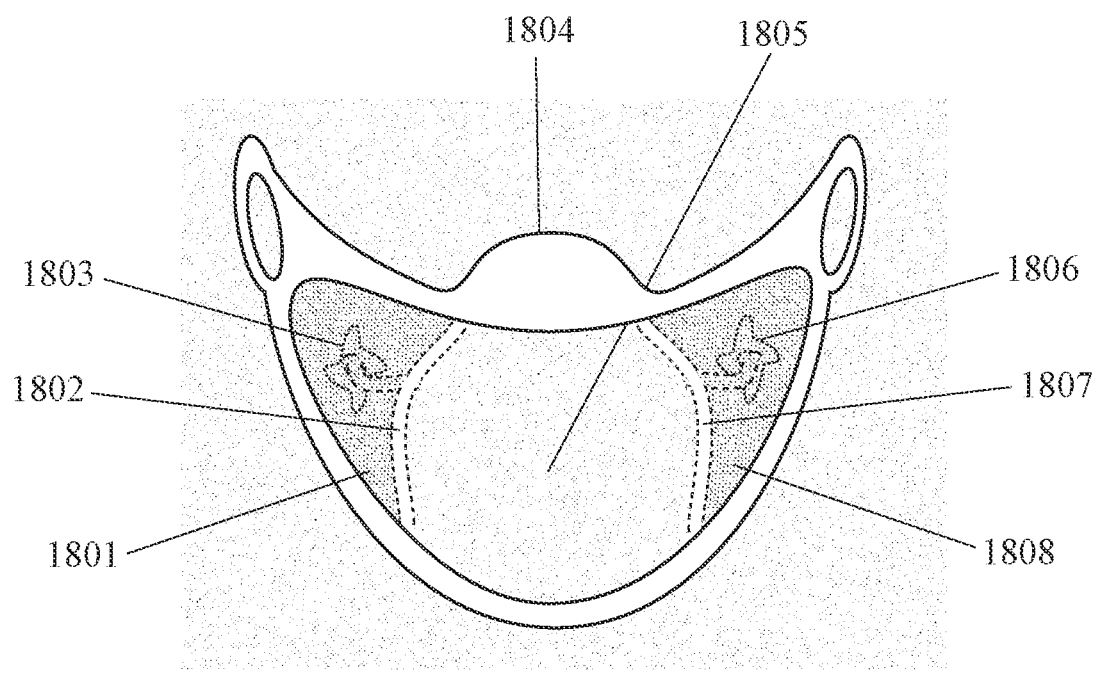
FIG. 18 shows a face mask with a transparent portion, a non-transparent portion, first-side and second-side air filters adjacent to the transparent portion, first-side and second-side air impellors, and air tubes or channels.

FIG. 18 shows an example of a face mask which is similar to the one shown in FIG. 17 except that it includes air tubes (or channels) which direct airflow between air filters and the transparent portion of the mask. FIG. 18 shows an example of a pathogen-filtering semi-transparent face mask comprising: a transparent portion 1805 of a face mask which covers at least part of a person's mouth; a non-transparent portion 1804 of the face mask which holds the transparent portion on the person's head; a first-side air filter 1801 on a first side (e.g. the right side) of the mask between the person's mouth and an ear, wherein the first-side air filter is adjacent to the transparent portion; a first-side air impellor 1803 on the first side of the mask which moves air through the first-side air filter; a first-side air tube (or channel) 1802 which directs airflow between the first-side air filter and the transparent portion; a second-side air filter 1808 on a second side (e.g. the left side) of the mask between the person's mouth and an ear, wherein the second-side air filter is adjacent to the transparent portion; a second-side air impellor 1806 on the second side of the mask which moves air through the second-side air filter; and a second-side air tube (or channel) 1807 which directs airflow between the second-side air filter and the transparent portion.

In an example, a (first or second) side air filter can be adjacent to the (first or second) side perimeter of a transparent portion of the mask. In an example, a (first or second) side air filter can be contiguous to the (first or second) side perimeter of the transparent portion. In an example, a (first or second) side air filter can curve around the (first or second) side perimeter of the transparent portion. In an example, a (first or second) side air filter can span between 10% and 50% of the perimeter of the transparent portion. In an example, a (first or second) side air filter can span between 20% and 40% of the perimeter of the transparent portion. In an example, a (first or second) side air filter can span between 20% and 80% of the distance between a person's mouth and an ear. In an example, a (first or second) side air filter can span between 20% and 80% of the distance between a person's nose and the bottom of their jaw. In an example, a (first or second) side air filter can have a shape selected from the group consisting of: conic section; rounded arrowhead shape; StarTrek™ communications badge shape (OK, so I am nerd, but that is what it looks like to me); and Nike™ logo swoosh shape (OK, so I know a little about sports logos, but I am still a nerd).

In an example, an air tube (e.g. air tube, channel, or pathway) can channel airflow between an air filter and an interior space of a transparent portion of a mask. This can be especially useful when an air filter and/or an air impellor are located relatively far away from the transparent portion of the mask for esthetic and/or other design reasons. In an example, a first air tube can channel airflow between a first air filter and an interior space of a transparent portion of a mask and a second air tube can channel airflow between a second air filter and the interior space of the transparent portion of the mask. In an example, an air tube (e.g. air tube, channel, or pathway) can span a portion of the perimeter of a transparent portion of a mask. In an example, an arcuate air tube can curve around a portion of an arcuate perimeter of a transparent portion of a mask.

In an example, an air tube in a mask can have an air-impermeable section and an air-permeable (e.g. perforated) section. In an example, the air-permeable section can have holes, openings, and perforations which allow fluid communication (e.g. air flow) with the interior space of the mask. In an example, the air-impermeable section can be closer to an air filter or air impellor and the air-permeable section can be closer to the interior space of a mask. In an example, the air-permeable section can have holes, openings, and perforations which allow fluid communication (e.g. air flow) with the interior space of transparent portion of the mask. In an example, the air-impermeable section can be closer to an air filter or air impellor and the air-permeable section can be closer to the interior space of the transparent portion of a mask.

In an example, the inner diameter of an air tube (e.g. air tube, channel, or pathway) can be within the range of ⅛" to ½". In an example, the length of an air tube can be within the range of ½" to 5". In an example, between 25% and 75% of the length of an air tube can be perforated with holes. In an example, between 50% and 80% of the length of an air tube can be perforated with holes. In an example, the interior of an air tube can have a circular cross-sectional shape. In an example, the interior of an air tube can have an elliptical, oval, and/or oblong cross-sectional shape. In an example, an air tube can be detached from a mask for cleaning and then reattached. Other design variations discussed elsewhere in this disclosure or in priority-linked disclosures can also be applied to this example where relevant.

Figure 19:
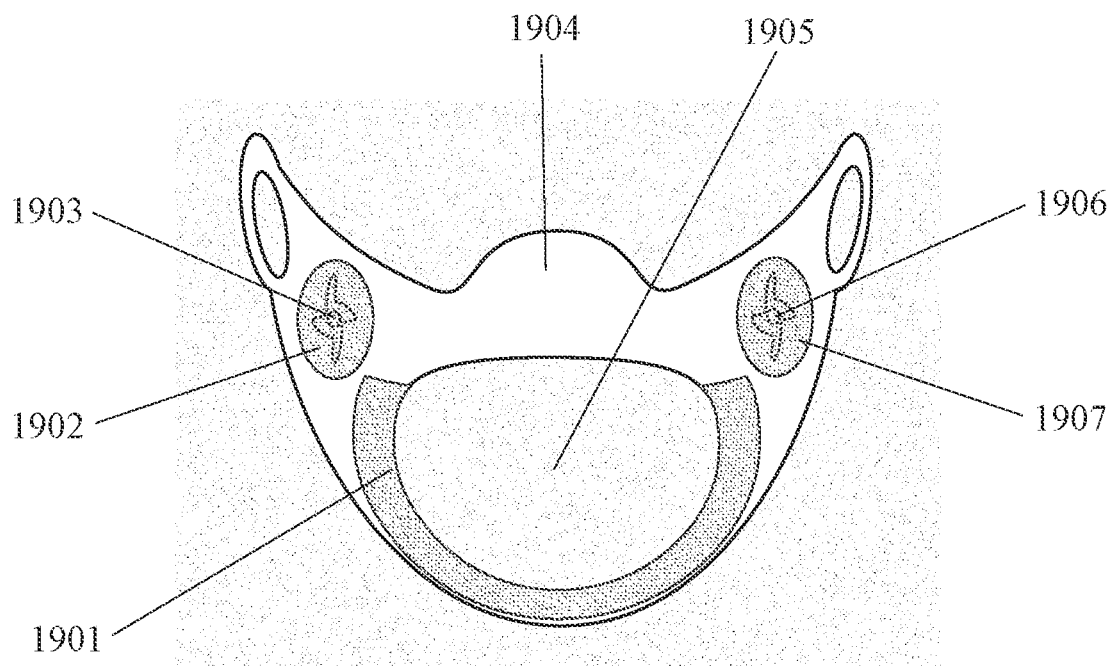
FIG. 19 shows a face mask with a transparent portion, a non-transparent portion, first-side and second-side air filters and impellors, and a concave air filter.

FIG. 19 shows an example of a pathogen-filtering semi-transparent face mask comprising: a transparent portion 1905 of a face mask which covers at least part of a person's mouth; a non-transparent portion 1904 of the face mask which holds the transparent portion on the person's head; a first-side air filter 1902 on a first side (e.g. the right side) of the mask between the person's mouth and an ear; a first-side air impellor 1903 on the first side of the mask which moves air through the first-side air filter; a second-side air filter 1907 on a second side (e.g. the left side) of the mask between the person's mouth and an ear; a second-side air impellor 1906 on the second side of the mask which moves air through the second-side air filter; and a concave air filter 1901 with a concavity which opens upwards toward the person's mouth.

In an example, a concave air filter can have a concavity which opens upwards toward a person's mouth. In an example, at least a part of a person's mouth enclosed within and/or surrounded by the concavity of a concave air filter. In an example, a lower portion of a concave air filter can be below a person's mouth. In an example, a lower portion of a concave air filter can be on a person's jaw and/or chin. In an example, a lower portion of a concave air filter can be along a person's jaw and/or chin. In an example, a concave air filter can span from a first side (e.g. the right side) of a transparent portion of a mask to a second side (e.g. the left side) of the transparent portion. In an example, a concave air filter can span the perimeter of a transparent portion of a mask from a first side (e.g. the right side) of the transparent portion to a second side (e.g. the left side) of the transparent portion. In an example, a concave air filter can have a smile shape which could cause the wearer to be mistaken for Pikachu.

In an example, a concave air filter can span half of the perimeter of a transparent portion of a mask. In an example, a concave air filter can span between 15% and 60% of the perimeter of a transparent portion of a mask. In an example, a concave air filter can span two-third of the perimeter of a transparent portion of a mask. In an example, a concave air filter can span between 30% and 75% of the perimeter of a transparent portion of a mask. In an example, a concave air filter can have a width within the range of ¼" to 1". In an example, a concave air filter can have an arcuate length within the range of ¾" to 6". Other design variations discussed elsewhere in this disclosure or in priority-linked disclosures can also be applied to this example where relevant.

Figure 20:
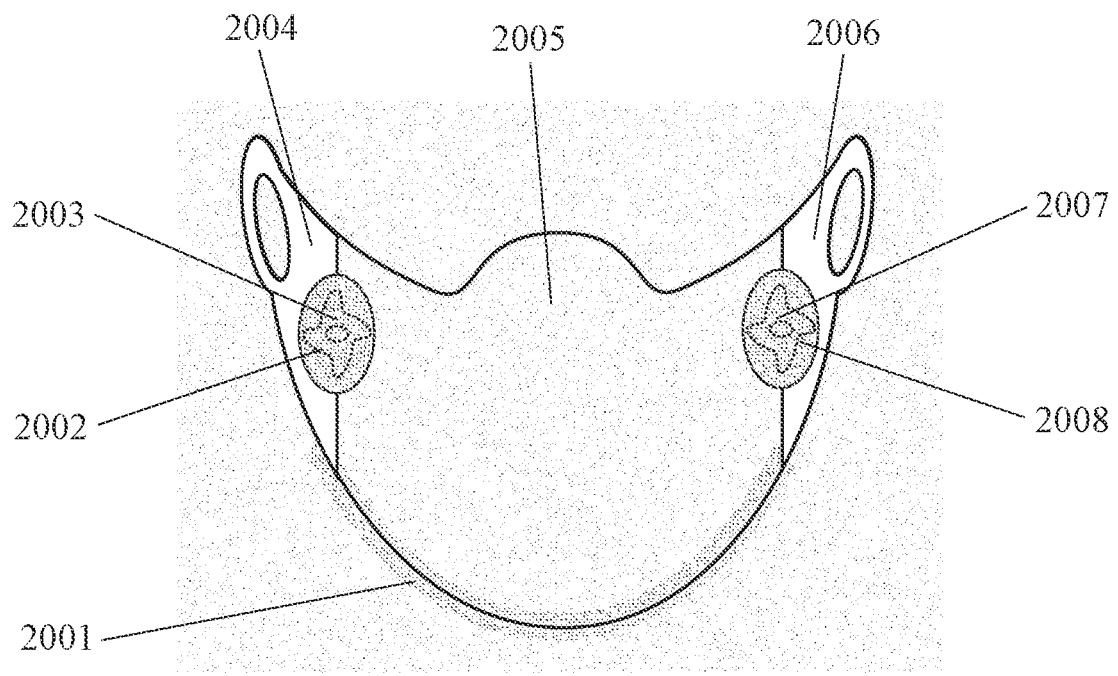
FIG. 20 shows a face mask with a transparent portion, a non-transparent portion, first-side and second-side air filters and impellors, and a lower perimeter air filter.

FIG. 20 shows an example of a pathogen-filtering semi-transparent face mask comprising: a transparent portion 2005 of a face mask which covers at least part of a person's mouth; non-transparent portions 2004 and 2006 of the face mask which hold the transparent portion on the person's head; a first-side air filter 2002 on a first side (e.g. the right side) of the transparent portion; a first-side air impellor 2003 which moves air through the first-side air filter; a second-side air filter 2008 on a second side (e.g. the left side) of the transparent portion; a second-side air impellor 2007 which moves air through the second-side air filter; and a concave air filter 2001 with a concavity which opens upwards toward the person's mouth.

In an example, a concave air filter can have a concavity which opens upwards toward a person's mouth. In an example, at least a part of a person's mouth enclosed within and/or surrounded by the concavity of a concave air filter. In an example, a lower portion of a concave air filter can be below a person's mouth. In an example, a lower portion of a concave air filter can be on a person's jaw and/or chin. In an example, a lower portion of a concave air filter can be along a person's jaw and/or chin. In an example, a concave air filter can span from a first side (e.g. the right side) of a transparent portion of a mask to a second side (e.g. the left side) of the transparent portion. In an example, a concave air filter can span the perimeter of a transparent portion of a mask from a first side (e.g. the right side) of the transparent portion to a second side (e.g. the left side) of the transparent portion. In an example, a concave air filter can have a smile shape.

In an example, a concave air filter can span half of the perimeter of a transparent portion of a mask. In an example, a concave air filter can span between 15% and 60% of the perimeter of a transparent portion of a mask. In an example, a concave air filter can span two-third of the perimeter of a transparent portion of a mask. In an example, a concave air filter can span between 30% and 75% of the perimeter of a transparent portion of a mask. In an example, a concave air filter can have a width within the range of ¼" to 1". In an example, a concave air filter can have an arcuate length within the range of ¾" to 6". Other design variations discussed elsewhere in this disclosure or in priority-linked disclosures can also be applied to this example where relevant.

Figure 21:
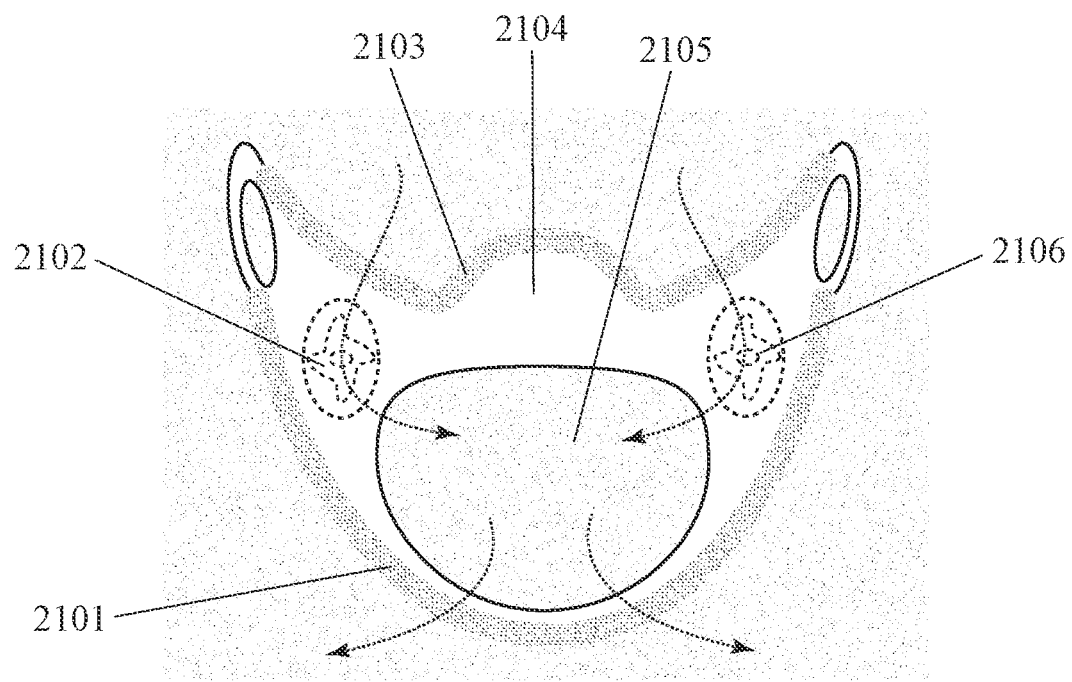
FIG. 21 shows a face mask with a transparent portion, a non-transparent portion, first-side and second-side air filters and impellors, an upper-perimeter air filter, and a lower-perimeter air filter.

FIG. 21 shows an example of a pathogen-filtering semi-transparent face mask comprising: a transparent portion 2105 of a face mask which covers at least part of a person's mouth; a non-transparent portion 2104 of the face mask which holds the transparent portion on the person's head; an upper-perimeter air filter 2103 which spans at least part of the upper perimeter of the mask, including a portion of the mask perimeter around the person's nose; a lower-perimeter air filter 2101 which spans at least part of the lower perimeter of the mask, including a portion of the mask perimeter around the person's jaw and/or chin; a first-side air impellor 2102 which draws air into the mask through the upper-perimeter air filter; and a second-side air filter 2106 which draws air into the mask through the upper-perimeter air filter.

In an example, an upper perimeter air filter can be a single continuous air filter which spans from a first side (e.g. the right side) of a mask to a second side (e.g. the left side) of the mask. In an example, an upper perimeter air filter can comprise two separate air filters, one on a first side (e.g. the right side) of a mask and one on a second side (e.g. the left side) of the mask. In an example, an upper perimeter air filter can comprise two separate air filters, one to a first side (e.g. to the right) of a person's nose and one to a second side (e.g. to the left) of the person's nose. In an example, an upper perimeter air filter can span between 30% and 50% of the upper perimeter of a mask. In an example, an upper perimeter air filter can span between 30% and 50% of the upper perimeter of a mask between a person's ears. In an example, an upper perimeter air filter can span between 20% and 90% of the upper perimeter of a mask. In an example, an upper perimeter air filter can span between 20% and 90% of the upper perimeter of a mask between a person's ears.

In an example, a lower perimeter air filter can be a single continuous air filter which spans from a first side (e.g. the right side) of a mask to a second side (e.g. the left side) of the mask. In an example, a lower perimeter air filter can comprise two separate air filters, one on a first side (e.g. the right side) of a mask and one on a second side (e.g. the left side) of the mask. In an example, a lower perimeter air filter can comprise two separate air filters, one to a first side (e.g. to the right) of a person's chin and one to a second side (e.g. to the left) of the person's chin. In an example, a lower perimeter air filter can span between 30% and 50% of the lower perimeter of a mask. In an example, a lower perimeter air filter can span between 30% and 50% of the lower perimeter of a mask along a person's jaw. In an example, a lower perimeter air filter can span between 20% and 90% of the lower perimeter of a mask. In an example, a lower perimeter air filter can span between 20% and 90% of the lower perimeter of a mask along a person's jaw. Other design variations discussed elsewhere in this disclosure or in priority-linked disclosures can also be applied to this example where relevant.

Figure 22:
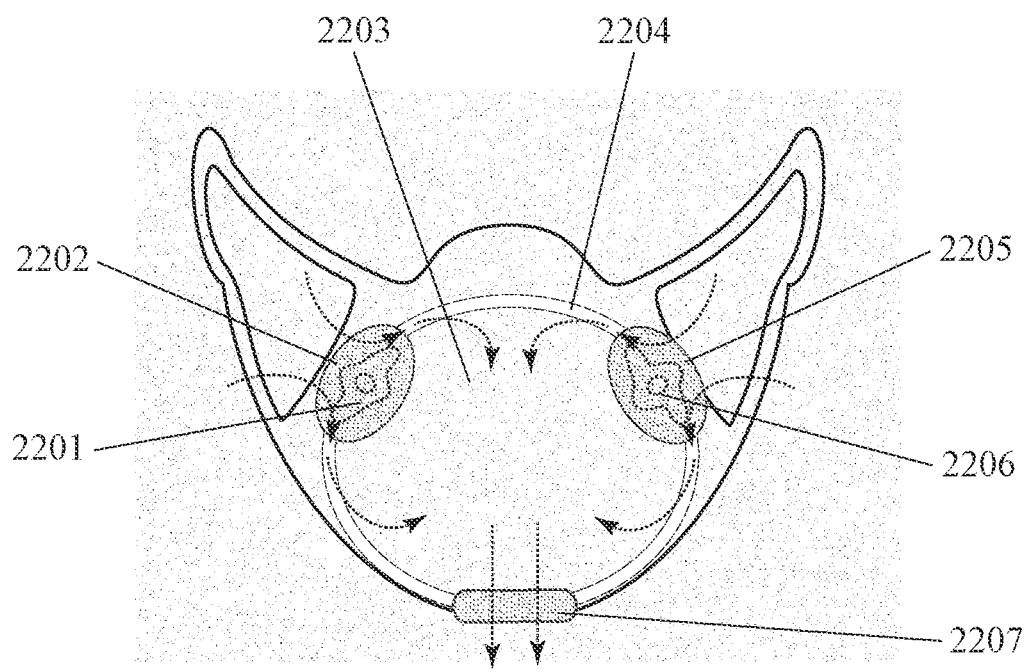
FIG. 22 shows a face mask with a transparent portion, first-side and second-side air filters and impellors, a lower air filter below the person's mouth, and air tubes or channels.

FIG. 22 shows an example of a pathogen-filtering semi-transparent face mask comprising: a transparent portion 2203 of a face mask which covers at least part of a person's mouth; a first-side air filter 2202 on a first side (e.g. the right side) of the mask between the person's mouth and an ear; a first-side air impellor 2201 which moves air through the first-side air filter; a second-side air filter 2205 on a second side (e.g. the left side) of the mask between the person's mouth and an ear; a second-side air impellor 2206 which moves air through the second-side air filter; an air tube (or channel) 2204 which directs airflow between the first-side air filter and/or the second-side air filter and the transparent portion; and a lower air filter 2207 below the person's mouth.

In an example, an air tube (e.g. air tube, channel, or pathway) can channel airflow between one or more air filters and an interior space of a transparent portion of a mask. This can be especially useful when an air filter and/or an air impellor are located relatively far away from the transparent portion of the mask for esthetic and/or other design reasons. In an example, a first air tube can channel airflow between a first air filter and an interior space of a transparent portion of a mask and a second air tube can channel airflow between a second air filter and the interior space of the transparent portion of the mask. In an example, an air tube (e.g. air tube, channel, or pathway) can span a portion of the perimeter of a transparent portion of a mask. In an example, an arcuate air tube can curve around a portion of an arcuate perimeter of a transparent portion of a mask.

In an example, an air tube in a mask can have an air-impermeable section and an air-permeable (e.g. perforated) section. In an example, the air-permeable section can have holes, openings, and perforations which allow fluid communication (e.g. air flow) with the interior space of the mask. In an example, the air-impermeable section can be closer to an air filter or air impellor and the air-permeable section can be closer to the interior space of a mask. In an example, the air-permeable section can have holes, openings, and perforations which allow fluid communication (e.g. air flow) with the interior space of transparent portion of the mask. In an example, the air-impermeable section can be closer to an air filter or air impellor and the air-permeable section can be closer to the interior space of the transparent portion of a mask.

In an example, the inner diameter of an air tube (e.g. air tube, channel, or pathway) can be within the range of ⅛" to ½". In an example, the length of an air tube can be within the range of ½" to 5". In an example, between 25% and 75% of the length of an air tube can be perforated with holes. In an example, between 50% and 80% of the length of an air tube can be perforated with holes. In an example, the interior of an air tube can have a circular cross-sectional shape. In an example, the interior of an air tube can have an elliptical, oval, and/or oblong cross-sectional shape. In an example, an air tube can be detached from a mask for cleaning and then reattached.

In an example, an air filter can have a circular shape. In an example, an air filter can have an arcuate shape. In an example, an air filter can be removably attached to a face mask via a clip, snap, clasp, hook, clamp, adhesive substance, or pin. In an example, an air filter can be disposable. In an example, an air filter can be detached from a face mask, cleaned, and then reattached to the face mask. In an example, an air filter can be located along the perimeter of a transparent portion of a face mask. In an example, a side air filter can be located between a person's mouth and an ear. In an example, a lower air filter can be located in the lower half of the transparent portion of a face mask. In an example, a lower air filter can be located on a person's jaw and/or chin. In an example, an air filter can be located below a person's jaw and/or chin.

In an example, when the first-side air impellor and/or second-side air impellor are in operation then: airflow through the first-side air filter and/or second-side air filter can be primarily (or entirely) from the environment into the interior of the mask; and airflow through the lower air filter can be primarily (or entirely) from the interior of the mask out into environment. In an example, when the first-side air impellor and second-side air impellor are not in operation then: airflow through the first-side air filter, the second-side air filter, and/or the lower air filter can be primarily (or entirely) from the environment into the interior of the mask when the person inhales and primarily (or entirely) from the interior of the mask out into environment when the person exhales. Other design variations discussed elsewhere in this disclosure or in priority-linked disclosures can also be applied to this example where relevant.

Figure 23:
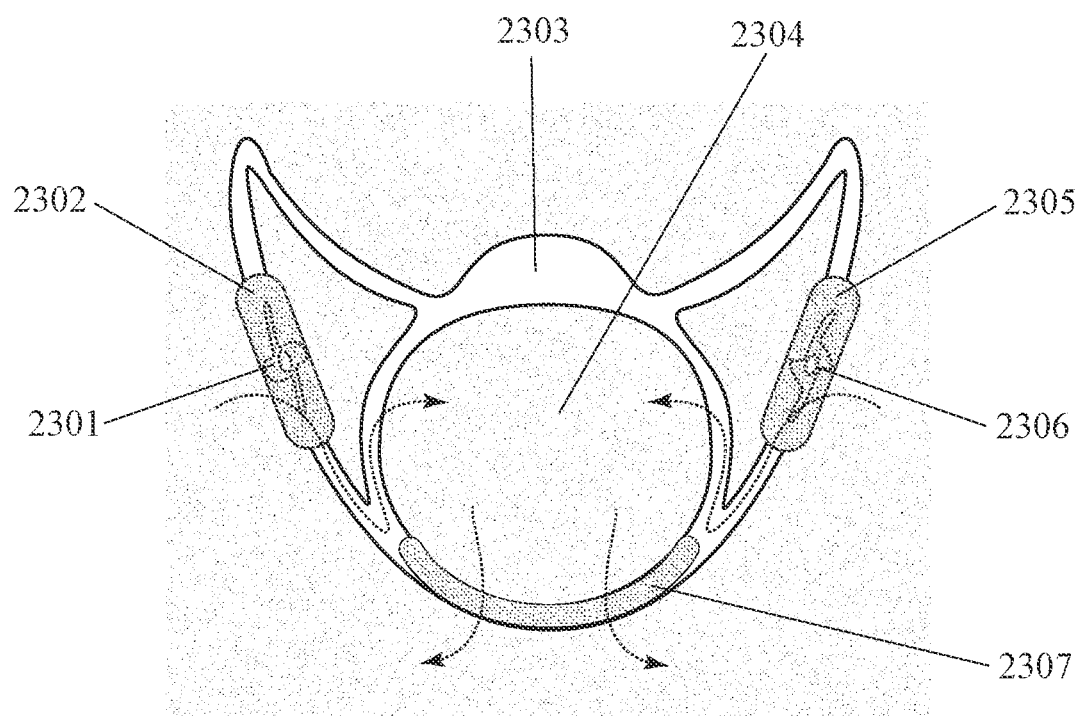
FIG. 23 shows a face mask with a transparent portion, a non-transparent portion, first-side and second-side air filters and impellors which are close to a person's ears, and a lower air filter below the person's mouth.

FIG. 23 shows an example of a pathogen-filtering semi-transparent face mask comprising: a transparent portion 2304 of a face mask which covers at least part of a person's mouth; a non-transparent portion 2303 of the mask which holds the transparent portion on the person's head; a first-side air filter 2302 on a first side (e.g. the right side) of the mask, wherein the portion of the perimeter of the first-side air filter which is closest to the person's first side ear is within 2" of the first side ear; a first-side air impellor 2301 which moves air through the first-side air filter; a second-side air filter 2305 on a second side (e.g. the left side) of the mask, wherein the portion of the perimeter of the second-side air filter which is closest to the person's second side ear is within 2" of the second side ear; a second-side air impellor 2306 which moves air through the second-side air filter; and a lower air filter 2307 below the person's mouth.

In an example, a transparent portion of a face mask can have a circular, elliptical, oval, or egg-shaped perimeter. In an example, a transparent portion of a face mask can have a polygonal (e.g. hexagonal or octagonal) perimeter. In an example, a transparent portion of a face mask can be concave, wherein the concavity opens toward a person's mouth. In an example, a transparent portion can have a hemispherical shape. In an example, a transparent portion can have a shape which is a section of a sphere, ellipsoid, or oblate spheroid. In an example, a transparent portion can have a saddle shape or a bicycle seat shape. In an example, a transparent portion can have a cardioid shape. In an example, a transparent portion can have a kidney shape.

In an example, a non-transparent portion of a mask can include (or comprise) straps or bands which loop around a person's ears to hold a transparent portion of the mask on the person's head. In an example, a non-transparent portion of a mask can include (or comprise) straps or bands which loop around the back of a person's head to hold a transparent portion of the mask on the person's head. In an example, first-side and second-side air filters can be located on such straps or bands. In an example, air can flow through straps or bands between air filters and a transparent portion of a mask.

In an example, the portion of the perimeter of a (first or second) side air filter which is closest to the person's (first or second) side ear can be within 1" of the (first or second) side ear. In an example, an air filter can have a circular shape. In an example, an air filter can have an arcuate shape. In an example, an air filter can be removably attached to a face mask via a clip, snap, clasp, hook, clamp, adhesive substance, or pin. In an example, an air filter can be disposable. In an example, an air filter can be detached from a face mask, cleaned, and then reattached to the face mask. In an example, an air filter can be located along the perimeter of a transparent portion of a face mask. In an example, a side air filter can be located between a person's mouth and an ear. In an example, a lower air filter can be located in the lower half of the transparent portion of a face mask. In an example, a lower air filter can be located on a person's jaw and/or chin. In an example, an air filter can be located below a person's jaw and/or chin.

In an example, when the first-side air impellor and/or second-side air impellor are in operation then: airflow through the first-side air filter and/or second-side air filter can be primarily (or entirely) from the environment into the interior of the mask; and airflow through the lower air filter can be primarily (or entirely) from the interior of the mask out into environment. In an example, when the first-side air impellor and second-side air impellor are not in operation then: airflow through the first-side air filter, the second-side air filter, and/or the lower air filter can be primarily (or entirely) from the environment into the interior of the mask when the person inhales and primarily (or entirely) from the interior of the mask out into environment when the person exhales. Other design variations discussed elsewhere in this disclosure or in priority-linked disclosures can also be applied to this example where relevant.

Figure 24:
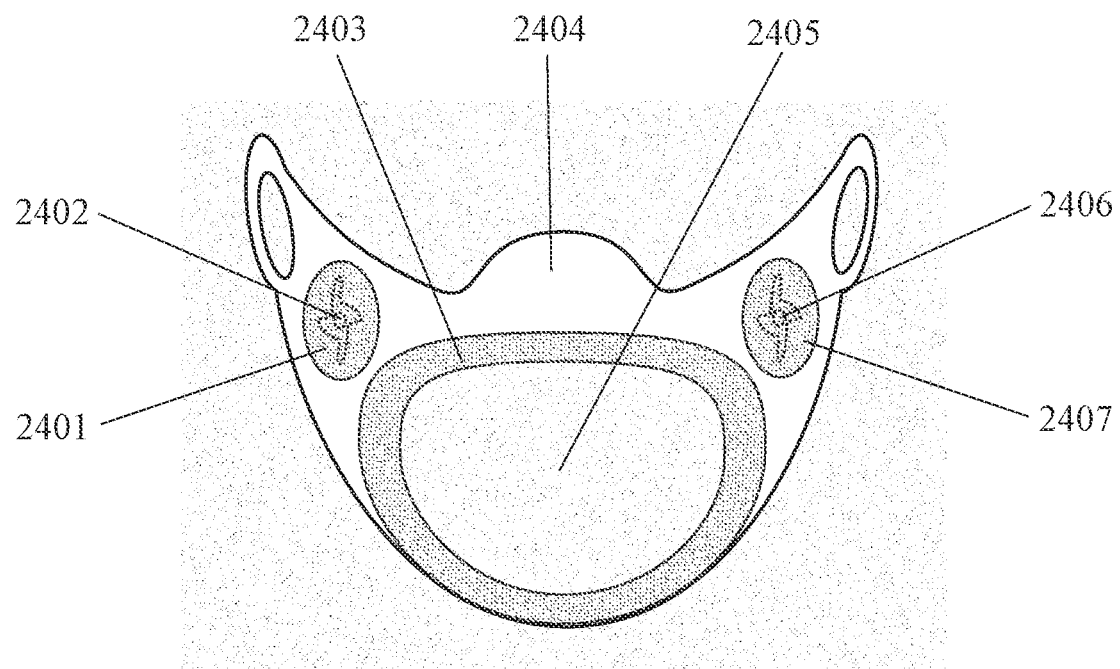
FIG. 24 shows a face mask with a transparent portion, a non-transparent portion, first-side and second-side air filters and impellors, and a perimeter air filter around the transparent portion.

FIG. 24 shows an example of a pathogen-filtering semi-transparent face mask comprising: a transparent portion 2405 of a face mask which covers at least part of a person's mouth; a non-transparent portion 2404 of the mask which holds the transparent portion on the person's head; a first-side air filter 2401 on a first side (e.g. the right side) of the mask; a first-side air impellor 2402 which moves air through the first-side air filter; a second-side air filter 2407 on a second side (e.g. the left side) of the mask; a second-side air impellor 2406 which moves air through the second-side air filter; and a perimeter air filter 2403 which spans at least 80% of the perimeter of the transparent portion.

In an example, a transparent portion of a face mask can have a circular, elliptical, oval, or egg-shaped perimeter. In an example, a transparent portion of a face mask can have a polygonal (e.g. hexagonal or octagonal) perimeter. In an example, a transparent portion of a face mask can be concave, wherein the concavity opens toward a person's mouth. In an example, a transparent portion can have a hemispherical shape. In an example, a transparent portion can have a shape which is a section of a sphere, ellipsoid, or oblate spheroid. In an example, a transparent portion can have a saddle shape or a bicycle seat shape. In an example, a transparent portion can have a cardioid shape. In an example, a transparent portion can have a kidney shape.

In an example, a perimeter air filter can span at least 80% of the perimeter of the transparent portion of a face mask. In an example, a perimeter air filter can curve around at least 80% of the perimeter of the transparent portion of a face mask. In an example, a perimeter air filter can follow at least 80% of the perimeter of the transparent portion of a face mask. In an example, a perimeter air filter can encircle at least 80% of the perimeter of the transparent portion of a face mask. In an example, a perimeter air filter can span the entire perimeter of the transparent portion of a face mask. In an example, a perimeter air filter can be between the transparent portion and the transparent portion of a face mask.

In an example, when the first-side air impellor and/or second-side air impellor are in operation then: airflow through the first-side air filter and/or second-side air filter can be primarily (or entirely) from the environment into the interior of the mask; and airflow through the perimeter air filter can be primarily (or entirely) from the interior of the mask out into environment. In an example, when the first-side air impellor and second-side air impellor are not in operation then: airflow through the first-side air filter, the second-side air filter, and/or the perimeter air filter can be primarily (or entirely) from the environment into the interior of the mask when the person inhales and primarily (or entirely) from the interior of the mask out into environment when the person exhales. Other design variations discussed elsewhere in this disclosure or in priority-linked disclosures can also be applied to this example where relevant.

Figure 25:
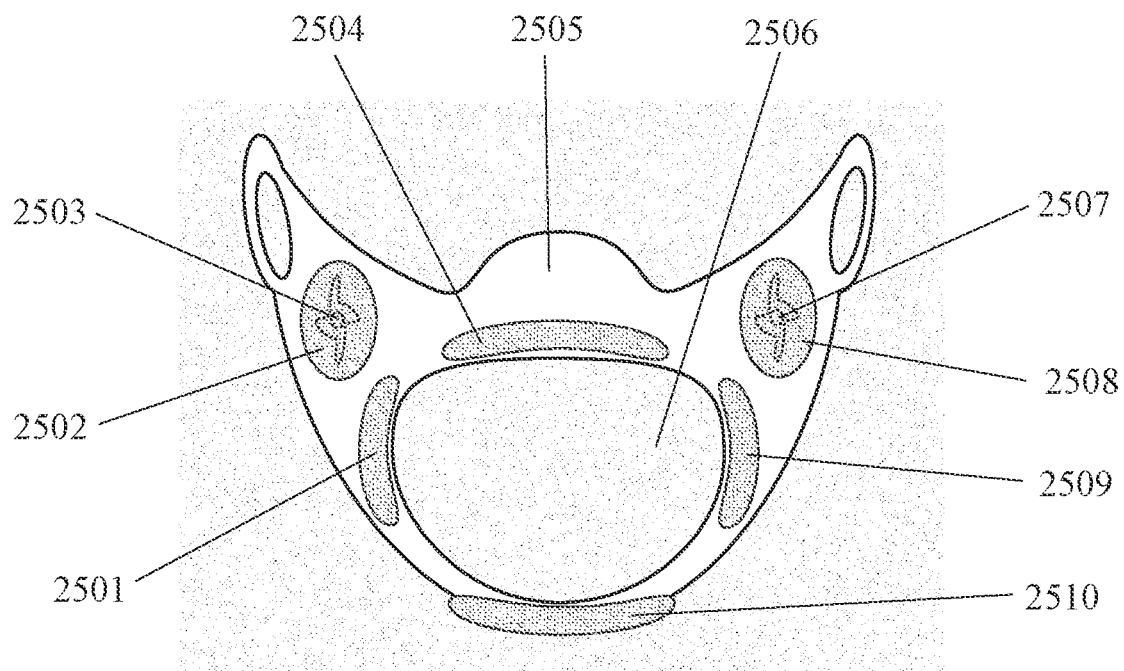
FIG. 25 shows a face mask with a transparent portion, a non-transparent portion, first-side and second-side air filters and impellors, and four air filters around the transparent portion.

FIG. 25 shows an example of a pathogen-filtering semi-transparent face mask comprising: a transparent portion 2506 of a face mask which covers at least part of a person's mouth; a non-transparent portion 2505 of the mask which holds the transparent portion on the person's head; a first-side air filter 2502 on a first side (e.g. the right side) of the mask, wherein the portion of the perimeter of the first-side air filter which is closest to the person's first side ear is within 2" of the first side ear; a first-side air impellor 2503 which moves air through the first-side air filter; a second-side air filter 2508 on a second side (e.g. the left side) of the mask, wherein the portion of the perimeter of the second-side air filter which is closest to the person's second side ear is within 2" of the second side ear; a second-side air impellor 2507 which moves air through the second-side air filter; and an perimeter array of air filters (2501, 2504, 2509, and 2510) around the perimeter of the transparent portion.

In an example, a perimeter array of air filters can comprise four air filters around the perimeter of a transparent portion of the mask. In an example, a perimeter array of air filters can comprise six or more air filters around the perimeter of a transparent portion of the mask. In an example, a perimeter array of air filters can be an arcuate array of air filters. In an example, a perimeter array of air filters can be a circular, elliptical, or oval array of air filters. In an example, a perimeter array of air filters can be a polygonal array of air filters. In an example, a perimeter array of air filters can be a quadrilateral, hexagonal, or octagonal array of air filters. In an example, a perimeter array of air filters can span at least 75% of the perimeter of a transparent portion of the mask.

In an example, when the first-side air impellor and/or second-side air impellor are in operation then: airflow through the first-side air filter and/or second-side air filter can be primarily (or entirely) from the environment into the interior of the mask; and airflow through the perimeter array of air filters can be primarily (or entirely) from the interior of the mask out into environment. In an example, when the first-side air impellor and second-side air impellor are not in operation then: airflow through the first-side air filter, the second-side air filter, and/or the perimeter array of air filters can be primarily (or entirely) from the environment into the interior of the mask when the person inhales and primarily (or entirely) from the interior of the mask out into environment when the person exhales. Other design variations discussed elsewhere in this disclosure or in priority-linked disclosures can also be applied to this example where relevant.

Figure 26:
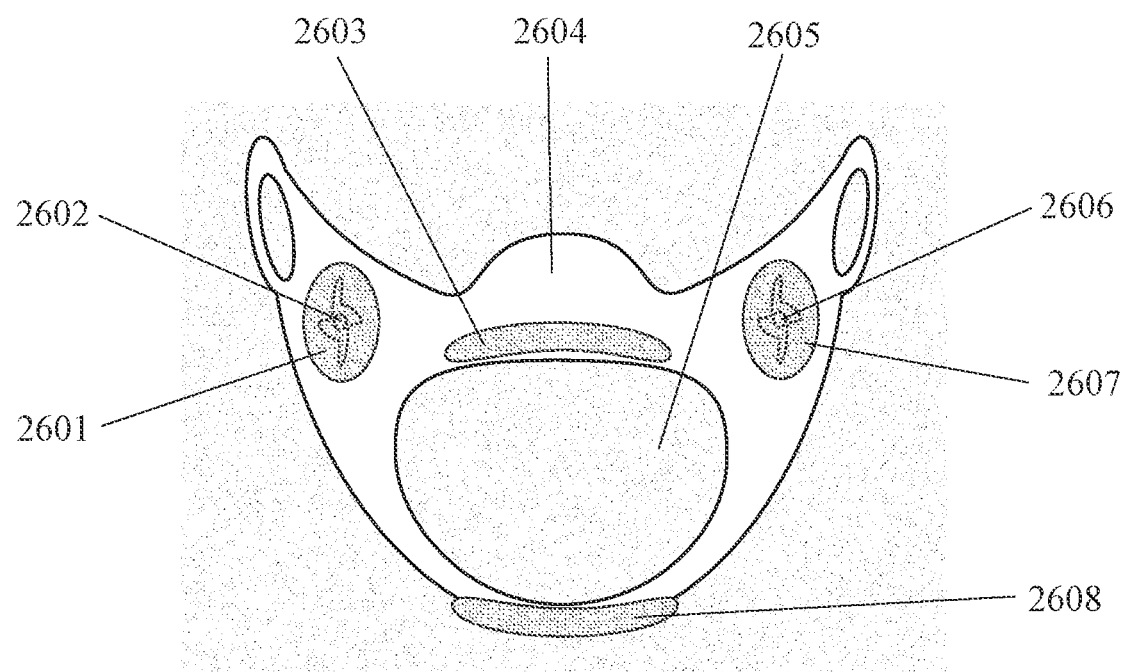
FIG. 26 shows a face mask with a transparent portion, a non-transparent portion, first-side and second-side air filters and impellors, and upper and lower air filters around the transparent portion.

FIG. 26 shows an example of a pathogen-filtering semi-transparent face mask comprising: a transparent portion 2605 of a face mask which covers at least part of a person's mouth; a non-transparent portion 2604 of the mask which holds the transparent portion on the person's head; a first-side air filter 2601 on a first side (e.g. the right side) of the mask, wherein the portion of the perimeter of the first-side air filter which is closest to the person's first side ear is within 2" of the first side ear; a first-side air impellor 2602 which moves air through the first-side air filter; a second-side air filter 2607 on a second side (e.g. the left side) of the mask, wherein the portion of the perimeter of the second-side air filter which is closest to the person's second side ear is within 2" of the second side ear; a second-side air impellor 2606 which moves air through the second-side air filter; an upper-perimeter air filter 2603 on the upper perimeter of the transparent portion above the person's mouth; and a lower-perimeter air filter 2608 on the lower perimeter of the transparent portion below the person's mouth.

In an example, an upper-perimeter air filter can be above a person's mouth and below the person's nose. In an example, an upper-perimeter air filter can be over a person's nose nostrils. In an example, an upper-perimeter air filter can span between 20% and 50% of the perimeter of a transparent portion of the mask. In an example, a lower-perimeter air filter can be below a person's mouth and above their chin. In an example, an upper-perimeter air filter can be on a person's jaw or chin. In an example, a lower-perimeter air filter can span between 20% and 50% of the perimeter of a transparent portion of the mask.

In an example, when the first-side air impellor and/or second-side air impellor are in operation then: airflow through the first-side air filter and/or second-side air filter can be primarily (or entirely) from the environment into the interior of the mask; and airflow through the (upper and lower) perimeter air filters can be primarily (or entirely) from the interior of the mask out into environment. In an example, when the first-side air impellor and second-side air impellor are not in operation then: airflow through the first-side air filter, the second-side air filter, and/or the (upper and lower) perimeter air filters can be primarily (or entirely) from the environment into the interior of the mask when the person inhales and primarily (or entirely) from the interior of the mask out into environment when the person exhales. Other design variations discussed elsewhere in this disclosure or in priority-linked disclosures can also be applied to this example where relevant.

Figure 27:
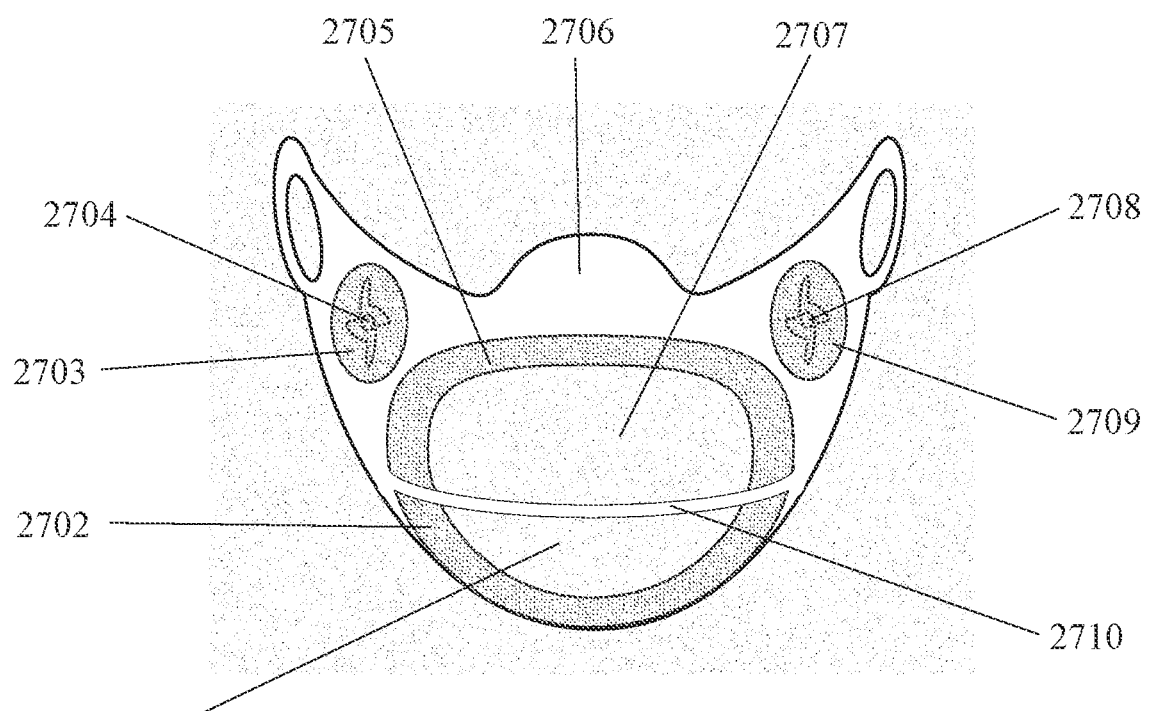
FIG. 27 shows a face mask with a transparent portion which is divided by a flexible section, a non-transparent portion, first-side and second-side air filters and impellors, and upper and lower air filters around the transparent portion.

FIG. 27 shows an example of a pathogen-filtering semi-transparent face mask comprising: an transparent portion of a face mask which covers at least part of a person's mouth, wherein the transparent portion further comprises an upper transparent section 2707 and a lower transparent section 2701; a flexible section 2710 between the upper transparent section and the lower transparent section; a perimeter air filter around at least 80% of the perimeter of the transparent portion, wherein the perimeter air filter further comprises an upper filter section 2705 and a lower filter section 2702; a non-transparent portion 2706 of the mask which holds the transparent portion on the person's head; a first-side air filter 2703 on a first side (e.g. the right side) of the mask; a first-side air impellor 2704 which moves air through the first-side air filter; a second-side air filter 2709 on a second side (e.g. the left side) of the mask; and a second-side air impellor 2708 which moves air through the second-side air filter.

In an example, a flexible section between an upper transparent section and a lower transparent section can enable the upper transparent section and the lower transparent section to move relative to each other. This can enable a person to move their jaw and mouth more than if the transparent portion were a single contiguous inflexible structure. In an example, the flexible section between an upper transparent section and a lower transparent section can be a longitudinal flexible strip or band which spans the transparent section from a first side (e.g. the right side) to a second side (e.g. the left side). In an example, the flexible section can have a width in the range of ¼" to ¾". In an example, the flexible section can be stretchable and/or elastic. In an example, the flexible section can also be between an upper filter section and a lower filter section.

In an example, when the first-side air impellor and/or second-side air impellor are in operation then: airflow through the first-side air filter and/or second-side air filter can be primarily (or entirely) from the environment into the interior of the mask; and airflow through the perimeter air filter can be primarily (or entirely) from the interior of the mask out into environment. In an example, when the first-side air impellor and second-side air impellor are not in operation then: airflow through the first-side air filter, the second-side air filter, and/or the perimeter air filter can be primarily (or entirely) from the environment into the interior of the mask when the person inhales and primarily (or entirely) from the interior of the mask out into environment when the person exhales. Other design variations discussed elsewhere in this disclosure or in priority-linked disclosures can also be applied to this example where relevant.

Figure 28:
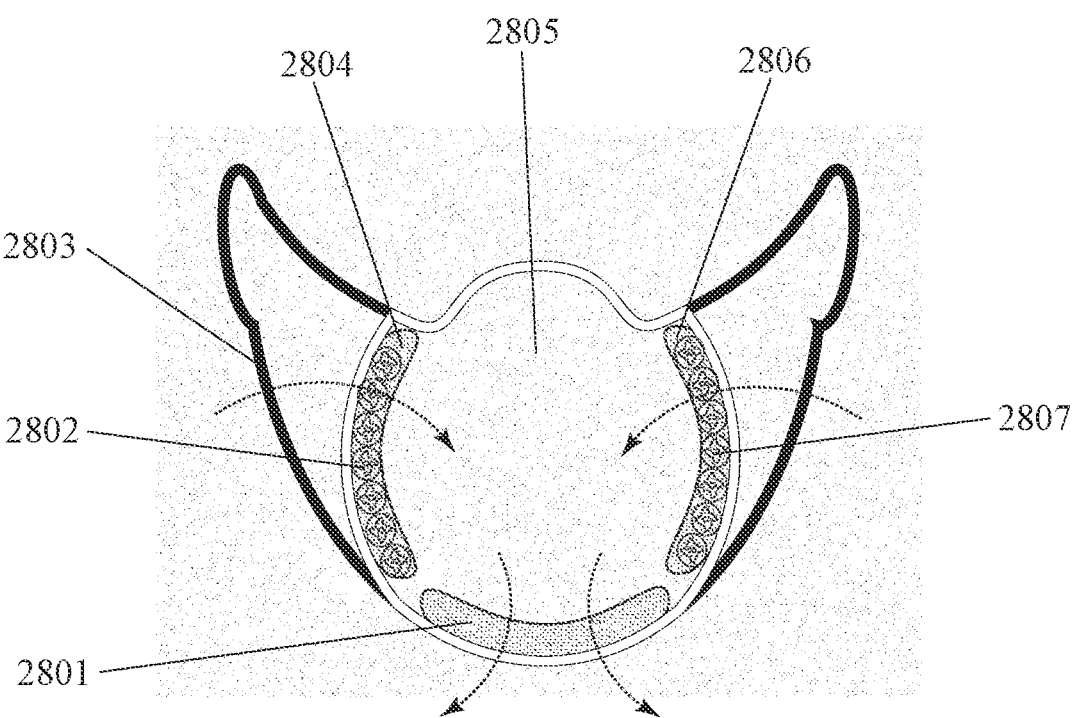
FIG. 28 shows a face mask with a transparent portion, straps, right-side and left-side air filters and air impellor arrays, and a lower air filter.

FIG. 28 shows an example of a pathogen-filtering semi-transparent face mask comprising: a transparent portion 2805 of a face mask which covers at least part of a person's mouth; straps, bands, or cords (including 2803) which hold the transparent portion on the person's head; a first-side air filter 2804 on a first side (e.g. the right side) of the mask; a first plurality of air impellors (including 2802) which move air through the first-side air filter; a second-side air filter 2806 on a second side (e.g. the left side) of the mask; a second plurality of air impellors (including 2807) which move air through the second-side air filter; and a lower air filter 2801 on or below the lower perimeter of the transparent portion.

There can be advantages from using a plurality of smaller air impellors instead of a single larger air impellor. One advantage is greater design flexibility with respect to the shape of an air exchange component on a mask. For example, a single large rotating impellor tends to require an air exchange component with a central circular cross-sectional shape. However, using a plurality of smaller air impellors instead of using one larger impellor can provide more design flexibility in the shape of an air exchange component on a mask. For example, one can create a linear or longitudinally-arcuate air exchange component by using a linear or longitudinally-arcuate array of air impellors. In an example, an arcuate array of air impellors can span some (or all) of an arcuate perimeter of a transparent portion of a mask. In an example, a circular array of air impellors can span a circular perimeter of a transparent portion of a mask. In an example, a linear array of air impellors can span some (or all) of a polygonal perimeter of a transparent portion of a mask.

The can also be other advantages from using a plurality of smaller air impellors instead of a single larger air impellor. In an example, a plurality of smaller air impellors can make less noise when rotating than a single larger air impellor. In an example, a plurality of smaller air impellors can move the same amount of air with a lower electric power requirement than a single larger air impellor. In an example, a plurality of smaller air impellors can produce more-uniform airflow than a single larger air impellor. In an example, a plurality of smaller air impellors can be safer than a single larger air impellor. In an example, a plurality of smaller air impellors can be substituted for a single larger air impellor in any of the other examples disclosed herein in order to achieve one of more of the above advantages.

In an example, the amount of airflow through an air filter can be adjusted by selectively changing the number of air impellors in a plurality of air impellors which are activated. In an example, the amount or direction of airflow through an air filter can be adjusted by selectively changing which air impellors in a plurality of air impellors which are activated. In an example, different air impellors in a plurality of air impellors can be activated in response to data from sensors which indicate how dirty and/or clogged different portions of an air filter are. In an example, different air impellors in a plurality of air impellors can be activated in response to data from biometric and/or physiological sensors which monitor the person. In an example, different air impellors in a plurality of air impellors can be activated in response to data from sensors which monitor air quality inside the mask (e.g. inside the transparent portion of the mask). In an example, different air impellors in a plurality of air impellors can be activated in response to data from environmental sensors.

In an example, when first-side and/or second-side air impellor arrays are in operation then: airflow through first-side and/or second-side air filters can be primarily (or entirely) from the environment into the interior of the mask; and airflow through the lower air filter can be primarily (or entirely) from the interior of the mask out into environment. In an example, when the first-side and second-side air impellor arrays are not in operation then: airflow through any of the air filters can be primarily (or entirely) from the environment into the interior of the mask when the person inhales and primarily (or entirely) from the interior of the mask out into environment when the person exhales. Other design variations discussed elsewhere in this disclosure or in priority-linked disclosures can also be applied to this example where relevant.

Figure 29:
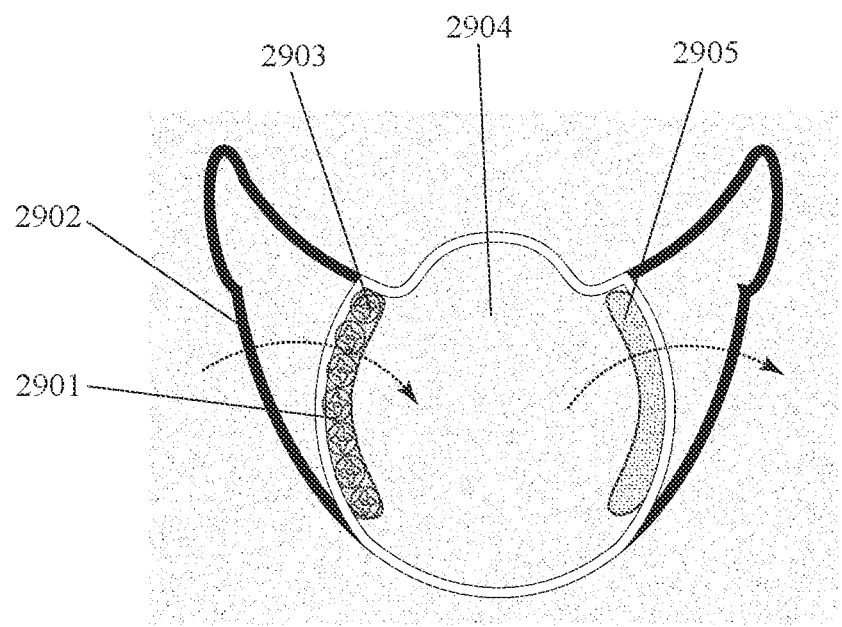
FIG. 29 shows a face mask with a transparent portion, straps, a first-side air filter and air impellor array, and a second-side air filter.

FIG. 29 shows an example of a pathogen-filtering semi-transparent face mask comprising: a transparent portion 2904 of a face mask which covers at least part of a person's mouth; straps, bands, or cords (including 2902) which hold the transparent portion on the person's head; a first-side air filter 2903 on a first side (e.g. the right side) of the mask; a plurality of air impellors (including 2901) which move air through the first-side air filter; and a second-side air filter 2905 on a second side (e.g. the left side) of the mask.

There can be advantages from using a plurality of smaller air impellors instead of a single larger air impellor. One advantage is greater design flexibility with respect to the shape of an air exchange component on a mask. For example, a single large rotating impellor tends to require an air exchange component with a central circular cross-sectional shape. However, using a plurality of smaller air impellors instead of using one larger impellor can provide more design flexibility in the shape of an air exchange component on a mask. For example, one can create a linear or longitudinally-arcuate air exchange component by using a linear or longitudinally-arcuate array of air impellors. In an example, an arcuate array of air impellors can span some (or all) of an arcuate perimeter of a transparent portion of a mask. In an example, a circular array of air impellors can span a circular perimeter of a transparent portion of a mask. In an example, a linear array of air impellors can span some (or all) of a polygonal perimeter of a transparent portion of a mask.

The can also be other advantages from using a plurality of smaller air impellors instead of a single larger air impellor. In an example, a plurality of smaller air impellors can make less noise when rotating than a single larger air impellor. In an example, a plurality of smaller air impellors can move the same amount of air with a lower electric power requirement than a single larger air impellor. In an example, a plurality of smaller air impellors can produce more-uniform airflow than a single larger air impellor. In an example, a plurality of smaller air impellors can be safer than a single larger air impellor. In an example, a plurality of smaller air impellors can be substituted for a single larger air impellor in any of the other examples disclosed herein in order to achieve one of more of the above advantages.

In an example, the amount of airflow through an air filter can be adjusted by selectively changing the number of air impellors in a plurality of air impellors which are activated. In an example, the amount or direction of airflow through an air filter can be adjusted by selectively changing which air impellors in a plurality of air impellors which are activated. In an example, different air impellors in a plurality of air impellors can be activated in response to data from sensors which indicate how dirty and/or clogged different portions of an air filter are. In an example, different air impellors in a plurality of air impellors can be activated in response to data from biometric and/or physiological sensors which monitor the person. In an example, different air impellors in a plurality of air impellors can be activated in response to data from sensors which monitor air quality inside the mask (e.g. inside the transparent portion of the mask). In an example, different air impellors in a plurality of air impellors can be activated in response to data from environmental sensors.

In an example, when first-side air impellors are in operation then: airflow through the first-side air filter can be primarily (or entirely) from the environment into the interior of the mask; and airflow through the second-side air filter can be primarily (or entirely) from the interior of the mask out into environment. In an example, when the first-side air impellors are not in operation then airflow through either of the air filters can be primarily (or entirely) from the environment into the interior of the mask when the person inhales and primarily (or entirely) from the interior of the mask out into environment when the person exhales. Other design variations discussed elsewhere in this disclosure or in priority-linked disclosures can also be applied to this example where relevant.

Figure 30:
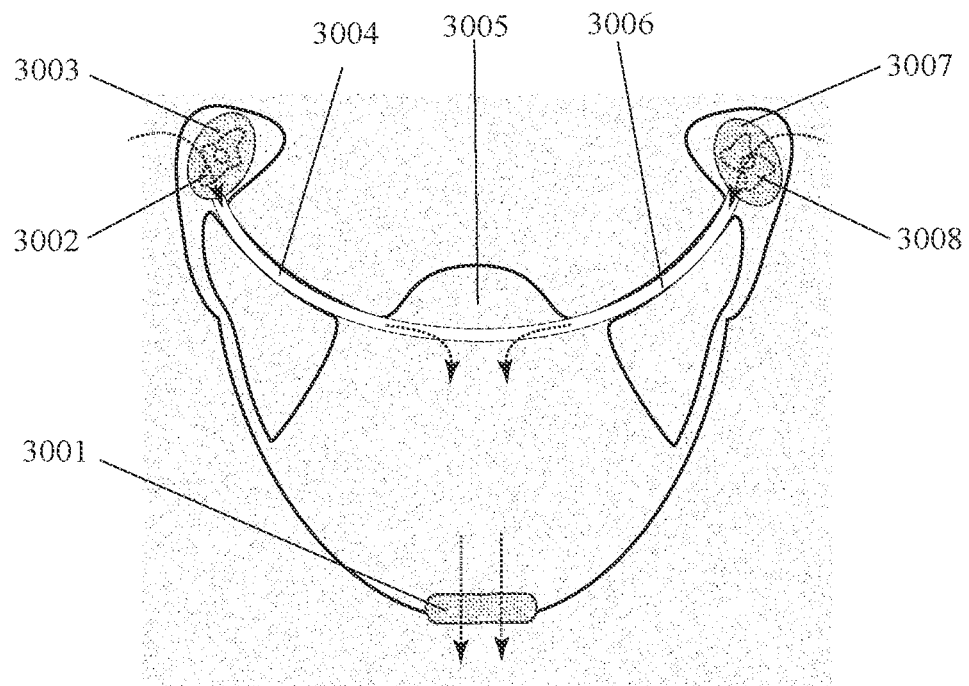
FIG. 30 shows a face mask with a transparent portion, right-side and left-side air filters and air impellors behind a person's ears, and a lower air filter on a person's chin, and air tubes or channels.

FIG. 30 shows an example of a pathogen-filtering semi-transparent face mask comprising: a transparent portion 3005 of a face mask which covers at least part of a person's mouth; a first-side air filter 3003 on a first side (e.g. the right side) of the person's head, wherein the first-side air filter is behind (e.g. posterior to) the person's first-side ear; a first-side air impellor 3002 which moves air through the first-side air filter; a first-side air tube (or channel) 3004 which directs airflow between the first-side air filter and the transparent portion; a second-side air filter 3007 on a second side (e.g. the left side) of the person's head, wherein the second-side air filter is behind (e.g. posterior to) the person's second-side ear; a second-side air impellor 3008 which moves air through the second-side air filter; a second-side air tube (or channel) 3006 which directs airflow between the second-side air filter and the transparent portion; and a lower air filter 3001 below the person's mouth.

In an example, a (first or second) side air filter can be located behind a person's ear. In an example, a (first or second) side air filter can be located directly behind a person's ear. In an example, a (first or second) side air filter can be behind a person's ear and also within 2" of the ear. In an example, a (first or second) side air filter can be behind a person's ear and also between 1" and 3" from the ear. In an example, a mask can further comprise straps, bands, or cords which hold a transparent portion of the mask on a person's head. In an example, an air tube (or channel) can be inside a strap, band, or cord in order to direct airflow from an air filter behind a person's ear to the transparent portion of a mask. In an example, a strap, band, or cord which holds a mask on a person's head can also be an air tube (or channel). In an example, a mask can further comprise straps, bands, or cords which: connect a transparent portion of a mask to a person's ears; and also conduct airflow between one or more air filters behind (e.g. posterior to) the person's ears to the interior of the transparent portion of the mask.

In an example, an air tube (e.g. air tube, channel, or pathway) can channel airflow between one or more air filters and an interior space of a transparent portion of a mask. This can be especially useful when an air filter and/or an air impellor are located relatively far away from the transparent portion of the mask for esthetic and/or other design reasons. In an example, a first air tube can channel airflow between a first air filter and an interior space of a transparent portion of a mask and a second air tube can channel airflow between a second air filter and the interior space of the transparent portion of the mask. In an example, an air tube (e.g. air tube, channel, or pathway) can span a portion of the perimeter of a transparent portion of a mask. In an example, an arcuate air tube can curve around a portion of an arcuate perimeter of a transparent portion of a mask.

In an example, an air tube in a mask can have an air-impermeable section and an air-permeable (e.g. perforated) section. In an example, the air-permeable section can have holes, openings, and perforations which allow fluid communication (e.g. air flow) with the interior space of the mask. In an example, the air-impermeable section can be closer to an air filter or air impellor and the air-permeable section can be closer to the interior space of a mask. In an example, the air-permeable section can have holes, openings, and perforations which allow fluid communication (e.g. air flow) with the interior space of transparent portion of the mask. In an example, the air-impermeable section can be closer to an air filter or air impellor and the air-permeable section can be closer to the interior space of the transparent portion of a mask.

In an example, the inner diameter of an air tube (e.g. air tube, channel, or pathway) can be within the range of ⅛" to ½". In an example, the length of an air tube can be within the range of ½" to 5". In an example, between 25% and 75% of the length of an air tube can be perforated with holes. In an example, between 50% and 80% of the length of an air tube can be perforated with holes. In an example, the interior of an air tube can have a circular cross-sectional shape. In an example, the interior of an air tube can have an elliptical, oval, and/or oblong cross-sectional shape. In an example, an air tube can be detached from a mask for cleaning and then reattached.

In an example, when the first-side air impellor and/or second-side air impellor are in operation then: airflow through the first-side air filter and/or second-side air filter can be primarily (or entirely) from the environment into the interior of the mask; and airflow through the lower air filter can be primarily (or entirely) from the interior of the mask out into environment. In an example, when the first-side air impellor and second-side air impellor are not in operation then airflow through the first-side air filter, the second-side air filter, and/or the lower air filter can be primarily (or entirely) from the environment into the interior of the mask when the person inhales and primarily (or entirely) from the interior of the mask out into environment when the person exhales. Other design variations discussed elsewhere in this disclosure or in priority-linked disclosures can also be applied to this example where relevant.

Figure 31:
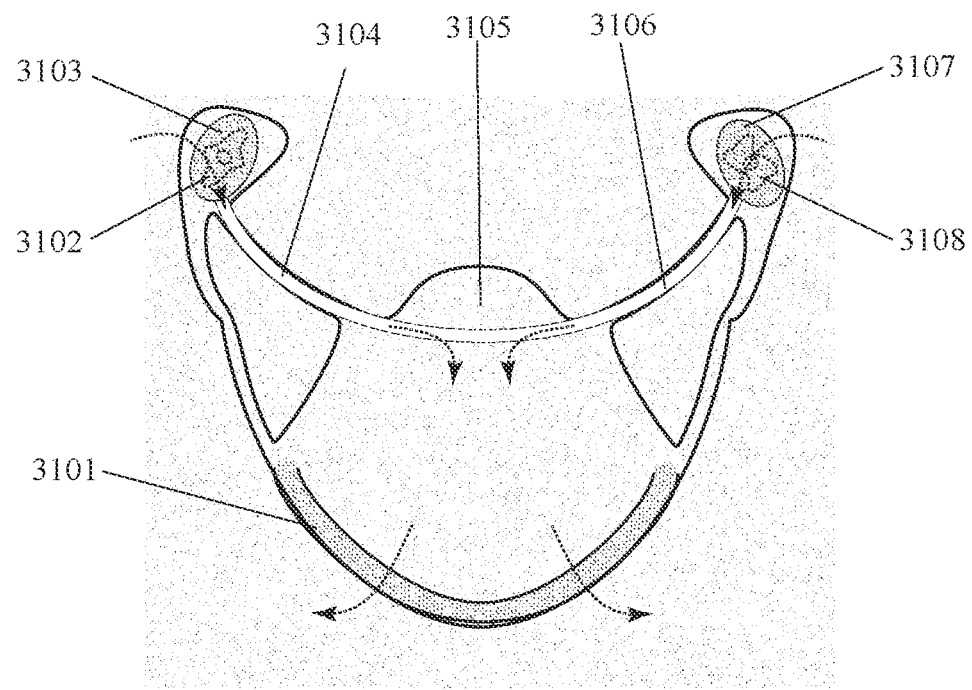
FIG. 31 shows a face mask with a transparent portion, right-side and left-side air filters and air impellors behind a person's ears, and a lower air filter along the lower perimeter of the mask.

FIG. 31 shows an example of a face mask which is similar to the one shown in FIG. 30 except that the lower air filter spans at least 25% of the lower perimeter of the mask. FIG. 31 shows an example of a pathogen-filtering semi-transparent face mask comprising: a transparent portion 3105 of a face mask which covers at least part of a person's mouth; a first-side air filter 3103 on a first side (e.g. the right side) of the person's head, wherein the first-side air filter is behind (e.g. posterior to) the person's first-side ear; a first-side air impellor 3102 which moves air through the first-side air filter; a first-side air tube (or channel) 3104 which directs airflow between the first-side air filter and the transparent portion; a second-side air filter 3107 on a second side (e.g. the left side) of the person's head, wherein the second-side air filter is behind (e.g. posterior to) the person's second-side ear; a second-side air impellor 3108 which moves air through the second-side air filter; a second-side air tube (or channel) 3106 which directs airflow between the second-side air filter and the transparent portion; and a lower air filter 3101 which spans at least 25% of the lower perimeter of the mask.

In an example, a lower filter can span at least 25% of the lower perimeter of a mask. In an example, a lower filter can span at least 50% of the lower perimeter of a mask. In an example, a lower filter can span between 20% and 80% of the lower perimeter of a mask. In an example, a lower filter can span the entire lower perimeter of a mask. In an example, a lower filter can span at least 25% of the lower perimeter (e.g. from one ear to another) of a mask. In an example, a lower filter can span at least 50% of the lower perimeter (e.g. from one ear to another) of a mask. In an example, a lower filter can span between 20% and 80% of the lower perimeter (e.g. from one ear to another) of a mask. In an example, a lower filter can span the entire e lower perimeter (e.g. from one ear to another) of a mask. In an example, a lower filter can span at least 25% of the lower perimeter of a transparent portion. In an example, a lower filter can span at least 50% of the lower perimeter of a transparent portion. In an example, a lower filter can span between 20% and 80% of the lower perimeter of a transparent portion. In an example, a lower filter can span the entire lower perimeter of a transparent portion.

In an example, when the first-side air impellor and/or second-side air impellor are in operation then: airflow through the first-side air filter and/or second-side air filter can be primarily (or entirely) from the environment into the interior of the mask; and airflow through the lower air filter can be primarily (or entirely) from the interior of the mask out into environment. In an example, when the first-side air impellor and second-side air impellor are not in operation then airflow through the first-side air filter, the second-side air filter, and/or the lower air filter can be primarily (or entirely) from the environment into the interior of the mask when the person inhales and primarily (or entirely) from the interior of the mask out into environment when the person exhales. Other design variations discussed elsewhere in this disclosure or in priority-linked disclosures can also be applied to this example where relevant.

Figure 32:
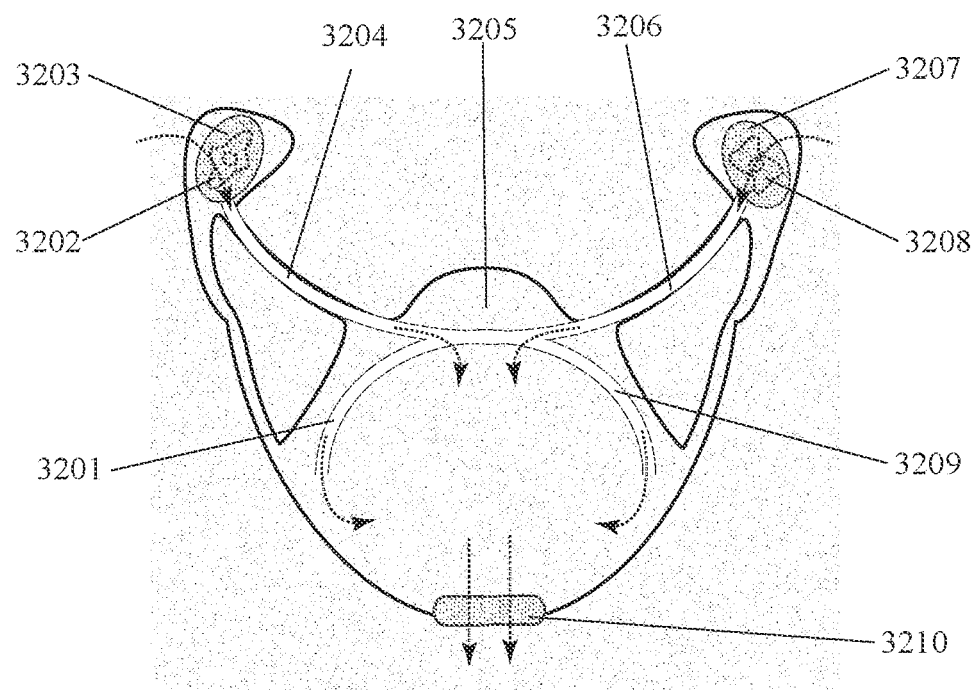
FIG. 32 shows a face mask with a transparent portion, right-side and left-side air filters and air impellors behind a person's ears, a lower air filter on a person's chin, and air tubes or channels on either side of the person's mouth.

FIG. 32 shows an example of a pathogen-filtering semi-transparent face mask comprising: a transparent portion 3205 of a face mask which covers at least part of a person's mouth; a first-side air filter 3203 on a first side (e.g. the right side) of the person's head, wherein the first-side air filter is behind (e.g. posterior to) the person's first-side ear; a first-side air impellor 3202 which moves air through the first-side air filter; a first air tube (or channel) 3204 which is in fluid communication the first-side air filter; a second air tube (or channel) 3201 which is in fluid communication with the first air tube and at least partially encircles the person's mouth; a second-side air filter 3207 on a second side (e.g. the left side) of the person's head, wherein the second-side air filter is behind (e.g. posterior to) the person's second-side ear; a second-side air impellor 3208 which moves air through the second-side air filter; a third air tube (or channel) 3206 which is in fluid communication the second-side air filter; a fourth air tube (or channel) 3209 which is in fluid communication with the third air tube and at least partially encircles the person's mouth; and a lower air filter 3210 below the person's mouth.

In an example, a (first or second) side air filter can be located behind a person's ear. In an example, a (first or second) side air filter can be located directly behind a person's ear. In an example, a (first or second) side air filter can be behind a person's ear and also within 2" of the ear. In an example, a (first or second) side air filter can be behind a person's ear and also between 1" and 3" from the ear. In an example, a mask can further comprise straps, bands, or cords which hold a transparent portion of the mask on a person's head. In an example, an air tube (or channel) can be inside a strap, band, or cord in order to direct airflow from an air filter behind a person's ear to the transparent portion of a mask. In an example, a strap, band, or cord which holds a mask on a person's head can also be an air tube (or channel). In an example, a mask can further comprise straps, bands, or cords which: connect a transparent portion of a mask to a person's ears; and also conduct airflow between one or more air filters behind (e.g. posterior to) the person's ears to the interior of the transparent portion of the mask.

In an example, an air tube (e.g. air tube, channel, or pathway) can channel airflow between one or more air filters and an interior space of a transparent portion of a mask. This can be especially useful when an air filter and/or an air impellor are located relatively far away from the transparent portion of the mask for esthetic and/or other design reasons. In an example, an air tube can channel airflow between a first air filter and an interior space of a transparent portion of a mask and an air tube can channel airflow between a second air filter and the interior space of the transparent portion of the mask. In an example, an air tube (e.g. air tube, channel, or pathway) can span a portion of the perimeter of a transparent portion of a mask. In an example, an arcuate air tube can curve around a portion of an arcuate perimeter of a transparent portion of a mask.

In an example, an air tube in a mask can have an air-impermeable section and an air-permeable (e.g. perforated) section. In an example, the air-permeable section can have holes, openings, and perforations which allow fluid communication (e.g. air flow) with the interior space of the mask. In an example, the air-impermeable section can be closer to an air filter or air impellor and the air-permeable section can be closer to the interior space of a mask. In an example, the air-permeable section can have holes, openings, and perforations which allow fluid communication (e.g. air flow) with the interior space of transparent portion of the mask. In an example, the air-impermeable section can be closer to an air filter or air impellor and the air-permeable section can be closer to the interior space of the transparent portion of a mask.

In an example, the inner diameter of an air tube (e.g. air tube, channel, or pathway) can be within the range of ⅛" to ½". In an example, the length of an air tube can be within the range of ½" to 5". In an example, between 25% and 75% of the length of an air tube can be perforated with holes. In an example, between 50% and 80% of the length of an air tube can be perforated with holes. In an example, the interior of an air tube can have a circular cross-sectional shape. In an example, the interior of an air tube can have an elliptical, oval, and/or oblong cross-sectional shape. In an example, an air tube can be detached from a mask for cleaning and then reattached.

In an example, when the first-side air impellor and/or second-side air impellor are in operation then: airflow through the first-side air filter and/or second-side air filter can be primarily (or entirely) from the environment into the interior of the mask; and airflow through the lower air filter can be primarily (or entirely) from the interior of the mask out into environment. In an example, when the first-side air impellor and second-side air impellor are not in operation then airflow through the first-side air filter, the second-side air filter, and/or the lower air filter can be primarily (or entirely) from the environment into the interior of the mask when the person inhales and primarily (or entirely) from the interior of the mask out into environment when the person exhales. Other design variations discussed elsewhere in this disclosure or in priority-linked disclosures can also be applied to this example where relevant.

Figure 33:
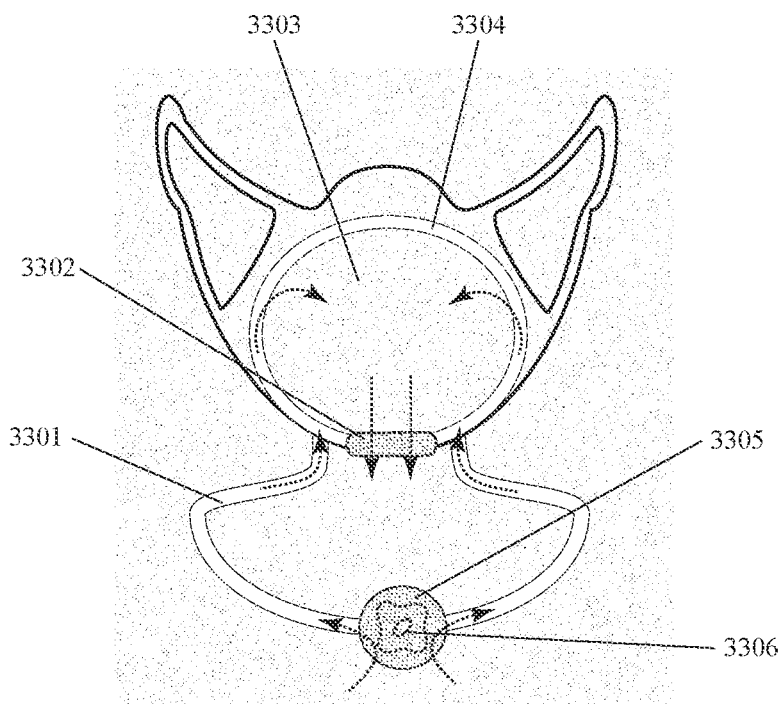
FIG. 33 shows a face mask with a transparent portion, a pendant-style air filter and air impellor on a person's torso, a lower air filter on the person's chin, and air tubes or channels.

FIG. 33 shows an example of a pathogen-filtering semi-transparent face mask comprising: a transparent portion 3303 of a face mask which covers at least part of a person's mouth; a pendant air filter 3305 which hangs from a person's neck; a pendant air impellor 3306 which moves air through the pendant air filter; a lower air tube (or channel) 3301 which is worn on the person's neck and is in fluid communication the pendant air filter; an upper air tube (or channel) 3304 which at least partially encircles the person's mouth and is in fluid communication with the lower air tube; and a jaw-worn air filter 3302 which is worn on or below the person's jaw.

In an example, a pendant air filter can hang down from a necklace around a person's neck. In an example, a pendant air tube can be part of (e.g. inside) a necklace around a person's neck. In an example, a pendant air filter can hang down from the front of a person's neck, onto the front of a person's torso. In an example, a pendant air filter can hang down from the back of a person's neck, onto the back of a person's torso. In an example, a pendant air filter can have a circular shape. In an example, a pendant air filter can have a tear-drop shape. In an example, such a mask can comprise a plurality of neck-worn air filters and/or impellors. In an example, such a mask can comprise a necklace with a plurality of neck-worn air filters and/or impellors. In an example, an air impellor can be located at the rear of a necklace (e.g. behind a person's neck or on a person's back), wherein the air impellor draws air in from a plurality of air filters along the front of the necklace. In an example, an air impellor can be located at the rear of a necklace (e.g. behind a person's neck or on a person's back). In an example, an air impellor can draw air into a mask from a plurality of openings (e.g. holes) along the front of a necklace.

In an example, an air tube (e.g. air tube, channel, or pathway) can channel airflow between one or more air filters and an interior space of a transparent portion of a mask. This can be especially useful when an air filter and/or an air impellor are located relatively far away from the transparent portion of the mask for esthetic and/or other design reasons. In an example, an air tube can channel airflow between a first air filter and an interior space of a transparent portion of a mask and an air tube can channel airflow between a second air filter and the interior space of the transparent portion of the mask. In an example, an air tube (e.g. air tube, channel, or pathway) can span a portion of the perimeter of a transparent portion of a mask. In an example, an arcuate air tube can curve around a portion of an arcuate perimeter of a transparent portion of a mask.

In an example, an air tube in a mask can have an air-impermeable section and an air-permeable (e.g. perforated) section. In an example, the air-permeable section can have holes, openings, and perforations which allow fluid communication (e.g. air flow) with the interior space of the mask. In an example, the air-impermeable section can be closer to an air filter or air impellor and the air-permeable section can be closer to the interior space of a mask. In an example, the air-permeable section can have holes, openings, and perforations which allow fluid communication (e.g. air flow) with the interior space of transparent portion of the mask. In an example, the air-impermeable section can be closer to an air filter or air impellor and the air-permeable section can be closer to the interior space of the transparent portion of a mask.

In an example, the inner diameter of an air tube (e.g. air tube, channel, or pathway) can be within the range of ⅛" to ½". In an example, the length of an air tube can be within the range of ½" to 5". In an example, between 25% and 75% of the length of an air tube can be perforated with holes. In an example, between 50% and 80% of the length of an air tube can be perforated with holes. In an example, the interior of an air tube can have a circular cross-sectional shape. In an example, the interior of an air tube can have an elliptical, oval, and/or oblong cross-sectional shape. In an example, an air tube can be detached from a mask for cleaning and then reattached.

In an example, when a pendant air impellor is in operation then: airflow through a pendant air filter can be primarily (or entirely) from the environment into the interior of the mask; and airflow through a jaw-worn air filter can be primarily (or entirely) from the interior of the mask out into environment. In an example, when the pendant air impellor is not in operation then airflow through the pendant air filter and/or the jaw-worn filter can be primarily (or entirely) from the environment into the interior of the mask when the person inhales and primarily (or entirely) from the interior of the mask out into environment when the person exhales. Other design variations discussed elsewhere in this disclosure or in priority-linked disclosures can also be applied to this example where relevant.

Figure 34:
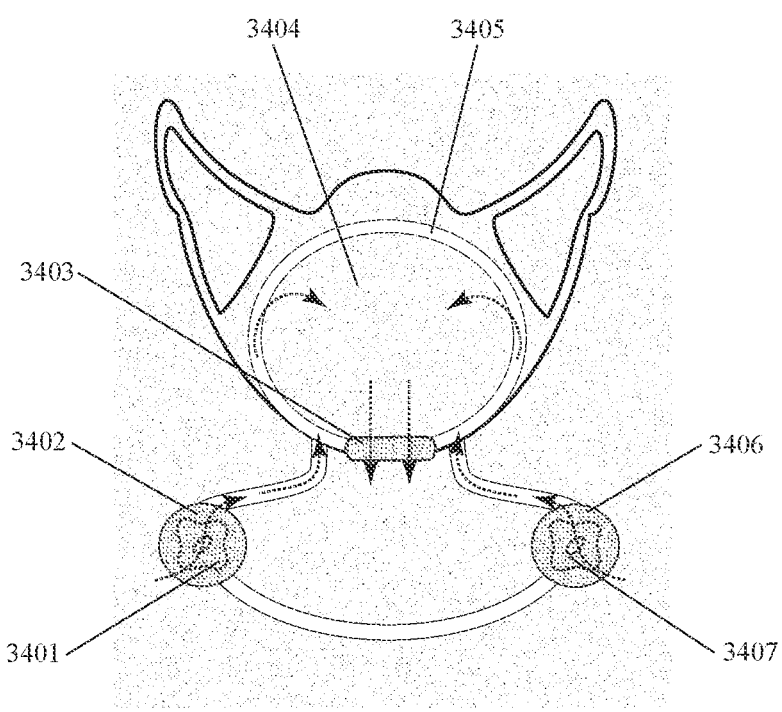
FIG. 34 shows a face mask with a transparent portion, two shoulder-worn air filters and air impellors, a lower air filter on the person's chin, and air tubes or channels.

FIG. 34 shows an example of a pathogen-filtering semi-transparent face mask comprising: a transparent portion 3404 of a face mask which covers at least part of a person's mouth; a first-side air filter 3402 which is worn on a person's first-side (e.g. right side) shoulder; a first-side air impellor 3401 which moves air through the first-side air filter; a second-side air filter 3406 which is worn on a person's second-side (e.g. left side) shoulder; a second-side air impellor 3407 which moves air through the second-side air filter; an air tube (or channel) 3405 which is in fluid communication the first-side air filter and/or the second-side air filter, wherein the air tube at least partially encircles the person's mouth; and a jaw-worn air filter 3403 which is worn on or below the person's jaw.

In an example, a (first or second) side air filter can be worn on a person's shoulder. In an example, a (first or second) side air filter can be worn on top of a person's shoulder. In an example, a (first or second) side air filter can hang down from a person's shoulder. In an example, a (first or second) side air filter can be worn on the lapel of a person's suit, jacket, or coat. In an example, a shoulder-worn air filter can have a circular shape. In an alternative example, a pathogen-filtering semi-transparent face mask can comprise only one shoulder-worn air filter (worn on only the person's right or left side) instead of two shoulder-worn air filters.

In an example, an air tube (e.g. air tube, channel, or pathway) can channel airflow between one or more air filters and an interior space of a transparent portion of a mask. This can be especially useful when an air filter and/or an air impellor are located relatively far away from the transparent portion of the mask for esthetic and/or other design reasons. In an example, an air tube can channel airflow between a first air filter and an interior space of a transparent portion of a mask and an air tube can channel airflow between a second air filter and the interior space of the transparent portion of the mask. In an example, an air tube (e.g. air tube, channel, or pathway) can span a portion of the perimeter of a transparent portion of a mask. In an example, an arcuate air tube can curve around a portion of an arcuate perimeter of a transparent portion of a mask.

In an example, an air tube in a mask can have an air-impermeable section and an air-permeable (e.g. perforated) section. In an example, the air-permeable section can have holes, openings, and perforations which allow fluid communication (e.g. air flow) with the interior space of the mask. In an example, the air-impermeable section can be closer to an air filter or air impellor and the air-permeable section can be closer to the interior space of a mask. In an example, the air-permeable section can have holes, openings, and perforations which allow fluid communication (e.g. air flow) with the interior space of transparent portion of the mask. In an example, the air-impermeable section can be closer to an air filter or air impellor and the air-permeable section can be closer to the interior space of the transparent portion of a mask.

In an example, the inner diameter of an air tube (e.g. air tube, channel, or pathway) can be within the range of ⅛" to ½". In an example, the length of an air tube can be within the range of ½" to 5". In an example, between 25% and 75% of the length of an air tube can be perforated with holes. In an example, between 50% and 80% of the length of an air tube can be perforated with holes. In an example, the interior of an air tube can have a circular cross-sectional shape. In an example, the interior of an air tube can have an elliptical, oval, and/or oblong cross-sectional shape. In an example, an air tube can be detached from a mask for cleaning and then reattached.

In an example, when one or more air impellors are in operation then: airflow through one or more shoulder air filters can be primarily (or entirely) from the environment into the interior of the mask; and airflow through a jaw-worn air filter can be primarily (or entirely) from the interior of the mask out into environment. In an example, when one or more air impellors are not in operation then airflow through any or all air filters can be primarily (or entirely) from the environment into the interior of the mask when the person inhales and primarily (or entirely) from the interior of the mask out into environment when the person exhales. Other design variations discussed elsewhere in this disclosure or in priority-linked disclosures can also be applied to this example where relevant.

Figure 35:
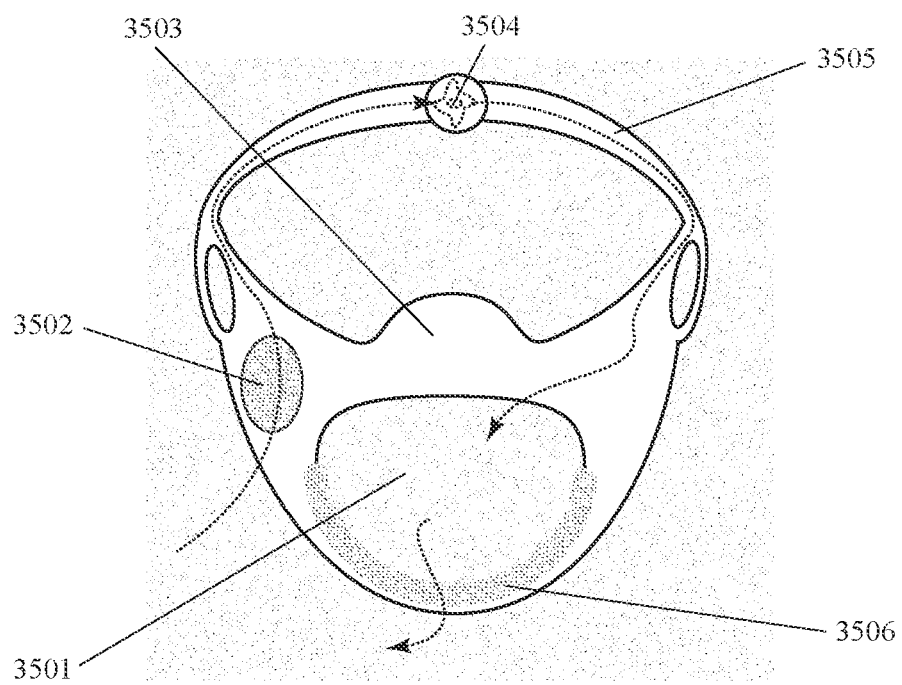
FIG. 35 shows a face mask with a transparent portion, a non-transparent portion, an air filter on the side of the mask, an air impellor on the back of a person's head, an air filter on the lower perimeter of the transparent portion, and air tubes or channels.

FIG. 35 shows an example of a pathogen-filtering semi-transparent face mask comprising: a transparent portion 3501 of a face mask which covers at least part of a person's mouth; a non-transparent portion 3503 of the face mask which holds the transparent portion on the person's head; a side air filter 3502 which is worn on a side (e.g. right side or left side) of the mask; a posterior air impellor 3504 which is worn on the back of the person's head, wherein the impellor draws air into the mask through the side air filter; an air channel (or tube) 3505 which is in fluid communication the side air filter, the posterior air impellor, and the transparent portion, wherein there is airflow from the side air filter to the transparent portion through the air channel; and a lower air filter 3506 which is at least partly below the person's mouth.

Locating an air impellor on the back of a person's head can have advantages. As one advantage, having an air impellor on the back of the head means that noise from rotation of the impellor is away from the person's ears (e.g. compared to having an air impellor on a person's cheek or directly behind their ear). As another advantage, having an air impellor on the back of the head can be better aesthetically by reducing facial clutter (e.g. compared to having an air impellor on a person's cheek or jaw). One could also locate the air filter/intake on the back of a person's head as well, but then the person wearing the mask cannot see potential environmental hazards near the mask air intake. For example, if someone wearing the mask is riding a subway, they cannot see if a person behind them is coughing directly toward the mask air intake. For this reason, this example features an air impellor on the back of a person's head (reducing noise near the person's ears and facial clutter) with the air filter/intake on the side of the person's face (allowing the person to see environmental hazards near the air intake).

In an example, when an air impellor is in operation then: airflow through a side air filter can be primarily (or entirely) from the environment into the interior of the mask; and airflow through a lower air filter can be primarily (or entirely) from the interior of the mask out into environment. In an example, when an air impellor is not in operation then airflow through all air filters can be primarily (or entirely) from the environment into the interior of the mask when the person inhales and primarily (or entirely) from the interior of the mask out into environment when the person exhales. Other design variations discussed elsewhere in this disclosure or in priority-linked disclosures can also be applied to this example where relevant.

Figure 36:
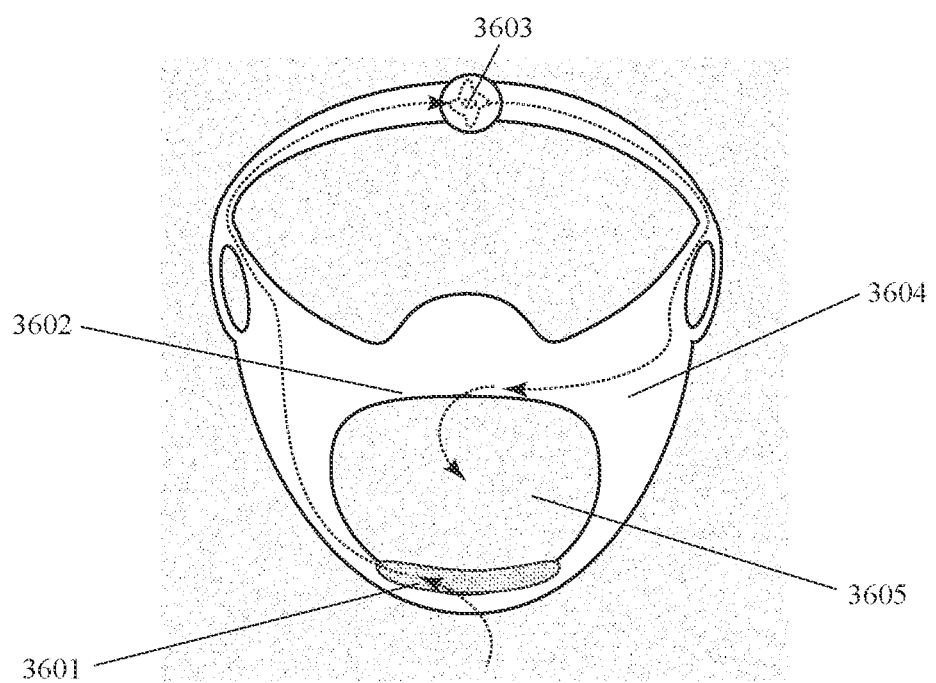
FIG. 36 shows a face mask with a transparent portion, a non-transparent portion, an air impellor on the back of a person's head, and an air filter on the lower perimeter of the transparent portion.

FIG. 36 shows an example of a pathogen-filtering semi-transparent face mask comprising: a transparent portion 3605 of a face mask with a perimeter 3602 which encircles a person's mouth; a non-transparent portion 3604 of the face mask which holds the transparent portion on the person's head; a lower air filter 3601 which is at least partly below the person's mouth; and a posterior air impellor 3603 which is worn on the back of the person's head, wherein the air impellor draws air into the mask through the side air filter. Other design variations discussed elsewhere in this disclosure or in priority-linked disclosures can also be applied to this example where relevant.

Figure 37:
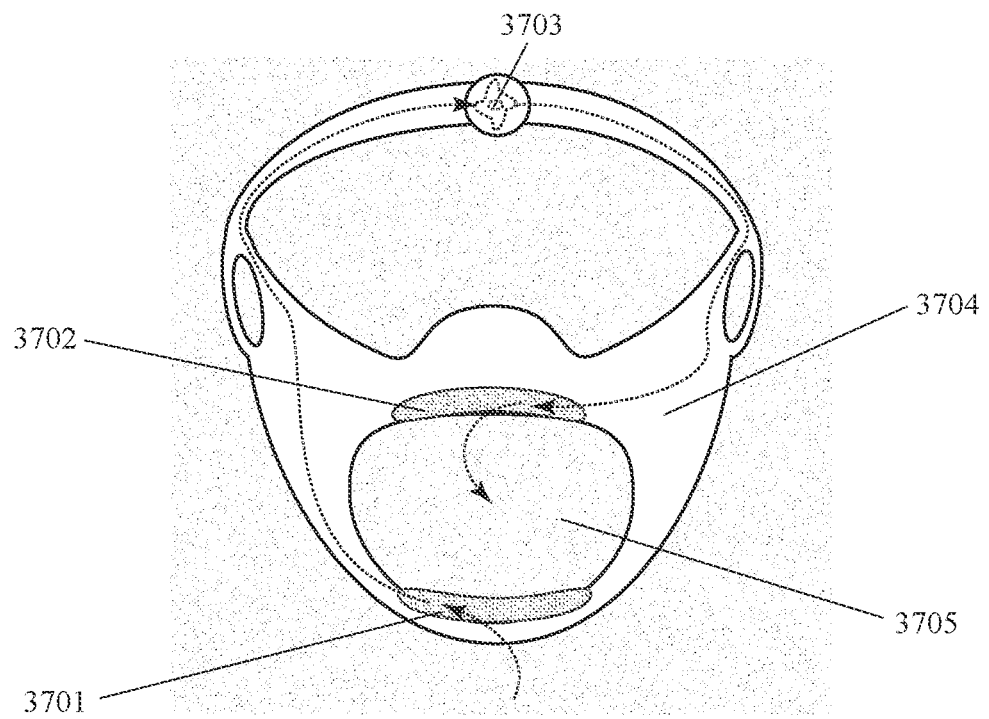
FIG. 37 shows a face mask with a transparent portion, a non-transparent portion, an air impellor on the back of a person's head, and upper and lower air filters around the perimeter of the transparent portion.

FIG. 37 shows an example of a pathogen-filtering semi-transparent face mask comprising: a transparent portion 3705 of a face mask which at least partly covers a person's mouth; a non-transparent portion 3704 of the face mask which holds the transparent portion on the person's head; a lower air filter 3701 which is at least partly below the person's mouth; an upper air filter 3702 which is at least partly above the person's mouth; and a posterior air impellor 3703 which is worn on the back of the person's head, wherein the air impellor draws air into the mask through the lower air filter. Other design variations discussed elsewhere in this disclosure or in priority-linked disclosures can also be applied to this example where relevant.

Figure 38:
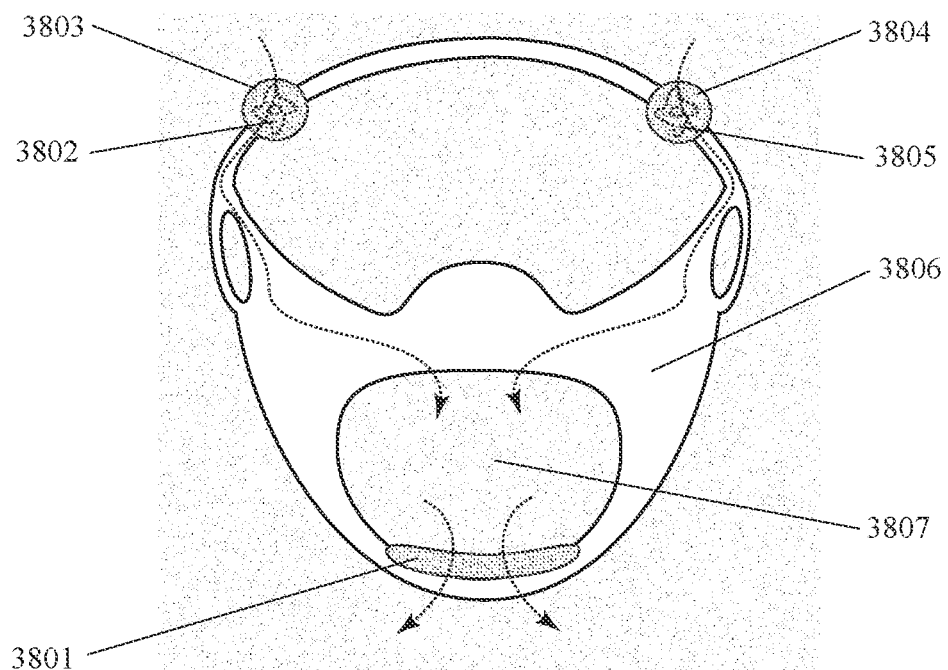
FIG. 38 shows a face mask with a transparent portion, a non-transparent portion, two air filters and air impellors on the back of a person's head, and an air filter on the lower perimeter of the transparent portion.

FIG. 38 shows an example of a pathogen-filtering semi-transparent face mask comprising: a transparent portion 3807 of a face mask which at least partly covers a person's mouth; a non-transparent portion 3806 of the face mask which holds the transparent portion on the person's head; a first posterior air filter 3803 which is worn on the back the person's head; a first posterior air impellor 3802 which is worn on the back of the person's head, wherein the first posterior air impellor moves air through the first posterior air filter; a second posterior air filter 3804 which is worn on the back the person's head; a second posterior air impellor 3805 which is worn on the back of the person's head, wherein the second posterior air impellor moves air through the second posterior air filter; and a lower air filter 3801 which is at least partly below the person's mouth.

In an example, a first posterior air filter and/or a first posterior air impellor can be on a first side (e.g. right side) of the back of a person's head and a second posterior air filter and/or a second posterior air impellor can be on a second side (e.g. left side) of the back of the person's head. In an example, air can enter a mask through a first posterior air filter and through a second posterior air filter. In an example, air can enter a mask through a first posterior air filter and exit the mask through a second posterior air filter. In an example, air can exit a mask through a lower air filter. In an example, a mask can further comprise one or more air tubes (or channels) which direct air from an air filter and/or air impellor on the back of a person's head to a concave interior of a transparent portion of the mask which covers the person's mouth. Other design variations discussed elsewhere in this disclosure or in priority-linked disclosures can also be applied to this example where relevant.

Figure 39:
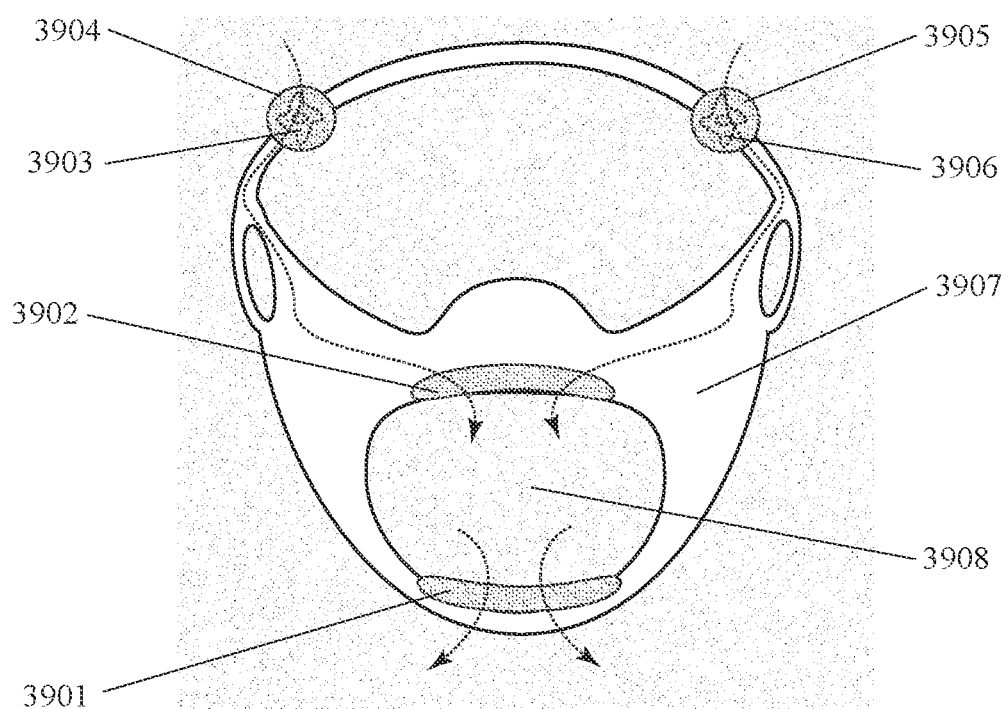
FIG. 39 shows a face mask with a transparent portion, a non-transparent portion, two air filters and air impellors on the back of a person's head, and upper and lower air filters around the perimeter of the transparent portion.

FIG. 39 shows an example of a pathogen-filtering semi-transparent face mask comprising: a transparent portion 3908 of a face mask which at least partly covers a person's mouth; a non-transparent portion 3907 of the face mask which holds the transparent portion on the person's head; a first posterior air filter 3904 which is worn on the back the person's head; a first posterior air impellor 3903 which is worn on the back of the person's head, wherein the first posterior air impellor moves air through the first posterior air filter; a second posterior air filter 3905 which is worn on the back the person's head; a second posterior air impellor 3906 which is worn on the back of the person's head, wherein the second posterior air impellor moves air through the second posterior air filter; an upper frontal air filter 3902 which is at least partly above the person's mouth; and a lower frontal air filter 3901 which is at least partly below the person's mouth.

In an example, a first posterior air filter and/or a first posterior air impellor can be on a first side (e.g. right side) of the back of a person's head and a second posterior air filter and/or a second posterior air impellor can be on a second side (e.g. left side) of the back of the person's head. In an example, air can enter a mask through a first posterior air filter and through a second posterior air filter. In an example, air can enter a mask through a first posterior air filter and exit the mask through a second posterior air filter. In an example, air can exit a mask through a lower frontal air filter. In an example, a mask can further comprise one or more air tubes (or channels) which direct air from an air filter and/or air impellor on the back of a person's head to a concave interior of a transparent portion of the mask which covers the person's mouth. Other design variations discussed elsewhere in this disclosure or in priority-linked disclosures can also be applied to this example where relevant.

Figure 40:
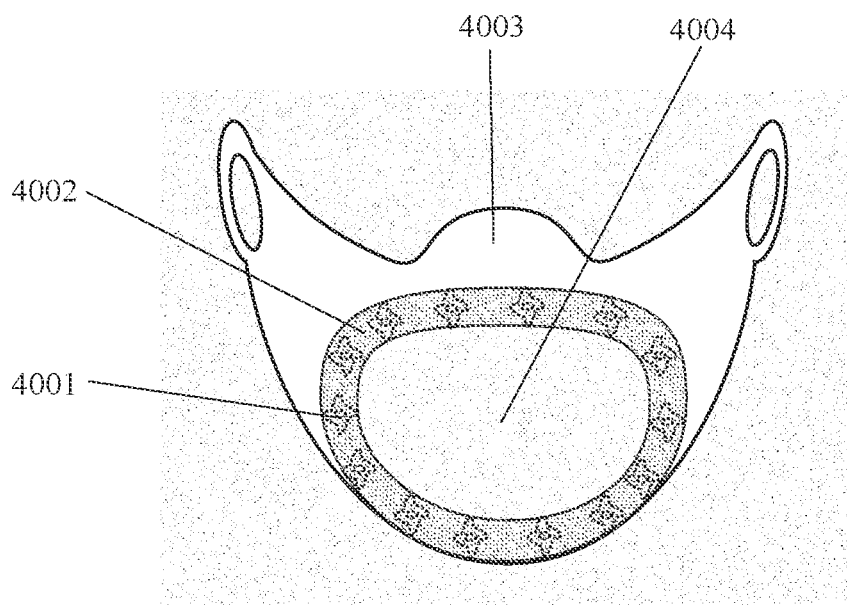
FIG. 40 shows a face mask with a transparent portion, a non-transparent portion, and an air filter and plurality of air impellors around the perimeter of the transparent portion.

FIG. 40 shows an example of a pathogen-filtering semi-transparent face mask comprising: a transparent portion 4004 of a face mask which covers at least part of a person's mouth; a non-transparent portion 4003 of the mask which holds the transparent portion on the person's head; a perimeter air filter 4002 along (e.g. around) at least part of the perimeter of the non-transparent portion; and a plurality of air impellors (including 4001) along (e.g. around) at least part of the perimeter of the non-transparent portion which move air through the perimeter air filter. In this example, the perimeter air filter and the plurality of air impellers span (e.g. encircle) the entire perimeter of the non-transparent portion of the mask.

There can be advantages from using a plurality of smaller air impellors instead of a single larger air impellor. One advantage is greater design flexibility with respect to the shape of an air exchange component on a mask. For example, a single large rotating impellor tends to require an air exchange component with a central circular cross-sectional shape. However, using a plurality of smaller air impellors instead of using one larger impellor can provide more design flexibility in the shape of an air exchange component on a mask. For example, one can create a linear or longitudinally-arcuate air exchange component by using a linear or longitudinally-arcuate array of air impellors. In an example, an arcuate array of air impellors can span some (or all) of an arcuate perimeter of a transparent portion of a mask. In an example, a circular array of air impellors can span a circular perimeter of a transparent portion of a mask. In an example, a linear array of air impellors can span some (or all) of a polygonal perimeter of a transparent portion of a mask.

The can also be other advantages from using a plurality of smaller air impellors instead of a single larger air impellor. In an example, a plurality of smaller air impellors can make less noise when rotating than a single larger air impellor. In an example, a plurality of smaller air impellors can move the same amount of air with a lower electric power requirement than a single larger air impellor. In an example, a plurality of smaller air impellors can produce more-uniform airflow than a single larger air impellor. In an example, a plurality of smaller air impellors can be safer than a single larger air impellor. In an example, a plurality of smaller air impellors can be substituted for a single larger air impellor in any of the other examples disclosed herein in order to achieve one of more of the above advantages.

In an example, the amount of airflow through an air filter can be adjusted by selectively changing the number of air impellors in a plurality of air impellors which are activated. In an example, the amount or direction of airflow through an air filter can be adjusted by selectively changing which air impellors in a plurality of air impellors which are activated. In an example, different air impellors in a plurality of air impellors can be activated in response to data from sensors which indicate how dirty and/or clogged different portions of an air filter are. In an example, different air impellors in a plurality of air impellors can be activated in response to data from biometric and/or physiological sensors which monitor the person. In an example, different air impellors in a plurality of air impellors can be activated in response to data from sensors which monitor air quality inside the mask (e.g. inside the transparent portion of the mask). In an example, different air impellors in a plurality of air impellors can be activated in response to data from environmental sensors. Other design variations discussed elsewhere in this disclosure or in priority-linked disclosures can also be applied to this example where relevant.

Figure 41:
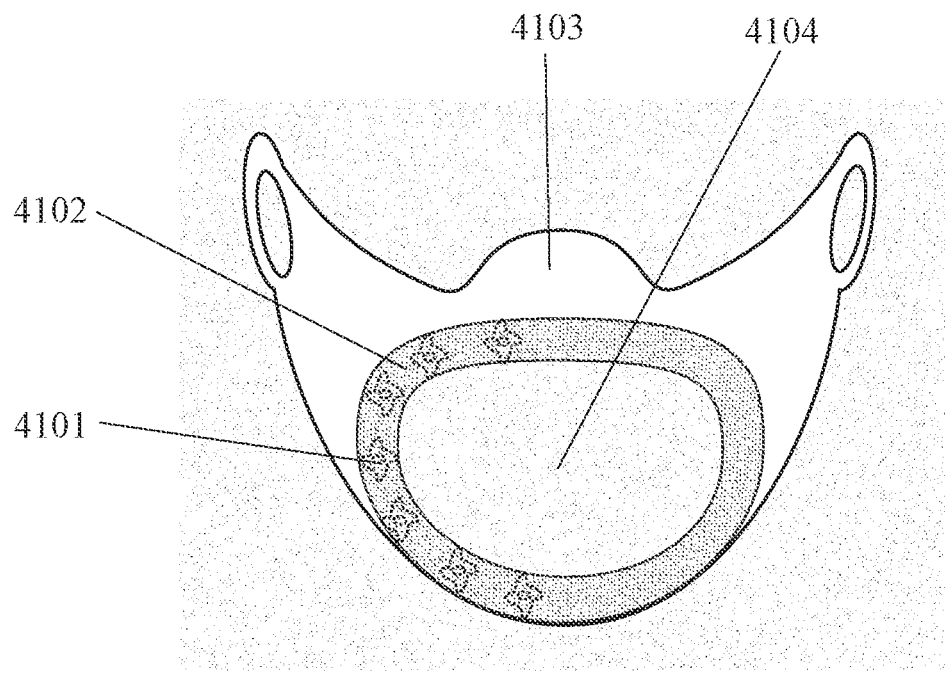
FIG. 41 shows a face mask with a transparent portion, a non-transparent portion, an air filter around the transparent portion, and a plurality of air impellors along a side of the transparent portion.

FIG. 41 shows an example of a pathogen-filtering semi-transparent face mask comprising: a transparent portion 4104 of a face mask which covers at least part of a person's mouth; a non-transparent portion 4103 of the mask which holds the transparent portion on the person's head; a perimeter air filter 4102 along (e.g. around) at least part of the perimeter of the non-transparent portion; and a plurality of air impellors (including 4101) along (e.g. around) at least part of the perimeter of the non-transparent portion which move air through the perimeter air filter.

In this example, a plurality of air impellers spans between 40% and 60% of the perimeter of a non-transparent portion of the mask. In this example, the perimeter air filter spans (e.g. encircles) the entire perimeter of the non-transparent portion of the mask and the plurality of air impellers spans one side (e.g. the right side or the left side) of the non-transparent portion. In an example, an arcuate array of air impellors can span some (or all) of an arcuate perimeter of a transparent portion of a mask. In an example, a circular array of air impellors can span a circular perimeter of a transparent portion of a mask. In an example, a linear array of air impellors can span some (or all) of a polygonal perimeter of a transparent portion of a mask.

There can be advantages from using a plurality of smaller air impellors instead of a single larger air impellor. One advantage is greater design flexibility with respect to the shape of an air exchange component on a mask. For example, a single large rotating impellor tends to require an air exchange component with a central circular cross-sectional shape. However, using a plurality of smaller air impellors instead of using one larger impellor can provide more design flexibility in the shape of an air exchange component on a mask. For example, one can create a linear or longitudinally-arcuate air exchange component by using a linear or longitudinally-arcuate array of air impellors.

The can also be other advantages from using a plurality of smaller air impellors instead of a single larger air impellor. In an example, a plurality of smaller air impellors can make less noise when rotating than a single larger air impellor. In an example, a plurality of smaller air impellors can move the same amount of air with a lower electric power requirement than a single larger air impellor. In an example, a plurality of smaller air impellors can produce more-uniform airflow than a single larger air impellor. In an example, a plurality of smaller air impellors can be safer than a single larger air impellor. In an example, a plurality of smaller air impellors can be substituted for a single larger air impellor in any of the other examples disclosed herein in order to achieve one of more of the above advantages.

In an example, the amount of airflow through an air filter can be adjusted by selectively changing the number of air impellors in a plurality of air impellors which are activated. In an example, the amount or direction of airflow through an air filter can be adjusted by selectively changing which air impellors in a plurality of air impellors which are activated. In an example, different air impellors in a plurality of air impellors can be activated in response to data from sensors which indicate how dirty and/or clogged different portions of an air filter are. In an example, different air impellors in a plurality of air impellors can be activated in response to data from biometric and/or physiological sensors which monitor the person. In an example, different air impellors in a plurality of air impellors can be activated in response to data from sensors which monitor air quality inside the mask (e.g. inside the transparent portion of the mask). In an example, different air impellors in a plurality of air impellors can be activated in response to data from environmental sensors. Other design variations discussed elsewhere in this disclosure or in priority-linked disclosures can also be applied to this example where relevant.

Figure 42:
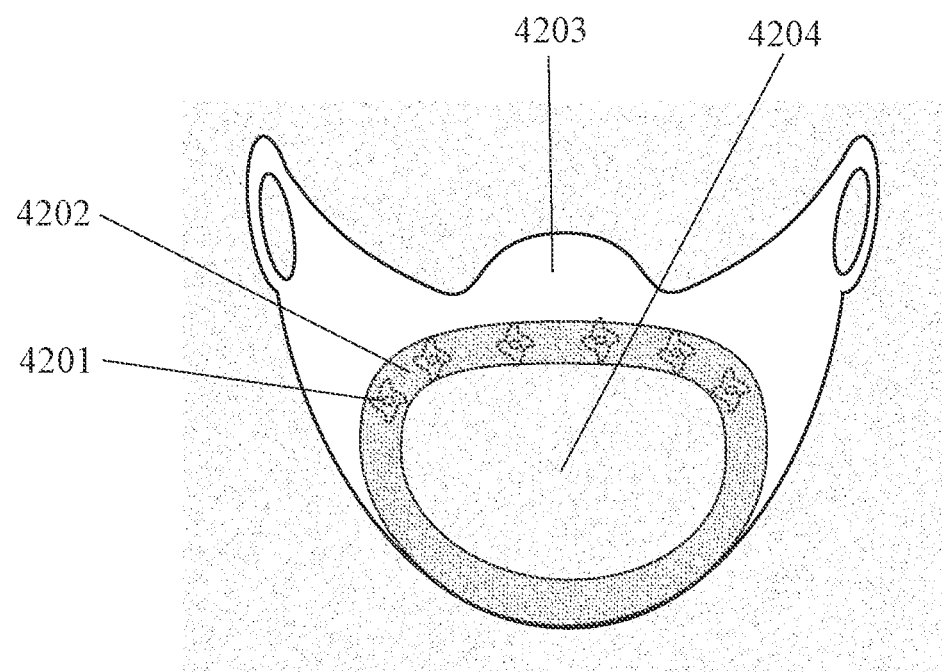
FIG. 42 shows a face mask with a transparent portion, a non-transparent portion, an air filter around the transparent portion, and a plurality of air impellors along the upper perimeter of the transparent portion.

FIG. 42 shows an example of a pathogen-filtering semi-transparent face mask comprising: a transparent portion 4204 of a face mask which covers at least part of a person's mouth; a non-transparent portion 4203 of the mask which holds the transparent portion on the person's head; a perimeter air filter 4202 along (e.g. around) at least part of the perimeter of the non-transparent portion; and a plurality of air impellors (including 4201) along (e.g. around) at least part of the perimeter of the non-transparent portion which move air through the perimeter air filter.

In this example, a plurality of air impellers spans between 40% and 60% of the perimeter of a non-transparent portion of the mask. In this example, the perimeter air filter spans (e.g. encircles) the entire perimeter of the non-transparent portion of the mask and the plurality of air impellers spans the upper of the non-transparent portion. In an example, an arcuate array of air impellors can span some (or all) of an arcuate perimeter of a transparent portion of a mask. In an example, a circular array of air impellors can span a circular perimeter of a transparent portion of a mask. In an example, a linear array of air impellors can span some (or all) of a polygonal perimeter of a transparent portion of a mask.

There can be advantages from using a plurality of smaller air impellors instead of a single larger air impellor. One advantage is greater design flexibility with respect to the shape of an air exchange component on a mask. For example, a single large rotating impellor tends to require an air exchange component with a central circular cross-sectional shape. However, using a plurality of smaller air impellors instead of using one larger impellor can provide more design flexibility in the shape of an air exchange component on a mask. For example, one can create a linear or longitudinally-arcuate air exchange component by using a linear or longitudinally-arcuate array of air impellors.

The can also be other advantages from using a plurality of smaller air impellors instead of a single larger air impellor. In an example, a plurality of smaller air impellors can make less noise when rotating than a single larger air impellor. In an example, a plurality of smaller air impellors can move the same amount of air with a lower electric power requirement than a single larger air impellor. In an example, a plurality of smaller air impellors can produce more-uniform airflow than a single larger air impellor. In an example, a plurality of smaller air impellors can be safer than a single larger air impellor. In an example, a plurality of smaller air impellors can be substituted for a single larger air impellor in any of the other examples disclosed herein in order to achieve one of more of the above advantages.

In an example, the amount of airflow through an air filter can be adjusted by selectively changing the number of air impellors in a plurality of air impellors which are activated. In an example, the amount or direction of airflow through an air filter can be adjusted by selectively changing which air impellors in a plurality of air impellors which are activated. In an example, different air impellors in a plurality of air impellors can be activated in response to data from sensors which indicate how dirty and/or clogged different portions of an air filter are. In an example, different air impellors in a plurality of air impellors can be activated in response to data from biometric and/or physiological sensors which monitor the person. In an example, different air impellors in a plurality of air impellors can be activated in response to data from sensors which monitor air quality inside the mask (e.g. inside the transparent portion of the mask). In an example, different air impellors in a plurality of air impellors can be activated in response to data from environmental sensors. Other design variations discussed elsewhere in this disclosure or in priority-linked disclosures can also be applied to this example where relevant.

Figure 43:
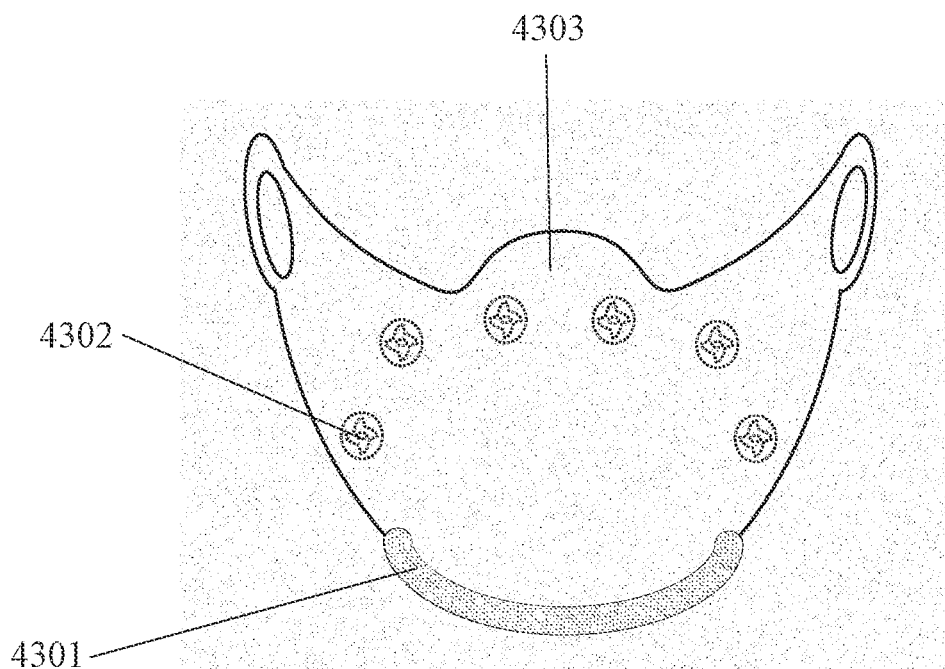
FIG. 43 shows a face mask with a transparent portion, a concave array of air impellors, and a lower perimeter air filter.

FIG. 43 shows an example of a pathogen-filtering semi-transparent face mask comprising: a transparent portion 4303 of a face mask which covers at least part of a person's mouth; an array of air impellors (including 4302) on the face mask which draw air from the environment into the face mask; and a perimeter air filter 4301 which spans (e.g. goes along) at least part of the perimeter of the face mask.

There can be advantages from using an array of smaller air impellors instead of a single larger air impellor. One advantage is greater design flexibility with respect to the shape of an air exchange component on a mask. For example, a single large rotating impellor tends to require an air exchange component with a central circular cross-sectional shape. However, using an array of smaller air impellors instead of using one larger impellor can provide more design flexibility in the shape of an air exchange component on a mask. For example, one can create a longitudinal arcuate air exchange component by using a longitudinal arcuate array of air impellors.

The can be other advantages from using an array of smaller air impellors instead of a single larger air impellor. In an example, an array of smaller air impellors can make less noise when rotating than a single larger air impellor. In an example, an array of smaller air impellors can move the same amount of air with a lower electric power requirement than a single larger air impellor. In an example, an array of smaller air impellors can produce more-uniform airflow than a single larger air impellor. In an example, an array of smaller air impellors can be safer than a single larger air impellor. In an example, an array of smaller air impellors can be substituted for a single larger air impellor in any of the other examples disclosed herein in order to achieve one of more of these advantages.

In an example, an array of air impellors on a face mask can collectively have a conic section shape. In an example, an array of air impellors can collectively form a concave arc. In an example, an array of air impellors can collectively form a concave arc with a downward-facing concavity (e.g. like a frown). In an example, an array of air impellors can collectively form a concave arc with an upward-facing concavity (e.g. like a smile). In an example, an array of air impellors can collectively form a circle, ellipse, or oval (e.g. around a person's mouth). In an example, an array of air impellors can be above a person's mouth. In an example, an array of air impellors can be below a person's mouth. In an example, there can be between 3 and 6 air impellors in an array of air impellors. In an example, there can be 3 air impellors in an array of air impellors. In an example, there can be between 4 and 8 air impellors in an array of air impellors.

In an example, an array of air impellors can span from a first side of a mask (e.g. the right side) to a second side of the mask (e.g. the left side). In an example, there can be a first array of air impellors on a first side of a mask (e.g. the right side) and a second array of air impellors on a second side of the mask (e.g. the left side). In an example, a face mask can comprise: a first arcuate array of air impellors on a first side of a mask (e.g. the right side) with a concavity which faces toward the second side (e.g. the left side); and a second arcuate array of air impellors on a second side of the mask (e.g. the left side) with a concavity which faces toward the first side (e.g. the right side).

In an example, the amount of airflow through (e.g. into and out of) a mask can be adjusted by selectively changing the number of air impellors in an array of air impellors which are activated and/or the speeds at which those air impellors rotate. In an example, the amount or direction of airflow through an air filter can be adjusted by selectively changing which air impellors in an array of air impellors which are activated. In an example, different air impellors in an array of air impellors can be activated in response to data from sensors which indicate how dirty and/or clogged different portions of an air filter are. In an example, different air impellors in an array of air impellors can be activated in response to data from biometric and/or physiological sensors which monitor the person. In an example, different air impellors in an array of air impellors can be activated in response to data from sensors which monitor air quality inside the mask (e.g. inside the transparent portion of the mask). In an example, different air impellors in a plurality of air impellors can be activated in response to data from environmental sensors.

In an example, a mask can further comprise a separate air filter in fluid communication with each air impellor. In an example, a mask can comprise an array of pairs of air filters and air impellors. Alternatively, a face mask can further comprise a single air filter which is in fluid communication with all air impellors. In an example, one or more air impellors in an array of air impellors can be individually and selectively activated. In an example, the number of air impellors in an array which are activated to move air can be proportional to the level of airborne pathogen threat in a given location or situation. In an example, the number of air impellors in an array which are activated to move air can be proportional to the oxygen requirement for the person wearing the mask at a given time (e.g. based on the person's activity or biometric sensor readings). In an example, the rotational directions of one or more rotating air impellors in an array of air impellors can be individually and selectively reversed.

In an example, a perimeter air filter can span at least part of the lower perimeter of a face mask. In an example, a perimeter air filter can span at least part of the lower perimeter of a transparent portion of a face mask. In an example, a perimeter air filter can span at least part of the upper perimeter of a face mask. In an example, a perimeter air filter can span at least part of the upper perimeter of a transparent portion of a face mask. In an example, a perimeter air filter can span at least part of the lower perimeter of a person's mouth. In an example, a perimeter air filter can span at least part of the upper perimeter of a person's mouth. In an example, a mask can comprise right-side and left-side air filters instead of a perimeter air filter. Other design variations discussed elsewhere in this disclosure or in priority-linked disclosures can also be applied to this example where relevant.

Figure 44:
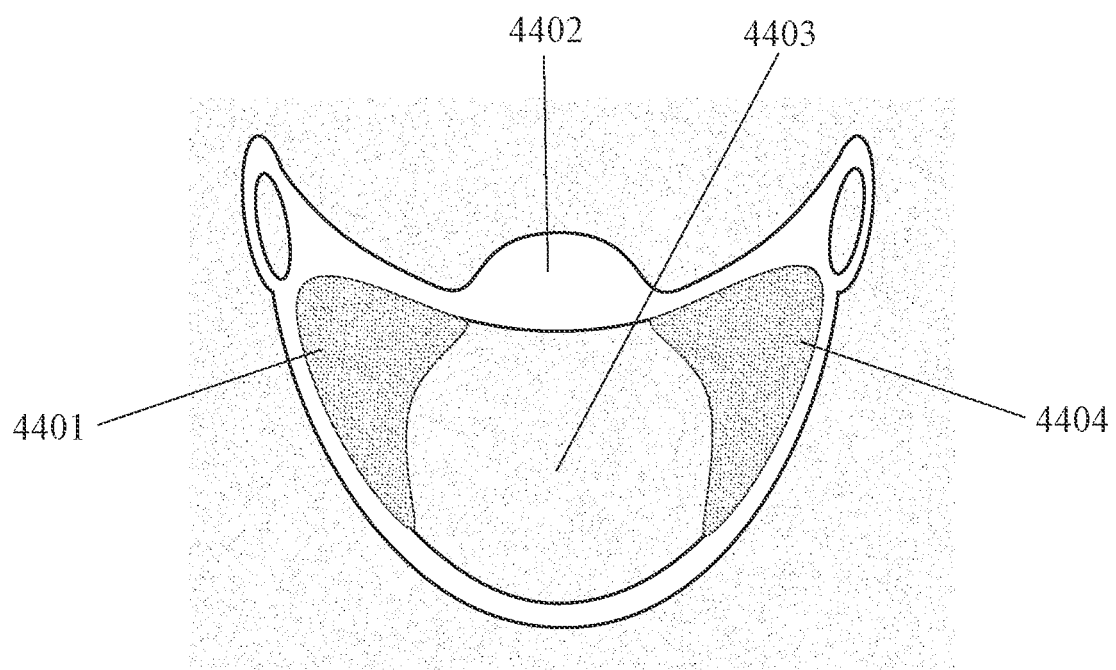
FIG. 44 shows a face mask with a transparent portion, a non-transparent portion, and air filters to the left and right of the transparent portion.

FIG. 44 shows an example of a pathogen-filtering semi-transparent face mask comprising: a transparent portion 4403 of a face mask which covers at least part of a person's mouth; a non-transparent portion 4402 of the face mask which holds the transparent portion on the person's head; a right-side air filter 4401 to the right of the transparent portion; and a left-side air filter 4404 to the left of the transparent portion.

In an example, a transparent portion of a face mask can cover (and/or span) a person's entire mouth. In an example, a transparent portion can cover a person's mouth and also portions of the person's cheeks. In an example, a transparent portion can cover a person's mouth, portions of the person's cheeks, and also a lower portion of the person's nose. In an example, the maximum distance from a transparent portion of a face mask to a person's mouth can be within the range of ½" to 3". In an example, the maximum distance from a transparent portion of a face mask to a person's mouth can be within the range of 1" to 4".

In an example, a transparent portion of a face mask can have a concave shape, wherein the concave interior of the transparent portion faces towards the person's mouth. In an example, a transparent portion of a face mask can have an arcuate concave shape. In an example, a transparent portion can have a shape which is a section of a sphere. In an example, a transparent portion can have a hemispherical shape. In an example, a transparent portion can have a shape which is a section of an oblate spheroid. In an example, a transparent portion can have a shape which is a section of an ellipsoid. In an example, a transparent portion can have a frustal shape. In an example, a transparent portion can have a shape which is a section of a round cylinder. In an example, a transparent portion can have a shape which is a section of a polygonal (e.g. quadrilateral, hexagonal, or octagonal) cylinder. In an example, a transparent portion can be shaped like the upper surface of a bicycle seat. In an example, a transparent portion can be shaped like the upper surface of a saddle.

In an example, a transparent portion of a face mask can be impermeable to air. In an example, a transparent portion of a face mask can be less permeable to air than a non-transparent portion of a face mask. In an example, a transparent portion can be less flexible than a non-transparent portion. In an example, a transparent portion can be rigid. In an example, a transparent portion can be made with a transparent polymer. In an example, a transparent portion can be coated with an anti-fogging coating. In an example, a transparent portion of a face mask can be heated to reduce fogging. In an example, airflow from an air impellor can be directed across the mouth-facing surface of a transparent portion of a face mask to reduce fogging.

In an example, a non-transparent portion of a face mask can hold a transparent portion of a face mask on a person's head by being attached to (e.g. looping around) the person's ears. In an example, a non-transparent portion can hold the transparent portion on a person's head by being attached to (e.g. looping around) the rear of the person's head. In an example, a non-transparent portion can comprise straps, bands, cords, or strings. In an example, a non-transparent portion can comprise four straps, bands, cords, or strings. In an example, a non-transparent portion can comprise two straps, bands, cords, or strings. In an example, a non-transparent portion can comprise elastic and/or stretchable straps, bands, cords, or strings. In an example, a non-transparent portion can comprise fabric straps. In an example, a non-transparent portion can be made from a flexible fabric and/or textile. In an example, a non-transparent portion can be permeable to air. In an example, a non-transparent portion can be impermeable to air. In an example, a non-transparent portion can be less permeable to air than an air filter.

In an example, a transparent portion and a non-transparent portion of a face mask can be attached to each other by sewing or weaving. In an example, a transparent portion and a non-transparent portion can be attached to each other by adhesion and/or gluing. In an example, a transparent portion and a non-transparent portion can be attached to each other by melting and/or welding. In an example, a transparent portion and a non-transparent portion can be attached to each other by snaps, clips, clamps, hooks, pins, prongs, or buttons.

In an example, a side air filter can be contiguous to a transparent portion of a face mask. In an example, a side air filter can be contiguous to the side perimeter of a transparent portion of a face mask. In an example, a side air filter can be attached to the side perimeter of a transparent portion of a face mask. In an example, a side air filter can span between 20% and 40% of the perimeter of a transparent portion of a face mask. In an example, a side air filter can be contiguous with between 20% and 40% of the perimeter of a transparent portion of a face mask. In an example, a side air filter can span between 30% and 50% of the perimeter of a transparent portion of a face mask. In an example, a side air filter can be contiguous with between 30% and 50% of the perimeter of a transparent portion of a face mask.

In an example, a side air filter can have a shape selected from the group consisting of: an arrowhead shape, a Nike™ swoosh shape, a Star-Trek™ badge shape (turned sideways), a parabolic shape; and a conic section shape. In an example, a side air filter can have a filtration area with the range of ½ square inch to 3 square inches. In an example, a side air filter can have a filtration area with the range of 2 to 6 square inches. In an example, right-side and left-side air filters can be symmetric with respect to a central vertical plane of a mask. In an example, right-side and left-side air filters can be passive air filters. Alternatively, right-side and left-side air filters can be active air filters, wherein the right-side air filter is paired with a right-side air impellor and the left-side air filter is paired with a left-side air impellor.

In an example, a side air filter can be removably attached to a face mask via a clip, snap, clasp, hook, clamp, adhesive substance, or pin. In an example, a side air filter can be disposable. In an example, a side air filter can be detached from a face mask, cleaned, and then reattached to the face mask. In an example, a mask can further comprise a sensor which tracks the cumulative airflow through an upper filter and indicates when the side air filter should be changed and/or cleaned. In an example, a mask can further comprise a sensor which tracks the level of airflow resistance through an upper filter and indicates when the side air filter should be changed and/or cleaned. In an example, there can be two air filters, wherein the mask directs airflow through a first filter until a sensor detects that the first filter is dirty, at which time the mask automatically redirects airflow through a second filter. In an example, a side air filter can further comprise two air filters, wherein the mask directs air through a second filter when the first filter becomes dirty and/or clogged.

In an example, a face mask can further comprise one or more components selected from the group consisting of: data processor, power source (e.g. battery), data transmitter/receiver, biometric and/or physiological sensor, environmental sensor, microphone, speaker, interior mask light, exterior mask light, ultraviolet light emitter in optical communication with airflow within the mask, touch screen, push buttons or switches, a strap or band which loops around the back of a person's head, and a strap or band which loops over the top of a person's head. In an example, a face mask can further comprise a microphone which is in acoustic communication with the interior of the mask (e.g. with the interior of the transparent portion) and a speaker which reproduces sound recorded by the microphone. In an example, a face mask can further comprise a microphone on the inside of the mask which records a person's voice and a speaker on the outside of the mask which reproduces the person's voice. In an example, a face mask can further comprise one or more lights on the inside of the mask which highlight a person's mouth in order to increase visibility of the person's mouth (e.g. lip motion and facial expression) by nearby people. Other design variations discussed elsewhere in this disclosure or in priority-linked disclosures can also be applied to this example where relevant.

Figure 45:
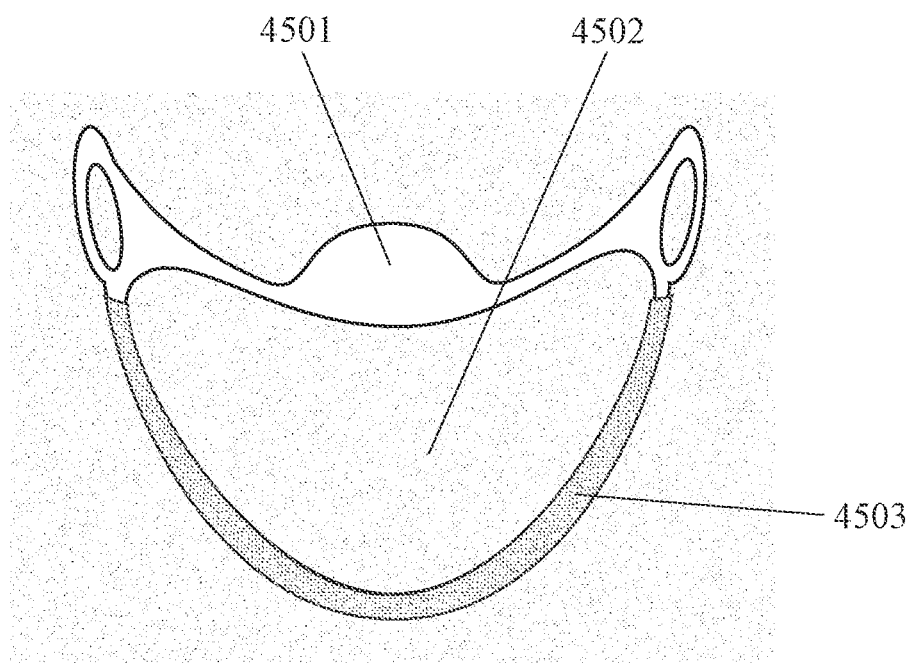
FIG. 45 shows a face mask with a transparent portion, a non-transparent portion, and an air filter along the lower perimeter of the mask.

FIG. 45 shows an example of a pathogen-filtering semi-transparent face mask comprising: a transparent portion 4502 of a face mask which covers at least part of a person's mouth; a non-transparent portion 4501 of the face mask which holds the transparent portion on the person's head; and a lower air filter 4503 which is at least partly below the person's mouth.

In an example, a transparent portion of a face mask can cover (and/or span) a person's entire mouth. In an example, a transparent portion can cover a person's mouth and also portions of the person's cheeks. In an example, a transparent portion can cover a person's mouth, portions of the person's cheeks, and also a lower portion of the person's nose. In an example, the maximum distance from a transparent portion of a face mask to a person's mouth can be within the range of ½" to 3". In an example, the maximum distance from a transparent portion of a face mask to a person's mouth can be within the range of 1" to 4".

In an example, a transparent portion of a face mask can have a concave shape, wherein the concave interior of the transparent portion faces towards the person's mouth. In an example, a transparent portion of a face mask can have an arcuate concave shape. In an example, a transparent portion can have a shape which is a section of a sphere. In an example, a transparent portion can have a hemispherical shape. In an example, a transparent portion can have a shape which is a section of an oblate spheroid. In an example, a transparent portion can have a shape which is a section of an ellipsoid. In an example, a transparent portion can have a frustal shape. In an example, a transparent portion can have a shape which is a section of a round cylinder. In an example, a transparent portion can have a shape which is a section of a polygonal (e.g. quadrilateral, hexagonal, or octagonal) cylinder. In an example, a transparent portion can be shaped like the upper surface of a bicycle seat. In an example, a transparent portion can be shaped like the upper surface of a saddle. In an example, a transparent portion can be shaped like a large smile and/or mouth.

In an example, a transparent portion of a face mask can be impermeable to air. In an example, a transparent portion of a face mask can be less permeable to air than a non-transparent portion of a face mask. In an example, a transparent portion can be less flexible than a non-transparent portion. In an example, a transparent portion can be rigid. In an example, a transparent portion can be made with a transparent polymer. In an example, a transparent portion can be coated with an anti-fogging coating. In an example, a transparent portion of a face mask can be heated to reduce fogging. In an example, airflow from an air impellor can be directed across the mouth-facing surface of a transparent portion of a face mask to reduce fogging.

In an example, a non-transparent portion of a face mask can hold a transparent portion of a face mask on a person's head by being attached to (e.g. looping around) the person's ears. In an example, a non-transparent portion can hold the transparent portion on a person's head by being attached to (e.g. looping around) the rear of the person's head. In an example, a non-transparent portion can comprise straps, bands, cords, or strings. In an example, a non-transparent portion can comprise four straps, bands, cords, or strings. In an example, a non-transparent portion can comprise two straps, bands, cords, or strings. In an example, a non-transparent portion can comprise elastic and/or stretchable straps, bands, cords, or strings. In an example, a non-transparent portion can comprise fabric straps. In an example, a non-transparent portion can be made from a flexible fabric and/or textile. In an example, a non-transparent portion can be permeable to air. In an example, a non-transparent portion can be impermeable to air. In an example, a non-transparent portion can be less permeable to air than an air filter.

In an example, a transparent portion and a non-transparent portion of a face mask can be attached to each other by sewing or weaving. In an example, a transparent portion and a non-transparent portion can be attached to each other by adhesion and/or gluing. In an example, a transparent portion and a non-transparent portion can be attached to each other by melting and/or welding. In an example, a transparent portion and a non-transparent portion can be attached to each other by snaps, clips, clamps, hooks, pins, prongs, or buttons.

In an example, a lower air filter can be at least partly below (e.g. have a lower height than the bottom of) a person's mouth. In an example, a lower air filter can be entirely below (e.g. have a lower height than the bottom of) a person's mouth. In an example, a lower air filter can be located directly below a person's mouth. In an example, a lower air filter can be on and/or below a person's jaw. In an example, a lower air filter can span a person's jaw substantially from one ear to the other. In an example, a lower air filter can be on and/or below a person's chin. In an example, a lower air filter can be arcuate with an upward-facing concavity.

In an example, a lower air filter can span at least part of the lower perimeter of a face mask. In an example, a lower air filter can span at least part of the lower perimeter of the transparent portion a face mask. In an example, a lower air filter can span between 20% and 40% of the lower perimeter of a face mask. In an example, a lower air filter can span between 20% and 40% of the lower perimeter of the transparent portion a face mask. In an example, a lower air filter can span between 30% and 80% of the lower perimeter of a face mask. In an example, a lower air filter can span between 30% and 80% of the lower perimeter of the transparent portion a face mask. In an example, a lower air filter can span the entire lower perimeter of a face mask. In an example, a lower air filter can span the entire lower perimeter of the transparent portion a face mask.

In an example, a lower air filter can be removably attached to a face mask via a clip, snap, clasp, hook, clamp, adhesive substance, or pin. In an example, a lower air filter can be disposable. In an example, a lower air filter can be detached from a face mask, cleaned, and then reattached to the face mask. In an example, a mask can further comprise a sensor which tracks the cumulative airflow through an upper filter and indicates when the lower air filter should be changed and/or cleaned. In an example, a mask can further comprise a sensor which tracks the level of airflow resistance through an upper filter and indicates when the lower air filter should be changed and/or cleaned. In an example, there can be two air filters, wherein the mask directs airflow through a first filter until a sensor detects that the first filter is dirty, at which time the mask automatically redirects airflow through a second filter. In an example, a lower air filter can further comprise two air filters, wherein the mask directs air through a second filter when the first filter becomes dirty and/or clogged.

In an example, a face mask can further comprise one or more components selected from the group consisting of: data processor, power source (e.g. battery), data transmitter/receiver, biometric and/or physiological sensor, environmental sensor, microphone, speaker, interior mask light, exterior mask light, ultraviolet light emitter in optical communication with airflow within the mask, touch screen, push buttons or switches, a strap or band which loops around the back of a person's head, and a strap or band which loops over the top of a person's head. In an example, a face mask can further comprise a microphone which is in acoustic communication with the interior of the mask (e.g. with the interior of the transparent portion) and a speaker which reproduces sound recorded by the microphone. In an example, a face mask can further comprise a microphone on the inside of the mask which records a person's voice and a speaker on the outside of the mask which reproduces the person's voice. In an example, a face mask can further comprise one or more lights on the inside of the mask which highlight a person's mouth in order to increase visibility of the person's mouth (e.g. lip motion and facial expression) by nearby people. Other design variations discussed elsewhere in this disclosure or in priority-linked disclosures can also be applied to this example where relevant.

Figure 46:
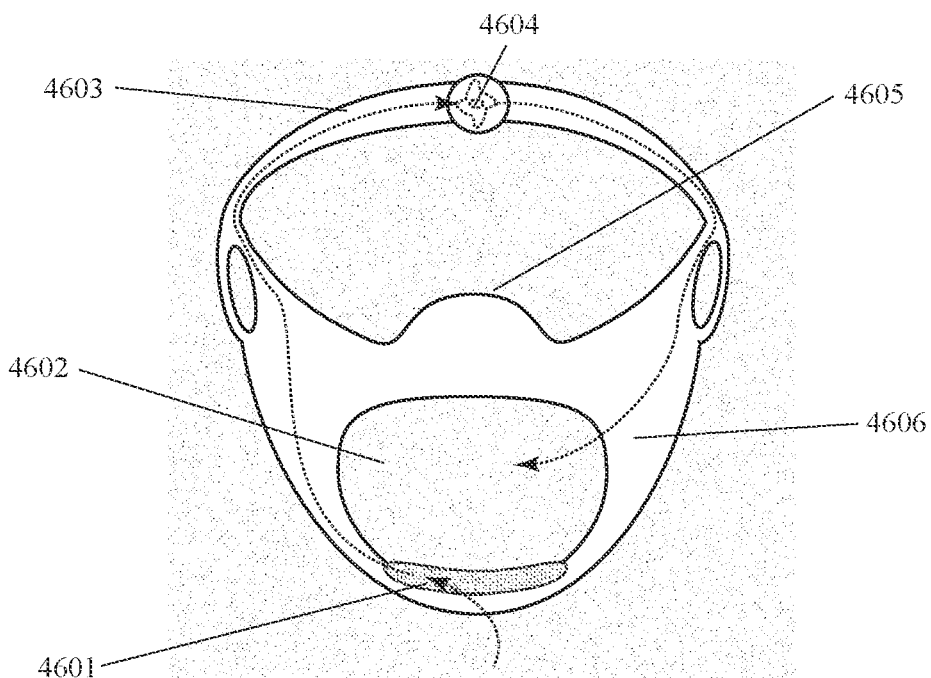
FIG. 46 shows a face mask with a transparent portion, an air impellor on the back of a person's head, and an air filter on the lower perimeter of the transparent portion.

FIG. 46 shows a pathogen-air filtering face mask comprising: a face mask 4605 which is configured to be worn by a person; wherein the face mask further comprises a front portion 4606 which is configured to be worn on the person's face and a rear portion 4603 which curves around the rear of the person's head; wherein the front portion further comprises a transparent portion 4602 which is configured to be worn over the person's mouth; wherein the front portion further comprises an air filter 4601; and wherein the rear portion further comprises one or more air impellors (e.g. air impellors, fans, turbines, propellers, pumps, and/or blowers) 4604 which draw air into the face mask through the air filter. Other design variations discussed elsewhere in this disclosure or in priority-linked disclosures can also be applied to this example where relevant.

Figure 47:
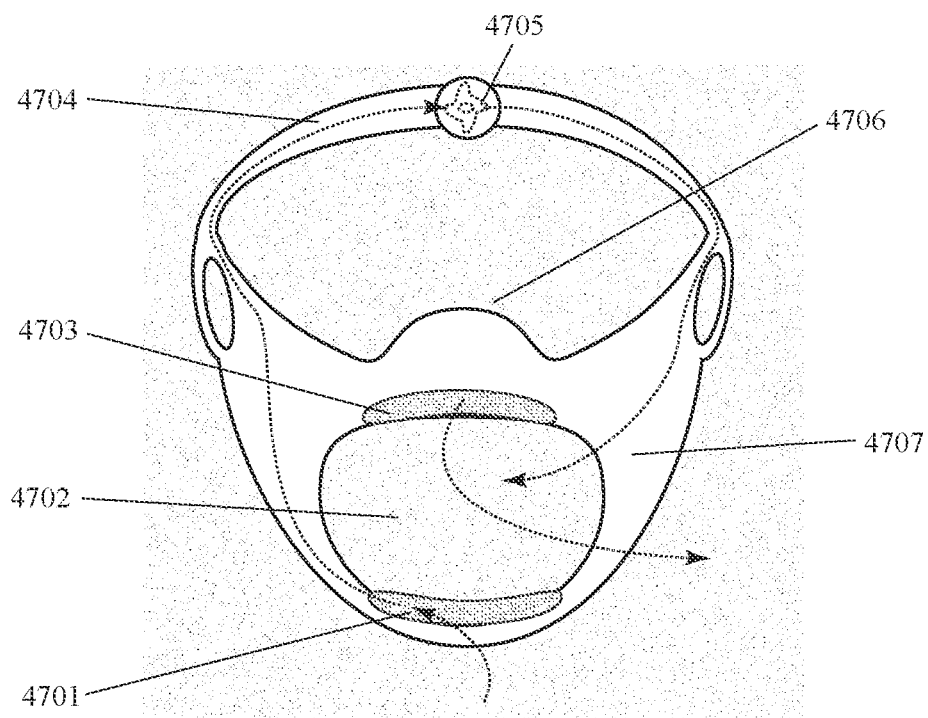
FIG. 47 shows a face mask with a transparent portion, an air impellor on the back of a person's head, and upper and lower air filters around the perimeter of the transparent portion.

FIG. 47 shows a pathogen-air filtering face mask comprising: a face mask 4706 which is configured to be worn by a person; wherein the face mask further comprises a front portion 4707 which is configured to be worn on the person's face and a rear portion 4704 which curves around the rear of the person's head; wherein the front portion further comprises a transparent portion 4702 which is configured to be worn over the person's mouth; wherein the front portion further comprises an air intake filter 4701; wherein the front portion further comprises an air exhaust filter 4703; and wherein the rear portion further comprises one or more air impellors (e.g. air impellors, fans, turbines, propellers, pumps, and/or blowers) 4705 which draw air into the face mask through the air intake filter and out from the face mask through the air exhaust filter. Other design variations discussed elsewhere in this disclosure or in priority-linked disclosures can also be applied to this example where relevant.

Figure 48:
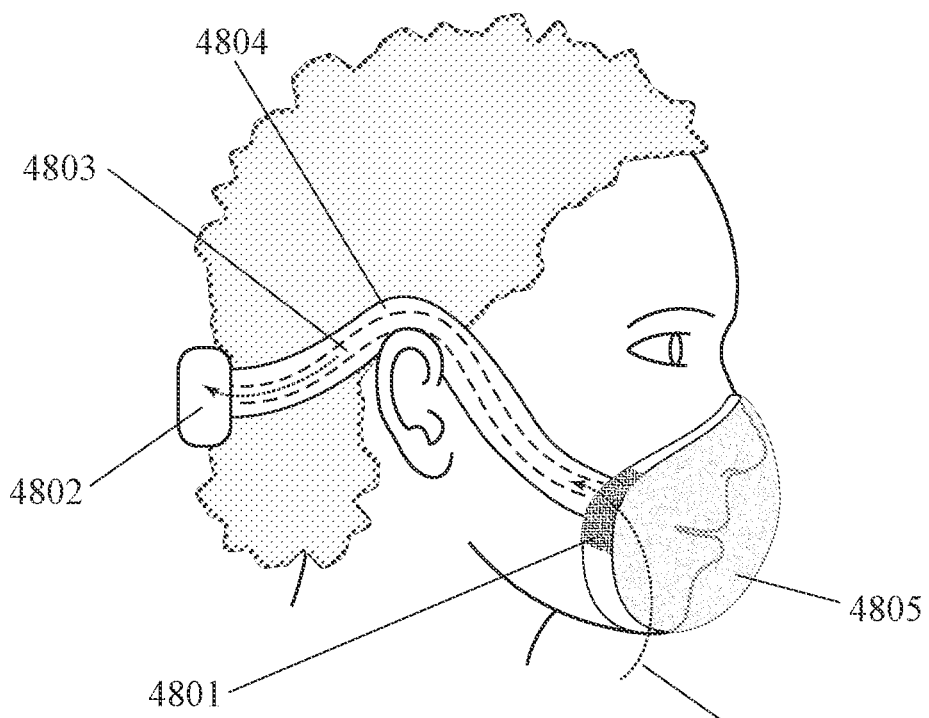
FIGS. 48 and 49 show right-side and left-side views of a face mask with a transparent portion, an air impellor on the back of a person's head, air tubes or channels which conduct air between the transparent portion and the air impeller, and right-side and left-side air filters near the transparent portion.
Figure 49:
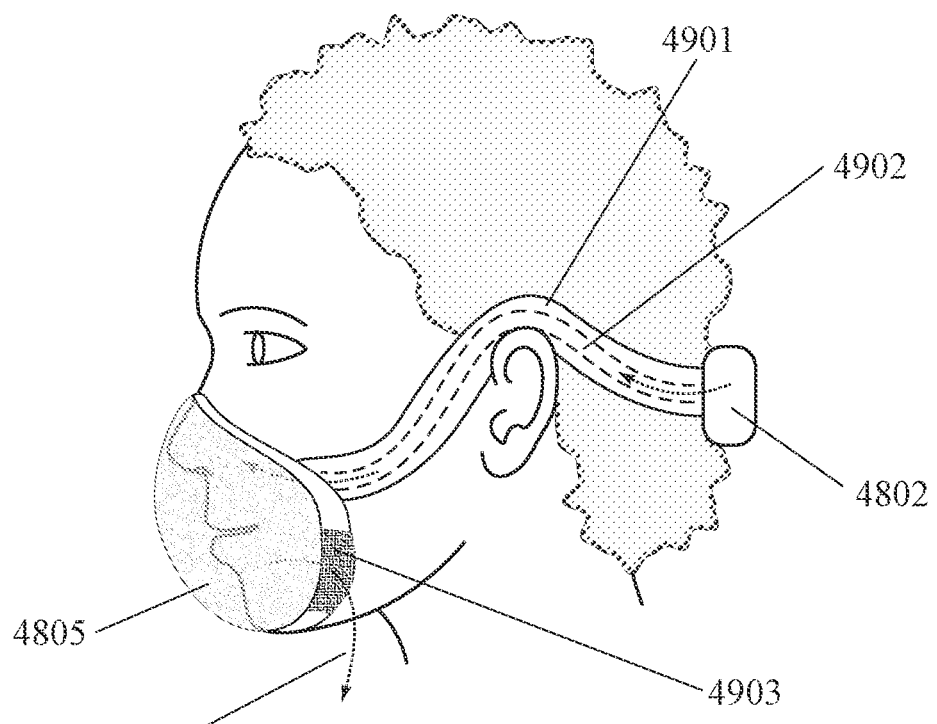

FIGS. 48 and 49 show right-side and left-side views, respectively, of an example of a protective, pathogen-filtering face mask with an impellor worn on the back of a person's head or neck. This example comprises: a face mask, a concave transparent portion of the face mask 4805 which covers a person's mouth; an air intake filter 4801 on a front portion of the face mask; an air exhaust filter 4903 on a front portion of the face mask; a first air tube (or channel) 4803; a second air tube (or channel) 4902; and an air impellor (e.g. air impellor, fan, turbine, propeller, pump, and/or blower) 4802 on the back of the person's head or neck; wherein air 4806 flows from the air intake filter to the air impellor through the first air tube (or channel); and wherein air flows from the air impellor to the concave interior of the transparent portion through the second air tube (or channel). The example shown in FIGS. 48 and 49 also shows a right-side strap 4804 and a left-side strap 4901 which hold the face mask on the person's head and contain the first air tube (or channel) and the second air tube (or channel), respectively.

In an example, a concave transparent portion can have a perimeter with a shape like the perimeter of a bicycle seat. In an example, it can have a cardioid shape. In an example, a face mask can have a non-transparent portion around the perimeter of a transparent portion. In an example, a face mask can have a compressible seal around a non-transparent portion. In an example, a transparent portion of a face mask can have a first level of compressibility and/or flexibility, a seal around the transparent portion can have a second level of compressibility and/or flexibility, and the second level can be greater than the first level.

In an example, an air intake filter on a front portion of a face mask can located be to one side (e.g. to the right or left) of a transparent portion of the face mask and an air exhaust filter on the front portion of the face mask can located be to the other side (e.g. to the left or right) of the transparent portion. In an example, an air intake filter on a front portion of a face mask can above a transparent portion of the face mask and an air exhaust filter on the front portion of the face mask can be below the transparent portion. In an example, an air intake filter on a front portion of a face mask can below a transparent portion of the face mask and an air exhaust filter on the front portion of the face mask can be above the transparent portion. In an example, an air intake filter on a front portion of a face mask can below a transparent portion of the face mask and an air exhaust filter on the front portion of the face mask can also be below the transparent portion. In an example, an air intake filter on a front portion of a face mask can above a transparent portion of the face mask and an air exhaust filter on the front portion of the face mask can also be above the transparent portion.

In an example, an air intake port on a front portion of a face mask can located be to one side (e.g. to the right or left) of a transparent portion of the face mask and an air exhaust port on the front portion of the face mask can located be to the other side (e.g. to the left or right) of the transparent portion. In an example, an air intake port on a front portion of a face mask can above a transparent portion of the face mask and an air exhaust port on the front portion of the face mask can be below the transparent portion. In an example, an air intake port on a front portion of a face mask can below a transparent portion of the face mask and an air exhaust port on the front portion of the face mask can be above the transparent portion. In an example, an air intake port on a front portion of a face mask can below a transparent portion of the face mask and an air exhaust port on the front portion of the face mask can also be below the transparent portion. In an example, an air intake port on a front portion of a face mask can above a transparent portion of the face mask and an air exhaust port on the front portion of the face mask can also be above the transparent portion.

In an example, a first air tube (or channel) which conducts air between an air intake filter and an air impellor (e.g. air impellor, fan, turbine, propeller, pump, and/or blower) on the back of a person's head can be located on a first side (e.g. right or left) of a person's head and a second air tube (or channel) which conducts air between an air impellor and a transparent portion of a mask can be located on a second side (e.g. left or right) of the person's head. In an example, first and second air tubes or channels can both be located on the same side (e.g. right or left) of a person's head. In an example, a first and/or second air tube (or channel) can loop above and around a person's ear. In an example, a first and/or second air tube (or channel) can loop below and around a person's ear. In an example, a first and/or second air tube (or channel) can be within a strap (e.g. an elastic fabric strap) which attaches a front portion of a mask to a person's head. Other design variations discussed elsewhere in this disclosure or in priority-linked disclosures can also be applied to this example where relevant.

I claim:

1. A protective face mask comprising:
a face mask;
a concave transparent portion of the face mask which is configured to cover a person's mouth;
an air intake filter which is configured to be below the person's mouth and/or on the person's chin;
an air exhaust filter;
a first air tube or channel;
a second air tube or channel; and
an air impellor which is configured to be worn on the back of the person's head or neck;
wherein air flows from the air intake filter to the air impellor through the first air tube or channel, and wherein air flows from the air impellor to a concave interior of the transparent portion through the second air tube or channel.

2. A protective face mask comprising:
a face mask;
a concave transparent portion of the face mask which is configured to cover a person's mouth;
an air intake port which is configured to be below the person's mouth and/or on the person's chin;
an air exhaust port;
an air intake filter;
an air exhaust filter;
a first air tube or channel;
second air tube or channel; and
an air impellor which is configured to be worn on the back of the person's head or neck;
wherein air flows in from the environment to the air intake port, wherein air flows from the air intake port to the air intake filter, wherein air flows from the air intake filter to the air impellor through the first air tube or channel, wherein air flows from the air impellor to a concave interior of the transparent portion through the second air tube or channel, and wherein air flows out from the concave interior of the transparent portion to the environment through the air exhaust port.

3. A protective face mask comprising:
a face mask;
wherein the face mask further comprises a concave transparent portion which is configured to cover a person's mouth;
wherein the face mask further comprises an air intake port which is configured to be below the person's mouth and/or on the person's chin;
wherein the face mask further comprises an air intake filter;
wherein the face mask further comprises an air impellor, fan, turbine, propeller, pump, and/or blower configured to be located on the back of the person's head or neck;
wherein the face mask further comprises a first air tube or channel which conducts air from the air intake filter to the air impellor, fan, turbine, propeller, pump, and/or blower, wherein the first air tube or channel is at least 5" long;
wherein the face mask further comprises a second air tube or channel which conducts air from the air impellor, fan, turbine, propeller, pump, and/or blower to a concave interior of the transparent portion, wherein the second air tube or channel is at least 5" long;
an air exhaust filter; and
an air exhaust port.

* * * * *